(12) United States Patent
Sawyer

(10) Patent No.: US 11,845,745 B2
(45) Date of Patent: *Dec. 19, 2023

(54) TRI-SUBSTITUTED IMIDAZOLES FOR THE INHIBITION OF TGF BETA AND METHODS OF TREATMENT

(71) Applicant: Clavius Pharmaceuticals, LLC., Ashland, VA (US)

(72) Inventor: J. Scott Sawyer, Placitas, NM (US)

(73) Assignee: Clavius Pharmaceuticals, LLC., Wilmington, DE (US)

(*) Notice: Subject to any disclaimer, the term of this patent is extended or adjusted under 35 U.S.C. 154(b) by 153 days.

This patent is subject to a terminal disclaimer.

(21) Appl. No.: 17/476,943

(22) Filed: Sep. 16, 2021

(65) Prior Publication Data

US 2022/0073514 A1 Mar. 10, 2022

Related U.S. Application Data

(63) Continuation of application No. 16/496,703, filed as application No. PCT/US2018/024133 on Mar. 23, 2018, now Pat. No. 11,124,509.

(60) Provisional application No. 62/475,451, filed on Mar. 23, 2017.

(51) Int. Cl.
| | |
|---|---|
| *A61K 31/4178* | (2006.01) |
| *A61K 31/415* | (2006.01) |
| *A61P 35/00* | (2006.01) |
| *C07D 471/04* | (2006.01) |
| *C07D 401/14* | (2006.01) |
| *C07D 403/14* | (2006.01) |

(52) U.S. Cl.
CPC ......... *C07D 471/04* (2013.01); *C07D 401/14* (2013.01); *C07D 403/14* (2013.01)

(58) Field of Classification Search
CPC .... A61K 31/4178; A61K 31/415; A61P 35/00
See application file for complete search history.

(56) References Cited

U.S. PATENT DOCUMENTS

| 8,080,568 B1 | 12/2011 | Kim et al. |
| 11,124,509 B2 | 9/2021 | Sawyer |
| 2012/0252721 A1 | 10/2012 | Dousson et al. |
| 2016/0096823 A1 | 4/2016 | McMillen et al. |
| 2016/0257690 A1 | 9/2016 | Kinsella et al. |

FOREIGN PATENT DOCUMENTS

| JP | 2010-503702 | 2/2010 |
| JP | 2011-515371 | 5/2011 |
| JP | 2011-526295 | 10/2011 |
| JP | 2011-529021 | 12/2011 |
| JP | 2012-514044 | 12/2011 |
| JP | 2014-514296 | 6/2014 |
| JP | 2014-520846 | 8/2014 |
| JP | 2016-535745 | 11/2016 |
| JP | 2018-501209 | 1/2018 |
| JP | 2018-510857 | 4/2018 |
| JP | 2020-512400 | 4/2020 |
| WO | WO 2008/094556 | 8/2008 |
| WO | WO 2009/115572 | 9/2009 |
| WO | WO 2009/158473 | 12/2009 |
| WO | WO 2013/009140 | 1/2013 |
| WO | WO 2016/081364 | 5/2016 |
| WO | WO 2016/140884 | 9/2016 |
| WO | WO 2018/068759 | 4/2018 |

OTHER PUBLICATIONS

Callahan et al., "Identification of Novel Inhibitors of the Transforming Growth Factor β1 (TGF-β1) Type 1 Receptor (ALK5)," Journal of Medicinal Chemistry, vol. 45, No. 5, Jan. 30, 2002, pp. 999-1001. Abstract only.
Ren et al., "Pharmacophore modeling and virtual screening for the discovery of new transforming growth factor-β type I receptor (ALK5) inhibitors," European Journal of Medicinal Chemistry, vol. 44, No. 11, Nov. 2009, pp. 4259-4265. Abstract only.
Article 94(3) Communication for Europe Patent Application No. 18823320.9, dated Mar. 23, 2022, 4 pages.
Official Action (with English translation) for Japan Patent Application No. 2020-501434, dated Aug. 23, 2022, 10 pages.
Official Action (with English translation) for Japan Patent Application No. 2021-509918, dated Feb. 8, 2022, 7 pages.
Notice of Allowance (with English translation of allowed claims) for Japan Patent Application No. 2021-509918, dated Aug. 23, 2022, 45 pages.
U.S. Appl. No. 17/269,959, Sawyer.
"RN 1269148-53-9 Registry," Supplied by ChemBridge Corporation, Chemical Abstracts Service, Mar. 21, 2011, 1 page.
Gaikwad et al., "The Use of Bioisoterism in Drug Design and Molecular Modification," American Journal of PharmTech Research, vol. 2, No. 4, 2012, 23 pages.
Guo et al., "Synthesis and biological evaluation of 1,2,4-trisubstituted imidazoles as inhibitors of transforming growth factor-β type I receptor (ALK5)," Bioorganic & Medicinal Chemistry Letters, vol. 23, No. 21, No. 1, 2013, pp. 5850-5854. Abstract only.
Jin et al., "Discovery of N-((4-([1,2,4]Triazolo[1,5-a]pyridin-6-yl)-5-(6-methylpyridin-2-yl)-1H-imidazol-2-yl)methyl)-2-fluoroaniline (EW-7197): A Highly Potent, Selective, and Orally Bioavailable Inhibitor of TGF-β Type I Receptor Kinase as Cancer Immunotherapeutic/Antifibrotic Agent," Journal of Medical Chemistry, vol. 57, No. 10, May 2, 2014, pp. 4213-4238.
International Search Report and Written Opinion for International (PCT) Patent Application No. PCT/US2017/024133, dated Jun. 15, 2018, 8 pages.
Extended European Search Report for European Patent Application No. 18823320.9, dated Jul. 29, 2020, 10 pages.
Official Action (with English translation) for Japan Patent Application No. 2020-501434, dated Nov. 30, 2021, 15 pages.
International Search Report and Written Opinion for International (PCT) Patent Application No. PCT/US2019/047650, dated Dec. 27, 2019, 10 pages.
Official Action for U.S. Appl. No. 16/496,703, dated Sep. 22, 2020, 9 pages.
Official Action for U.S. Appl. No. 16/496,703, dated Feb. 5, 2021, 6 pages.
Notice of Allowance for U.S. Appl. No. 16/496,703, dated May 14, 2021, 5 pages.
Extended European Search Report for European Patent Application No. 19852789.7, dated Jun. 1, 2022, 1.
Article 94(3) Communication for Europe Patent Application No. 19852789.7, dated Feb. 9, 2023, 4 pages.

*Primary Examiner* — Bruck Kifle
(74) *Attorney, Agent, or Firm* — Sheridan Ross P.C.

(57) ABSTRACT

Pharmaceutical compounds, their methods of manufacture, and methods of treatment of mammals with pharmaceutical compounds are provided.

17 Claims, No Drawings

TRI-SUBSTITUTED IMIDAZOLES FOR THE INHIBITION OF TGF BETA AND METHODS OF TREATMENT

CROSS REFERENCE TO RELATED APPLICATIONS

This application is a continuation of U.S. patent application Ser. No. 16/496,703, filed 23 Sep. 2019, which is a national-stage application under 35 U.S.C. § 371 and claims the benefit of PCT Application PCT/US2018/024133 having an international filing date of 23 Mar. 2018, which designated the United States and claimed the benefit of U.S. Provisional Patent Application 62/475,451, filed 23 Mar. 2017. The disclosure of each of the above-referenced applications is incorporated herein by reference in its entirety.

FIELD OF THE DISCLOSURE

This disclosure relates to small molecular weight substituted imidazoles that inhibit the TGF-β signaling pathway. More specifically, this disclosure relates to methods of using said substituted imidazoles for the treatment of diseases related to the TGF-β signaling pathways including, but not limited to, atherosclerosis, Marfan syndrome, Loeys-Dietz syndrome, obesity, diabetes, multiple sclerosis, keratoconus, idiopathic pulmonary fibrosis, Alzheimer's Disease, chronic kidney disease, and scleroderma.

The compounds disclosed herein may be especially applicable to the treatment of various oncology indications, including, but not limited to, lung cancer, gastric cancer, myelodysplastic syndrome (MDS), melanoma, colon cancer, renal cancer, and preferably glioblastoma (GBM), pancreatic cancer, and hepatocellular carcinoma (HCC). These diseases may be treated in mammals, including domesticated quadrupeds and preferably humans. The compounds of the present disclosure may be active in inhibiting the kinase domains of the Type I receptors (ACVR1B, also known as ALK4, TGFβR1, also known as ALK5, BMPR1A, also known as ALK3, BMPR1B, also known as ALK6, and ACVR1C, also known as ALK7) and/or the Type II receptors (ACVR2A, ACVR2B, BMPR2, and TGFβRII).

BACKGROUND

The TGF-β signaling pathway is known to regulate a number of cellular processes involving growth, differentiation, development, migration, and apoptosis. TGF-β superfamily ligands, including TGF-β1, TGF-β2, and TGF-β3, bind to various combinations of Type I and Type II receptors in overall hexameric complexes consisting of two identical ligands bound to a heterotetrameric receptor complex, ultimately resulting in the phosphorylation of the Type I receptor and subsequent phosphorylation and activation of SMAD2/SMAD3 intracellular signaling proteins. The cascade thus initiated results in further activation of downstream signaling elements ultimately activating a number of nuclear transduction proteins controlling transcription. The signaling pathway comprised of TGF-β/ALK5 combinations is especially important in oncology indications, and may be disrupted by blocking the key kinase domain of the ALK5 receptor.

Despite the existence of known ALK5 inhibitors, additional classes of compounds are needed to probe potential efficacy in the diverse diseases mentioned above, particularly in the area of oncology. Improvements over existing inhibitors could include, but not be limited to, greater therapeutic indices, more favorable formulation or biopharmaceutical properties, or more optimized tissue distribution. The compounds of the present disclosure are believed to have utility in treating the diseases described above.

SUMMARY

The present invention provides substituted imidazoles for the inhibition of the TGF-β signaling pathway and methods for treating disease employing said compounds.

DETAILED DESCRIPTION

As described above, this disclosure includes small molecular weight substituted imidazoles that may inhibit the TGF-β signaling pathways. More specifically, this disclosure relates to methods of using said substituted imidazoles for the treatment of diseases related to the TGF-β signaling pathways including, but not limited to, atherosclerosis, Marfan syndrome, Loeys-Dietz syndrome, obesity, diabetes, multiple sclerosis, keratoconus, idiopathic pulmonary fibrosis, Alzheimer's Disease, chronic kidney disease, and scleroderma.

The compounds disclosed herein therefore, may be especially applicable to the treatment of various oncology indications, including, but not limited to, lung cancer, gastric cancer, myelodysplastic syndrome (MDS), melanoma, colon cancer, renal cancer, and preferably glioblastoma (GBM), pancreatic cancer, and hepatocellular carcinoma (HCC). These diseases may be treated in mammals, including domesticated quadrupeds and preferably humans. The compounds within the present disclosure may be active in inhibiting the kinase domains of the Type I receptors (ACVR1B, also known as ALK4, TGFβR1, also known as ALK5, BMPR1A, also known as ALK3, BMPR1B, also known as ALK6, and ACVR1C, also known as ALK7) and/or the Type II receptors (ACVR2A, ACVR2B, BMPR2, and TGFβRII).

Compounds of the invention include compounds as embodied by the structure below and all pharmaceutically acceptable salts, hydrates, or other solvates thereof.

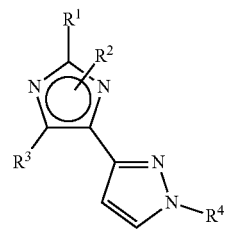

In various embodiments of this disclosure, $R^1$ may be selected from the group consisting of a group represented by the formula —X—Y—Z, the formula —X—Z, the formula —Y—Z, or the formula —Z wherein;

X represents O; $NR^5$; S; $CR^6R^7$; C=O; C=S; or an alkyl chain containing 1 to 6 carbon atoms:

Y represents O, $NR^5$, S, $CR^6R^7$, C=O, C=S, or an alkyl chain containing 1 to 6 carbon atoms, $R^5$ represents hydrogen; aryl; heteromonocyclic; heterobicyclic; an alkyl chain containing 1 to 6 carbon atoms; an alkenyl chain containing 1 to 6 carbon atoms; or an alkynyl chain containing 1 to 6 carbon atoms;

$R^6$ represents hydrogen; or an alkyl chain containing 1 to 6 carbon atoms;

$R^7$ represents hydrogen; an alkyl chain containing 1 to 6 carbon atoms; an alkenyl group containing 1 to 6 carbon atoms; an alkynyl chain containing 1 to 6 carbon atoms; or an alkoxy group containing 1 to 6 carbon atoms:

Z represents:
a phenyl group;
a substituted phenyl group or substituted heteromonocyclic group where 1 to 5 substituents are selected from a group consisting of halogens, alkyl groups containing 1 to 6 carbon atoms, alkenyl groups containing 1 to 6 carbon atoms, alkynyl groups containing 1 to 6 carbon atoms, a phenyl group, a pyridyl group, alkoxy groups containing 1 to 6 carbon atoms, a hydroxyl group, an amido group, a carbamoyl group, and a cyano group:
a hydrogen atom;
an alky group containing 1 to 12 carbon atoms;
an alkenyl group containing 2 to 12 carbon atoms;
an alkynyl group containing 1 to 6 carbon atoms;
a cycloalkyl group containing 3 to 7 carbon atoms;
an alkyl group containing 1 to 12 carbon atoms substituted by an alkenyl group containing 1 to 6 carbon atoms, an alkynyl group containing 1 to 6 carbon atoms, an alkoxy group containing 1 to 6 carbon atoms, a hydroxyl group, an alkoxyphenylalkoxy group having 8 to 12 carbon atoms, a morpholino group, a piperidinyl group, a pyrrolidino group, or a cyclic ether containing 3 to 6 carbon atoms; an alkyl group having 1 to 6 carbon atoms substituted with 1 to 5 halogen atoms;
a cycloalkyl group containing 3 to 9 carbon atoms substituted with an oxo group;
a heteromonocyclic or heterobicyclic group;
a heteromonocyclic or a heterobicyclic group substituted with 1 to 5 members selected from a group consisting of halogens, alkyl groups containing 1 to 6 carbon atoms, alkenyl groups containing 1 to 6 carbon atoms, alkynyl groups containing 1 to 6 carbon atoms, alkoxy groups containing 1 to 6 carbon atoms, a hydroxyl group, an amido group, a carbamoyl group, a cyano group, or specifically a tetrahydropyranyl group;
a tetrahydrofuranyl group;
a 4-piperidinyl group;
a piperidinyl group substituted with an alkyl group containing 1 to 6 carbon atoms;
a t-butoxycarbonyl group;
a cyclohexanespiro-2'-(1,3-dioxoranyl) group; or
a pyrrolidin-2-one-5-yl group.

In various embodiments of this disclosure, $R^2$ may represent:
a hydrogen atom;
an alkyl group containing 1 to 6 carbon atoms;
an alkenyl group containing 1 to 6 carbon atoms;
an alkynyl group containing 1 to 6 carbon atoms,
a cycloalkyl group containing 3 to 7 carbon atoms;
an alkyl group containing 1 to 6 carbon atoms, substituted with a cycloalkyl group containing 3 to 7 carbon atoms;
an alkyl group containing 1 to 6 carbon atoms, substituted with 2 to 7 halogens;
a phenylalkyl group containing 7 to 12 carbon atoms; or
a phenylalkyl group containing 7 to 12 carbon atoms, substituted with a hydroxyl group, an alkoxy group containing 1 to 6 carbon atoms, an alkoxy group containing 1 to 6 carbon atoms substituted with an alkoxy group containing 1 to 6 carbon atoms, or an alkoxy group having 1 to 6 carbon atoms substituted with an alkylamino group containing 1 to 6 carbon atoms;

$R^3$ may represent:
a phenyl group;
a phenyl group substituted with 1 to 5 members selected from a group consisting of halogens, alkyl groups containing 1 to 6 carbon atoms, alkenyl groups containing 1 to 6 carbon atoms, alkynyl groups containing 1 to 6 carbon atoms, alkoxy groups containing 1 to 6 carbon atoms, a phenyl group, a pyridyl group, a hydroxyl group, an amido group, a carbamoyl group, and a cyano group;
a heteromonocyclic or heterobicyclic group;
a heteromonocyclic or a heterobicyclic group substituted with 1 to 5 members selected from a group consisting of halogens, alkyl groups containing 1 to 6 carbon atoms, a phenyl group, a pyridyl group, alkoxy groups containing 1 to 6 carbon atoms, a hydroxyl group, an amido group, a carbamoyl group, and a cyano group; or
a substituted 3H-quinazolin-4-one.

$R^4$ may represent:
a hydrogen atom;
an alkyl group containing 1 to 12 carbon atoms;
an alkenyl group containing 1 to 6 carbon atoms;
an alkynyl group containing 1 to 6 carbon atoms;
a cycloalkyl group containing 3 to 7 carbon atoms;
a cyclic ether containing 3 to 6 carbon atoms;
an alkyl group containing 1 to 12 carbon atoms substituted by an alkoxy group containing 1 to 6 carbon atoms, a hydroxyl group, an alkoxyphenylalkoxy group having 8 to 12 carbon atoms, a morpholino group, a piperidinyl group, a pyrrolidino group, or a cyclic ether containing 3 to 6 carbon atoms;
an alkyl group having 1 to 6 carbon atoms substituted with 1 to 7 halogen atoms;
a cycloalkyl group containing 3 to 9 carbon atoms substituted with an oxo group;
a tetrahydropyranyl group;
a tetrahydrofuranyl group; or
a 4-piperidinyl group.

As used herein, the term "halogen" may be understood to include a fluorine, chlorine, bromine, or an iodine atom.

The term "alkyl" may be understood to include a saturated aliphatic hydrocarbon containing a specified number of carbon atoms in either a straight-chain or branched-chain configuration. Examples include, but are not limited to, methyl, ethyl, n-propyl, isopropyl, n-butyl, isobutyl, sec-butyl, tert-butyl, n-pentyl, neopentyl, n-hexyl, and n-heptyl. Alkyl groups may be optionally substituted with one or more substituents including groups such as alkoxy, cycloalkoxy, amino, nitro, cyano, carboxy, halogen, hydroxyl, sulfonyl, or mercapto.

The term "alkenyl" may be understood to refer to an unsaturated aliphatic hydrocarbon group containing a specified number of carbon atoms, in either a straight-chain or branched-chain configuration, and at least one double bond. Examples include, but are not limited to ethylene, propylene, isopropylene, butylene, isobutylene, sec-butylene, tert-butylene, n-pentylene, n-hexylene, and n-heptylene. As used herein, alkenyl groups may be substituted with one or more substituents including groups such as alkoxy, cycloalkoxy, heterocycloalkoxy, aryloxy, heteroaryloxy, aralkyloxy, heteroarylalkoxy, amino, nitro, cyano, carboxy, halogen, hydroxyl, sulfonyl, mercapto, alkylsulfanyl, alkylsulfimyl, alkylsulfonyl, aminocarbonyl (amido), alkylcarbonylamino, cycloalkylcarbonylamino, cycloalkylalkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, the term "alkynyl" may be understood to refer to an unsaturated aliphatic group containing a specified number of carbon atoms in either a straight-chain or branched-chain configuration and at least one triple bond. Examples include, but are not limited to, ethyne, propyne, butyne, pentyne, hexyne, and heptyne. Alkynyl groups may be substituted with one or more substituents including groups such as alkoxy, cycloalkoxy, heterocycloalkoxy, aryloxy, heteroaryloxy, aralkyloxy, heteroarylalkoxy, amino, nitro, cyano, carboxy, halogen, hydroxyl, sulfonyl, mercapto, alkylsulfanyl, alkylsulfimyl, alkylsulfonyl, aminocarbonyl (amido), alkylcarbonylamino, cycloalkylcarbonylamino, cycloalkylalkylcarbonylamino, heteroarylcarbonylamino, heteroaralkylcarbonylamino, urea, thiourea, sulfamoyl, sulfamide, alkoxycarbonyl, or alkylcarbonyloxy.

As used herein, the term "cycloalkyl" may be understood to refer to an aliphatic carbocyclic ring of 3 to 10 carbon atoms. Examples of cycloalkyl groups include, but are not limited to, cyclopropyl, cyclobutyl, cyclopentyl, cyclohexyl, cycloheptyl, cyclooctyl, adamanyl, norbornyl, octahydroindenyl, decahydronaphthyl, bicycle[3.2.1]octyl, and bicycle[2.2.2]octyl.

As used herein, the term "alkoxy" may be understood to refer to an oxygen-linked alkyl group.

As used herein, the term "heteromonocyclic" may be understood to refer to an aromatic or non-aromatic 3 to 8 atom heterocyclic ring system consisting of a single ring containing at least one heteroatom (e.g. nitrogen, oxygen, or sulfur) with the balance of the atoms in the ring consisting of carbon and/or other heteroatoms. Examples of heteromonocyclic groups include, but are not limited to, aziridine, azetidine, pyrrolidine, piperadine, piperazine, oxetane, furan, tetrahydrofuran, pyran, tetrahydropyran, pyrrole, imidazole, pyrazole, pyridine, pyridazine, pyrazine, pyrimidine, triazine, thiazole, isothiazole, oxazole, isoxazole, thiadiazole, oxadiazole, and triazole.

As used herein, the term "heterobicyclic" may be understood to refer to an aromatic or non-aromatic 7 to 12 atom heterocyclic ring system consisting of two fused rings containing at least one heteroatom (e.g. nitrogen, oxygen, or sulfur) with the balance of the atoms in the ring consisting of carbon and/or other heteroatoms. Examples of heterobicyclic groups include, but are not limited to, indole, benzimidazole, indazole, benzotriazole, benzoxazole, benzothiazole, pyrrolopyridine, pyrrolopyrimidine, pyrrolopyrazine, pyrrolopyridazine, pyrazolopyridine, pyrazolopyrimidine, pyrazolopyrazine, pyrazolopyridazine, imidazopyridine, imidazopyrimidine (purine), imidazopyrazine, imidazopyridazine, methyenedioxy benzene, triazolopyridine, triazolopyrimidine, quinoline, isoquinoline, cinnoline, phthalazine, quinazoline, quinoxaline, naphthyridine, azaquinazoline, azaquinoxaline, and azanaphthydridine.

It will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

As used herein, a "subject" refers to an animal that is the object of treatment, observation or experiment. "Animal" includes cold- and warm-blooded vertebrates and invertebrates, such as fish, shellfish, reptiles and, in particular, mammals. "Mammal" includes, without limitation, mice; rats; rabbits; guinea pigs; dogs; cats; sheep; goats; cows; horses; primates, such as monkeys, chimpanzees, apes, and prenatal, pediatric, and adult humans.

As used herein, "preventing" or "protecting" means preventing in whole or in part, or ameliorating, or controlling.

As used herein, the term "treating" refers to both therapeutic treatment and prophylactic, or preventative, measures, or administering an agent suspected of having therapeutic potential. The term includes preventative (e.g., prophylactic) and palliative treatment.

The term "a pharmaceutically effective amount", as used herein, means an amount of active compound, or pharmaceutical agent, that elicits the biological, or medicinal, response in a tissue, system, animal, or human that is being sought, which includes alleviation or palliation of the symptoms of the disease being treated and/or an amount sufficient to have utility and provide desired therapeutic endpoint. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, e.g., by assessing the time to disease progression and/or determining the response rate.

The term "pharmaceutically acceptable", as used herein, may be understood to include that the substance or composition is compatible chemically and/or toxicologically, with the other ingredients comprising a formulation, and/or the mammal being treated therewith.

The term "cancer" may be understood to include the physiological condition in mammals that is typically characterized by unregulated cell growth and/or hyperproliferative activities. A "tumor" may include one or more cancerous cells. Examples of cancer include, but are not limited to, carcinoma, lymphoma, blastoma, sarcoma, and leukemia or lymphoid malignancies. In one embodiment, the cancer is a solid tumor.

More particular examples of such cancers include breast cancer, cervical cancer, ovarian cancer, bladder cancer, endometrial or uterine carcinoma, prostate cancer, glioma and other brain or spinal cord cancers, squamous cell cancer (e.g., epithelial squamous cell cancer), lung cancer, including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, liver cancer, hepatoma, colon cancer, rectal cancer, colorectal cancer, salivary gland carcinoma, kidney or renal cancer, vulval cancer, thyroid cancer, hepatic carcinoma, anal carcinoma, penile carcinoma, as well as head and neck cancer.

For example, the following paragraphs describe some preferred embodiments of the present disclosure.

In some preferred embodiments, $R^1$ may be a hydrogen, methyl, 4-benzamido, methyl(3,5-difluorophenyl)amine, or methyl(o-fluorophenyl)amine.

Some preferred embodiments may include embodiments where $R^2$ is either hydrogen, 1-(2,2-difluoro)ethyl, or cyclobutyl.

In some embodiments, $R^3$ may be one of the following:

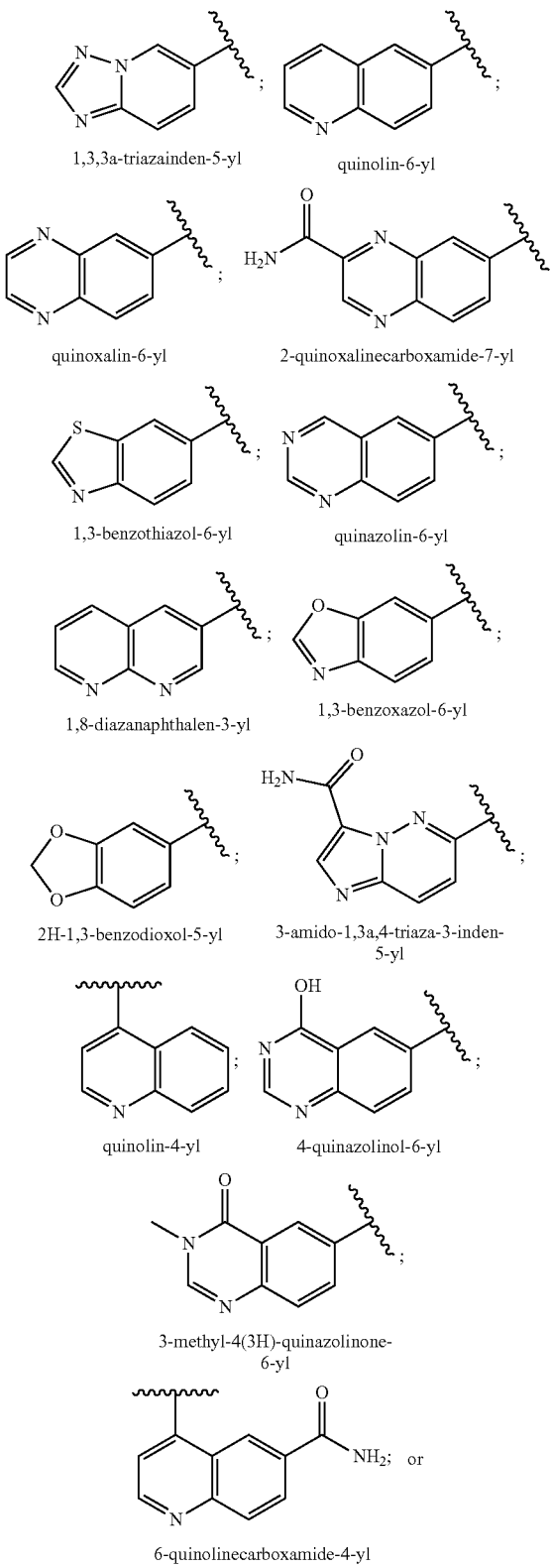

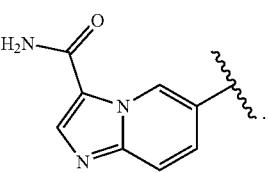

1,3a-diaza-3-indenecarboxamide-5-yl

In some embodiments, $R^4$ may be a methyl, isopropyl, cyclopropyl, difluoromethyl, or 2,2-difluoroethyl.

Specific compounds of this disclosure, including pharmaceutically acceptable salts thereof, include the following compounds (Compound 1-Compound 76).

TABLE 1

EXEMPLARY COMPOUNDS

| Compound No. | Structure and Name |
|---|---|
| 1 | N-((5-([1,2,4]triazolo[1,5-a]pyridin-6-yl)-4-(1-methyl-1H-pyrazol-3-yl)-1H-imidazol-2-yl)methyl)-2-fluoroaniline |
| 2 | N-((5-([1,2,4]triazolo[1,5-a]pyridin-6-yl)-4-(1-methyl-1H-pyrazol-3-yl)-1H-imidazol-2-yl)methyl)-2-fluoroaniline hydrochloride |

TABLE 1-continued

EXEMPLARY COMPOUNDS

| Compound No. | Structure and Name |
|---|---|
| 3 | N-((5-([1,2,4]triazolo[1,5-a]pyridin-6-yl)-4-(1-methyl-1H-pyrazol-3-yl)-1H-imidazol-2-yl)methyl)aniline |
| 4 | N-((5-([1,2,4]triazolo[1,5-a]pyridin-6-yl)-4-(1-methyl-1H-pyrazol-3-yl)-1H-imidazol-2-yl)methyl)aniline hydrochloride |
| 5 | N-((5-([1,2,4]triazolo[1,5-a]pyridin-6-yl)-4-(1-methyl-1H-pyrazol-3-yl)-1H-imidazol-2-yl)methyl)-3-fluoroaniline |
| 6 | N-((5-([1,2,4]triazolo[1,5-a]pyridin-6-yl)-4-(1-methyl-1H-pyrazol-3-yl)-1H-imidazol-2-yl)methyl)-3-fluoroaniline hydrochloride |
| 7 | N-((5-([1,2,4]triazolo[1,5-a]pyridin-6-yl)-4-(1-methyl-1H-pyrazol-3-yl)-1H-imidazol-2-yl)methyl)-4-fluoroaniline |
| 8 | N-((5-([1,2,4]triazolo[1,5-a]pyridin-6-yl)-4-(1-methyl-1H-pyrazol-3-yl)-1H-imidazol-2-yl)methyl)-4-fluoroaniline hydrochloride |

TABLE 1-continued

EXEMPLARY COMPOUNDS

| Compound No. | Structure and Name |
|---|---|
| 9 | N-((5-([1,2,4]triazolo[1,5-a]pyridin-6-yl)-4-(1-isopropyl-1H-pyrazol-3-yl)-1H-imidazol-2-yl)methyl)aniline |
| 10 | N-((5-([1,2,4]triazolo[1,5-a]pyridin-6-yl)-4-(1-isopropyl-1H-pyrazol-3-yl)-1H-imidazol-2-yl)methyl)aniline hydrochloride |
| 11 | N-((5-([1,2,4]triazolo[1,5-a]pyridin-6-yl)-4-(1-methyl-1H-pyrazol-3-yl)-1H-imidazol-2-yl)methyl)-4-chloroaniline |
| 12 | N-((5-([1,2,4]triazolo[1,5-a]pyridin-6-yl)-4-(1-methyl-1H-pyrazol-3-yl)-1H-imidazol-2-yl)methyl)-4-chloroaniline hydrochloride |
| 13 | 2-(((5-([1,2,4]triazolo[1,5-a]pyridin-6-yl)-4-(1-methyl-1H-pyrazol-3-yl)-1H-imidazol-2-yl)methyl)amino)benzonitrile |
| 14 | 2-(((5-((1,2,4]triazolo[1,5-a]pyridin-6-yl)-4-(1-methyl-1H-pyrazol-3-yl)-1H-imidazol-2-yl)methyl)amino)benzonitrile hydrochloride |

TABLE 1-continued

EXEMPLARY COMPOUNDS

| Compound No. | Structure and Name |
|---|---|
| 15 | 3-(((5-([1,2,4]triazolo[1,5-a]pyridin-6-yl)-4-(1-methyl-1H-pyrazol-3-yl)-1H-imidazol-2-yl)methyl)amino)benzonitrile |
| 16 | 3-(((5-([1,2,4]triazolo[1,5-a]pyridin-6-yl)-4-(1-methyl-1H-pyrazol-3-yl)-1H-imidazol-2-yl)methyl)amino)benzonitrile hydrochloride |
| 17 | 4-(5-([1,2,4]triazolo[1,5-a]pyridin-6-yl)-4-(1-isopropyl-1H-pyrazol-3-yl)-1H-imidazol-2-yl)benzamide |
| 18 | 3-(((5-([1,2,4]triazolo[1,5-a]pyridin-6-yl)-4-(1-methyl-1H-pyrazol-3-yl)-1H-imidazol-2-yl)methyl)amino)benzamide |
| 19 | N-((5-([1,2,4]triazolo[1,5-a]pyridin-6-yl)-4-(1-isopropyl-1H-pyrazol-3-yl)-1H-imidazol-2-yl)methyl)-3-fluoroaniline |
| 20 | N-((5-([1,2,4]triazolo[1,5-a]pyridin-6-yl)-4-(1-isopropyl-1H-pyrazol-3-yl)-1H-imidazol-2-yl)methyl)-3-fluoroaniline hydrochloride |

TABLE 1-continued

EXEMPLARY COMPOUNDS

| Compound No. | Structure and Name |
|---|---|
| 21 | 3-fluoro-N-((4-(1-isopropyl-1H-pyrazol-3-yl)-5-(quinoxalin-6-yl)-1H-imidazol-2-yl)methyl)aniline |
| 22 | 3-fluoro-N-((4-(1-isopropyl-1H-pyrazol-3-yl)-5-(quinoxalin-6-yl)-1H-imidazol-2-yl)methyl)aniline hydrochloride |
| 23 | 3-fluoro-N-((4-(1-methyl-1H-pyrazol-3-yl)-5-(quinolin-6-yl)-1H-imidazol-2-yl)methyl)aniline |
| 24 | 3-fluoro-N-((4-(1-methyl-1H-pyrazol-3-yl)-5-(quinolin-6-yl)-1H-imidazol-2-yl)methyl)aniline hydrochloride |
| 25 | 3-fluoro-N-((4-(1-isopropyl-1H-pyrazol-3-yl)-5-(quinolin-6-yl)-1H-imidazol-2-yl)methyl)aniline |
| 26 | 3-fluoro-N-((4-(1-isopropyl-1H-pyrazol-3-yl)-5-(quinolin-6-yl)-1H-imidazol-2-yl)methyl)aniline hydrochloride |

TABLE 1-continued

EXEMPLARY COMPOUNDS

| Compound No. | Structure and Name |
|---|---|
| 27 | 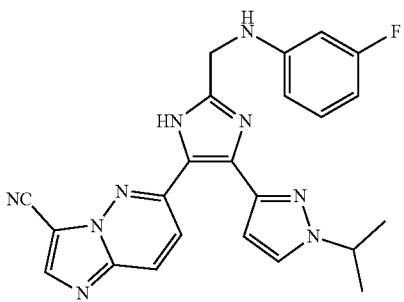 [SMILES: CC(C)n1ccc(-c2nc(CNc3cccc(F)c3)[nH]c2-c2ccc3ncc(C#N)n3n2)n1] 6-(2-(((3-fluorophenyl)amino)methyl)-4-(1-isopropyl-1H-pyrazol-3-yl)-1H-imidazol-5-yl)imidazo[1,2-b]pyridazine-3-carbonitrile |
| 28 | 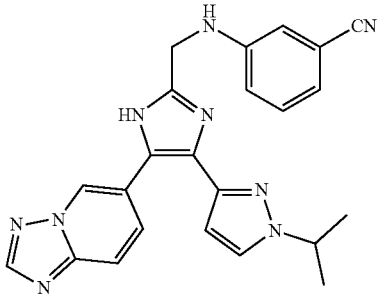 [SMILES: CC(C)n1ccc(-c2nc(CNc3cccc(C#N)c3)[nH]c2-c2ccc3ncnn3c2)n1] 3-(((5-([1,2,4]triazolo[1,5-a]pyridin-6-yl)-4-(1-isopropyl-1H-pyrazol-3-yl)-1H-imidazol-2-yl)methyl)amino)benzonitrile |
| 29 | 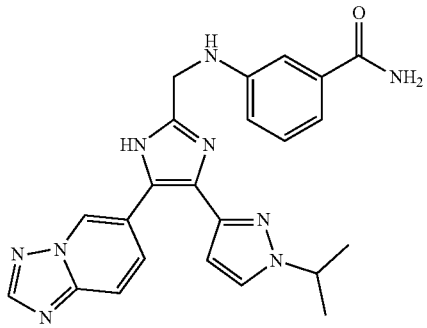 [SMILES: CC(C)n1ccc(-c2nc(CNc3cccc(C(N)=O)c3)[nH]c2-c2ccc3ncnn3c2)n1] 3-(((5-([1,2,4]triazolo[1,5-a]pyridin-6-yl)-4-(1-isopropyl-1H-pyrazol-3-yl)-1H-imidazol-2-yl)methyl)amino)benamide |
| 30 | 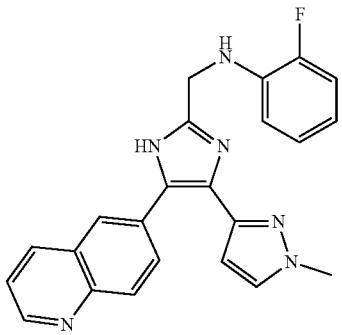 [SMILES: Cn1ccc(-c2nc(CNc3ccccc3F)[nH]c2-c2ccc3ncccc3c2)n1] 2-fluoro-N-((4-(1-methyl-1H-pyrazol-3-yl)-5-(quinolin-6-yl)-1H-imidazol-2-yl)methyl)aniline |
| 31 | 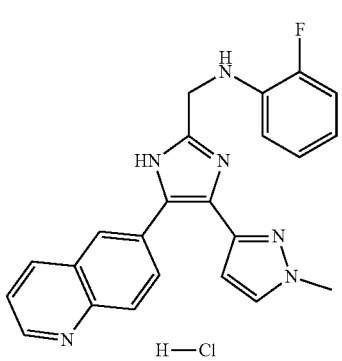 2-fluoro-N-((4-(1-methyl-1H-pyrazol-3-yl)-5-(quinolin-6-yl)-1H-imidazol-2-yl)methyl)aniline hydrochloride |
| 32 | 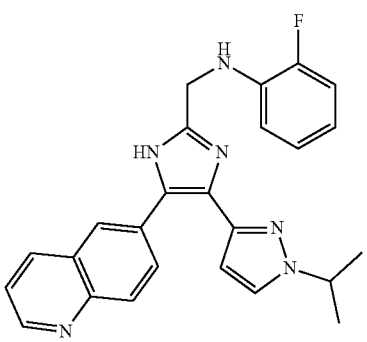 [SMILES: CC(C)n1ccc(-c2nc(CNc3ccccc3F)[nH]c2-c2ccc3ncccc3c2)n1] 2-fluoro-N-((4-(1-isopropyl-1H-pyrazol-3-yl)-5-(quinolin-6-yl)-1H-imidazol-2-yl)methyl)aniline |

TABLE 1-continued

EXEMPLARY COMPOUNDS

| Compound No. | Structure and Name |
|---|---|
| 33 | 2-fluoro-N-((4-(1-isopropyl-1H-pyrazol-3-yl)-5-(quinolin-6-yl)-1H-imidazol-2-yl)methyl)aniline hydrochloride |
| 34 | 6-(2-(((3-fluorophenyl)amino)methyl)-4-(1-isopropyl-1H-pyrazol-3-yl)-1H-imidazol-5-yl)imidazo[1,2-b]pyridazine-3-carboxamide |
| 35 | N-((5-([1,2,4]triazolo[1,5-a]pyridin-6-yl)-4-(1-isopropyl-1H-pyrazol-3-yl)-1H-imidazol-2-yl)methyl)-3,5-difluoroaniline |
| 36 | N-((5-([1,2,4]triazolo[1,5-a]pyridin-6-yl)-4-(1-isopropyl-1H-pyrazol-3-yl)-1H-imidazol-2-yl)methyl)-3,5-difluoroaniline hydrochloride |
| 37 | 4-(5-(benzo[d]thiazol-6-yl)-4-(1-methyl-1H-pyrazol-3-yl)-1H-imidazol-2-yl)benzamide |
| 38 | 6-(2-(((3-cyanophenyl)amino)methyl)-4-(1-isopropyl-1H-pyrazol-3-yl)-1H-imidazol-5-yl)imidazo[1,2-b]pyridazine-3-carboxamide |

TABLE 1-continued

EXEMPLARY COMPOUNDS

| Compound No. | Structure and Name |
|---|---|
| 39 | 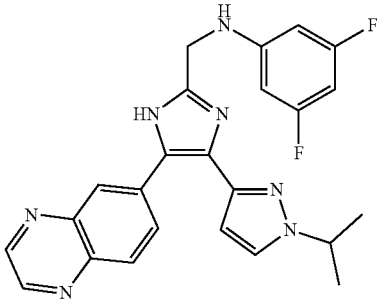 [SMILES: CC(C)n1ccc(-c2nc(CNc3cc(F)cc(F)c3)[nH]c2-c2ccc3nccnc3c2)n1]
3,5-difluoro-N-((4-(1-isopropyl-1H-pyrazol-3-yl)-5-(quinoxalin-6-yl)-1H-imidazol-2-yl)methyl)aniline |
| 40 | 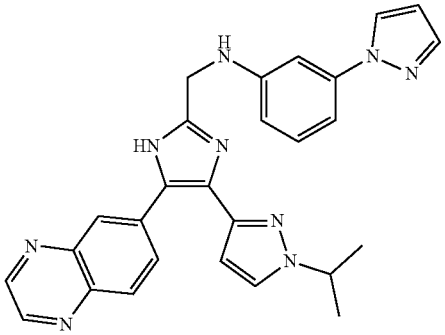 [SMILES: CC(C)n1ccc(-c2nc(CNc3cccc(-n4cccn4)c3)[nH]c2-c2ccc3nccnc3c2)n1]
N-((4-(1-isopropyl-1H-pyrazol-3-yl)-5-(quinoxalin-6-yl)-1H-imidazol-2-yl)methyl)-3-(1H-pyrazol-1-yl)aniline |
| 41 | 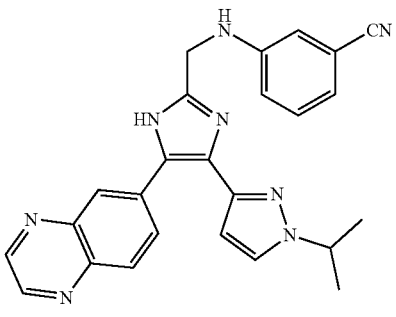 [SMILES: CC(C)n1ccc(-c2nc(CNc3cccc(C#N)c3)[nH]c2-c2ccc3nccnc3c2)n1]
3-(((4-(1-isopropyl-1H-pyrazol-3-yl)-5-(quinoxalin-6-yl)-1H-imidazol-2-yl)methyl)amino)benzonitrile |
| 42 | 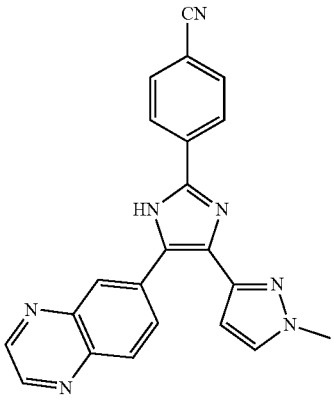 [SMILES: Cn1ccc(-c2nc(-c3ccc(C#N)cc3)[nH]c2-c2ccc3nccnc3c2)n1]
4-(4-(1-methyl-1H-pyrazol-3-yl)-5-(quinoxalin-6-yl)-1H-imidazol-2-yl)benzonitrile |
| 43 | 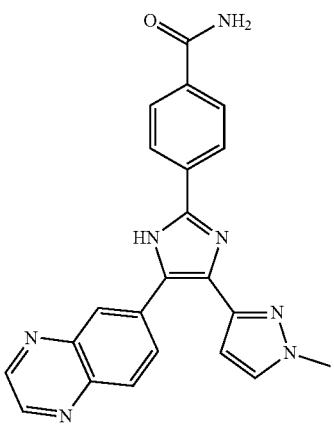 [SMILES: Cn1ccc(-c2nc(-c3ccc(C(N)=O)cc3)[nH]c2-c2ccc3nccnc3c2)n1]
4-(4-(1-methyl-1H-pyrazol-3-yl)-5-(quinoxalin-6-yl)-1H-imidazol-2-yl)benzamide |
| 44 | 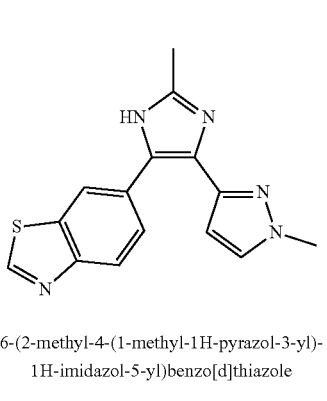
6-(2-methyl-4-(1-methyl-1H-pyrazol-3-yl)-1H-imidazol-5-yl)benzo[d]thiazole |

TABLE 1-continued

EXEMPLARY COMPOUNDS

| Compound No. | Structure and Name |
|---|---|
| 45 | 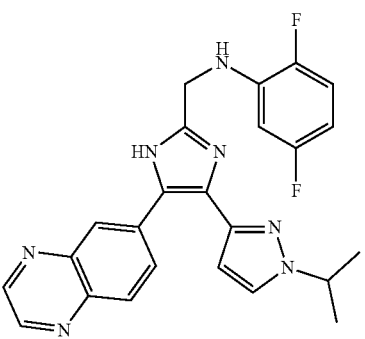 [SMILES: CC(C)n1ccc(-c2nc(CNc3cc(F)ccc3F)[nH]c2-c2ccc3nccnc3c2)n1]<br>2,5-difluoro-N-((4-(1-isopropyl-1H-pyrazol-3-yl)-5-(quinoxalin-6-yl)-1H-imidazol-2-yl)methyl)aniline |
| 46 | 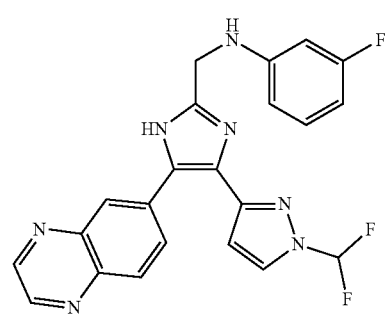<br>N-((4-(1-(difluoromethyl)-1H-pyrazol-3-yl)-5-(quinoxalin-6-yl)-1H-imidazol-2-yl)methyl)-3-fluoroaniline |
| 47 | 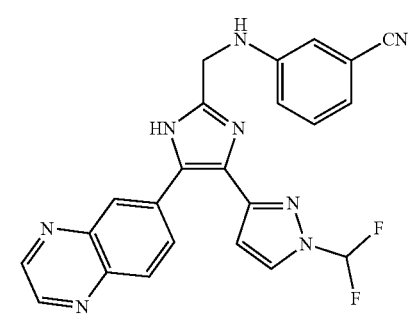<br>3-(((4-(1-(difluoromethyl)-1H-pyrazol-3-yl)-5-(quinoxalin-6-yl)-1H-imidazol-2-yl)methyl)amino)benzonitrile |
| 48 | 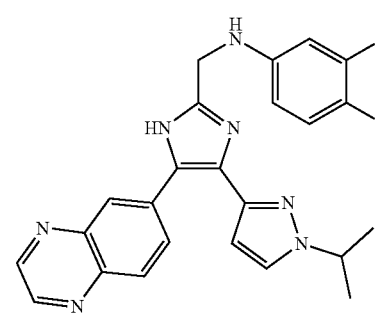<br>3,4-difluoro-N-((4-(1-isopropyl-1H-pyrazol-3-yl)-5-(quinoxalin-6-yl)-1H-imidazol-2-yl)methyl)aniline |
| 49 | 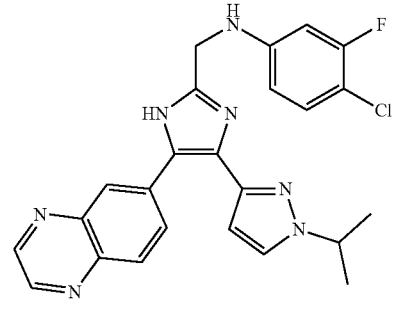 [SMILES: CC(C)n1ccc(-c2nc(CNc3ccc(Cl)c(F)c3)[nH]c2-c2ccc3nccnc3c2)n1]<br>4-chloro-3-fluoro-N-((4-(1-isopropyl-1H-pyrazol-3-yl)-5-(quinoxalin-6-yl)-1H-imidazol-2-yl)methyl)aniline |
| 50 | 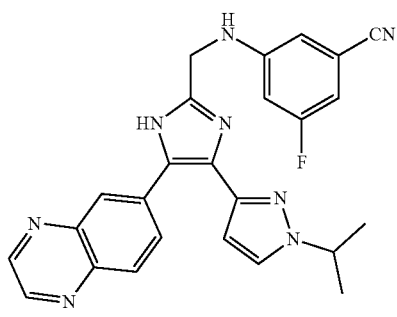 [SMILES: CC(C)n1ccc(-c2nc(CNc3cc(F)cc(C#N)c3)[nH]c2-c2ccc3nccnc3c2)n1]<br>3-fluoro-5-(((4-(1-isopropyl-1H-pyrazol-3-yl)-5-(quinoxalin-6-yl)-1H-imidazol-2-yl)methyl)amino)benzonitrile |

TABLE 1-continued

EXEMPLARY COMPOUNDS

| Compound No. | Structure and Name |
|---|---|
| 51 | 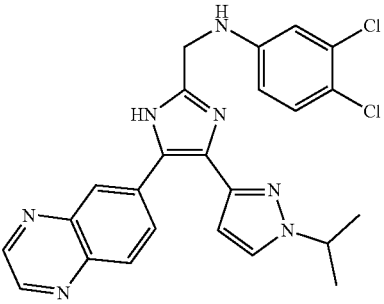 [SMILES: CC(C)n1ccc(-c2nc(CNc3ccc(Cl)c(Cl)c3)[nH]c2-c2ccc3nccnc3c2)n1]<br>3,4-dichloro-N-((4-(1-isopropyl-1H-pyrazol-3-yl)-5-(quinoxalin-6-yl)-1H-imidazol-2-yl)methyl)aniline |
| 52 | 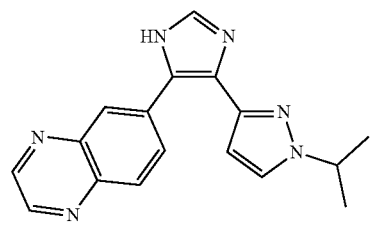 [SMILES: CC(C)n1ccc(-c2nc[nH]c2-c2ccc3nccnc3c2)n1]<br>6-(4-(1-isopropyl-1H-pyrazol-3-yl)-1H-imidazol-5-yl)quinoxaline |
| 53 | 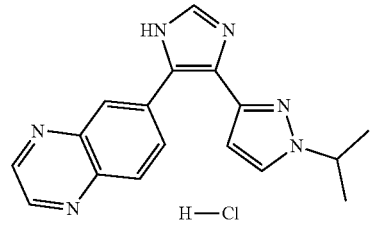<br>6-(4-(1-isopropyl-1H-pyrazol-3-yl)-1H-imidazol-5-yl)quinoxaline hydrochloride |
| 54 | 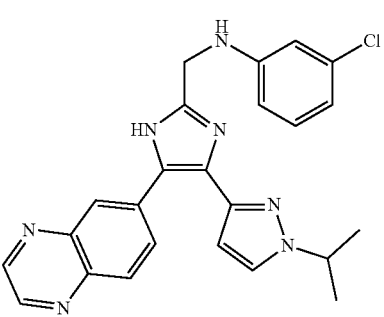 [SMILES: CC(C)n1ccc(-c2nc(CNc3cccc(Cl)c3)[nH]c2-c2ccc3nccnc3c2)n1]<br>3-chloro-N-((4-(1-isopropyl-1H-pyrazol-3-yl)-5-(quinoxalin-6-yl)-1H-imidazol-2-yl)methyl)aniline |
| 55 | 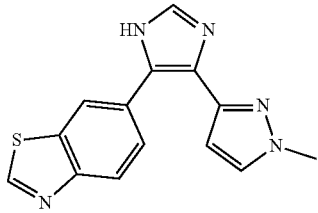 [SMILES: Cn1ccc(-c2nc[nH]c2-c2ccc3ncsc3c2)n1]<br>6-(4-(1-methyl-1H-pyrazol-3-yl)-1H-imidazol-5-yl)benzo[d]thiazole |
| 56 | 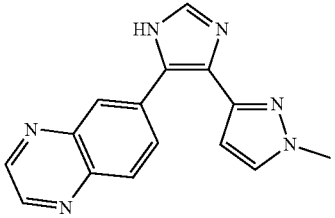 [SMILES: Cn1ccc(-c2nc[nH]c2-c2ccc3nccnc3c2)n1]<br>6-(4-(1-methyl-1H-pyrazol-3-yl)-1H-imidazol-5-yl)quinoxaline |
| 57 | 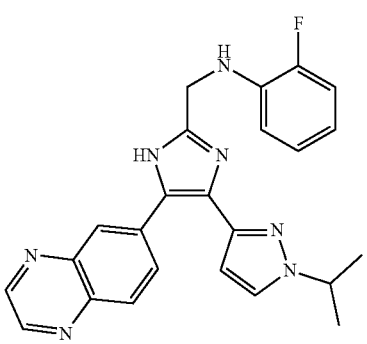 [SMILES: CC(C)n1ccc(-c2nc(CNc3ccccc3F)[nH]c2-c2ccc3nccnc3c2)n1]<br>2-fluoro-N-((4-(1-isopropyl-1H-pyrazol-3-yl)-5-(quinoxalin-6-yl)-1H-imidazol-2-yl)methyl)aniline |
| 58 | 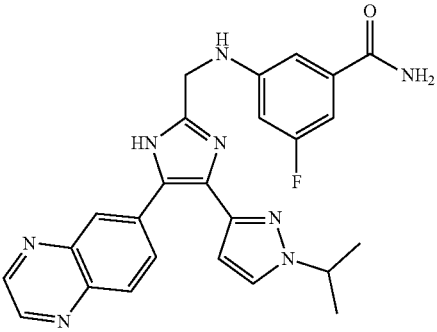 [SMILES: CC(C)n1ccc(-c2nc(CNc3cc(F)cc(C(N)=O)c3)[nH]c2-c2ccc3nccnc3c2)n1]<br>3-fluoro-5-(((4-(1-isopropyl-1H-pyrazol-3-yl)-5-(quinoxalin-6-yl)-1H-imidazol-2-yl)methyl)amino)benzamide z |

TABLE 1-continued

EXEMPLARY COMPOUNDS

| Compound No. | Structure and Name |
|---|---|
| 59 | 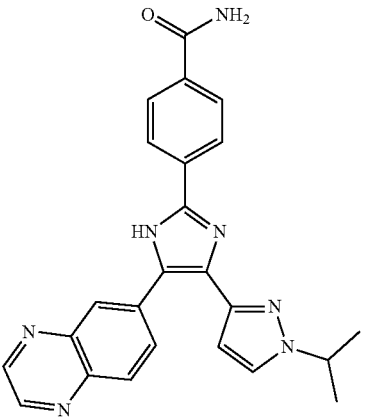 [SMILES: CC(C)n1ccc(-c2nc(-c3ccc(C(N)=O)cc3)[nH]c2-c2ccc3nccnc3c2)n1]<br>4-(4-(1-isopropyl-1H-pyrazol-3-yl)-5-(quinoxalin-6-yl)-1H-imidazol-2-yl)benzamide |
| 60 | 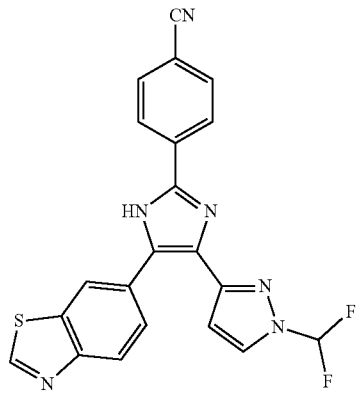 [SMILES: N#Cc1ccc(-c2nc(-c3ccn(C(F)F)n3)c(-c3ccc4ncsc4c3)[nH]2)cc1]<br>4-(5-(benzo[d]thiazol-6-yl)-4-(1-(difluoromethyl)-1H-pyrazol-3-yl)-1H-imidazol-2-yl)benzonitrile |
| 61 | 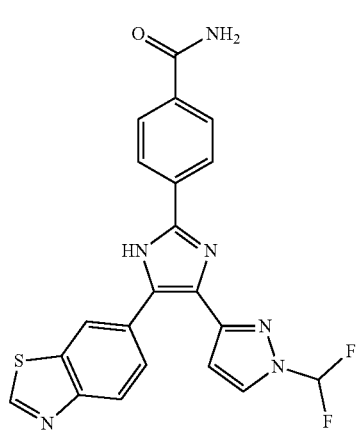 [SMILES: NC(=O)c1ccc(-c2nc(-c3ccn(C(F)F)n3)c(-c3ccc4ncsc4c3)[nH]2)cc1]<br>4-(5-(benzo[d]thiazol-6-yl)-4-(1-(difluoromethyl)-1H-pyrazol-3-yl)-1H-imidazol-2-yl)benzamide |
| 62 | 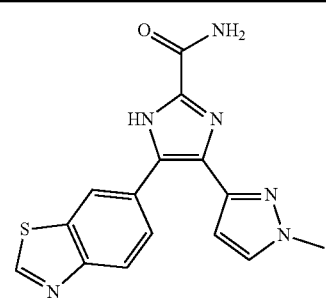<br>5-(benzo[d]thiazol-6-yl)-4-(1-methyl-1H-pyrazol-3-yl)-1H-imidazole-2-carboxamide |
| 63 | 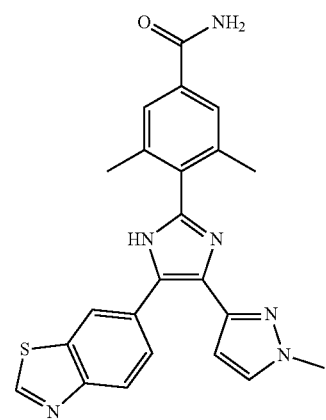 [SMILES: Cc1cc(C(N)=O)cc(C)c1-c1nc(-c2ccn(C)n2)c(-c2ccc3ncsc3c2)[nH]1]<br>4-(5-(benzo[d]thiazol-6-yl)-4-(1-methyl-1H-pyrazol-3-yl)-1H-imidazol-2-yl)-3,5-dimethylbenzamide |
| 64 | 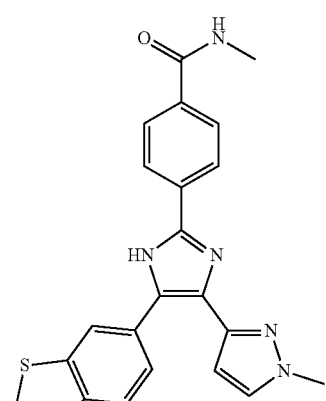<br>4-(5-(benzo[d]thiazol-6-yl)-4-(1-methyl-1H-pyrazol-3-yl)-1H-imidazol-2-yl)-N-methylbenzamide |

TABLE 1-continued

EXEMPLARY COMPOUNDS

| Compound No. | Structure and Name |
|---|---|
| 65 | 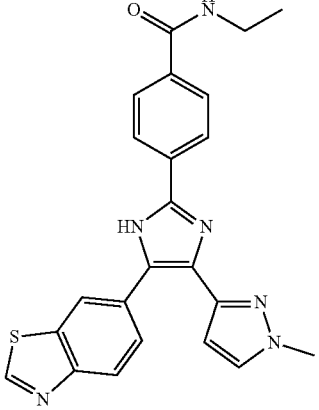<br>4-(5-(benzo[d]thiazol-6-yl)-4-(1-methyl-1H-pyrazol-3-yl)-1H-imidazol-2-yl)-N-ethylbenzamide |
| 66 | 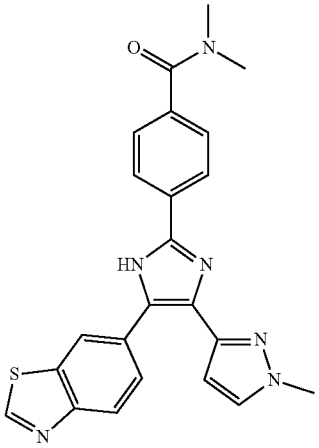 [SMILES: CN(C)C(=O)c1ccc(-c2nc(-c3ccn(C)n3)c(-c3ccc4ncsc4c3)[nH]2)cc1]<br>4-(5-(benzo[d]thiazol-6-yl)-4-(1-methyl-1H-pyrazol-3-yl)-1H-imidazol-2-yl)-N,N-dimethylbenzamide |
| 67 | 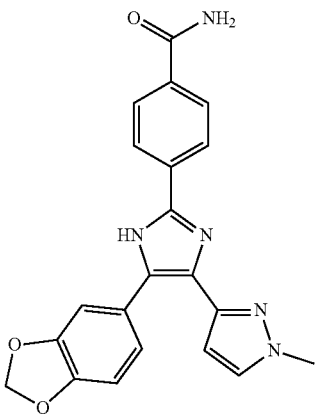 [SMILES: Cn1ccc(-c2nc(-c3ccc(C(N)=O)cc3)[nH]c2-c2ccc3c(c2)OCO3)n1]<br>4-(5-(benzo[d][1,3]dioxol-5-yl)-4-(1-methyl-1H-pyrazol-3-yl)-1H-imidazol-2-yl)benzamide |
| 68 | 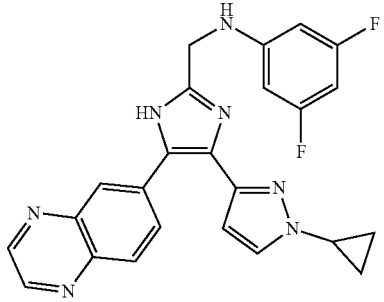 [SMILES: Fc1cc(F)cc(NCc2nc(-c3ccn(C4CC4)n3)c(-c3ccc4nccnc4c3)[nH]2)c1]<br>N-((4-(1-cyclopropyl-1H-pyrazol-3-yl)-5-(quinoxalin-6-yl)-1H-imidazol-2-yl)methyl)-3,5-difluoroaniline |
| 69 | 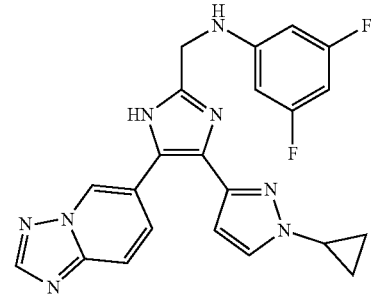 [SMILES: Fc1cc(F)cc(NCc2nc(-c3ccn(C4CC4)n3)c(-c3ccc4ncnn4c3)[nH]2)c1]<br>N-((5-([1,2,4]triazolo[1,5-a]pyridin-6-yl)-4-(1-cyclopropyl-1H-pyrazol-3-yl)-1H-imidazol-2-yl)methyl)-3,5-difluoroaniline |
| 70 | 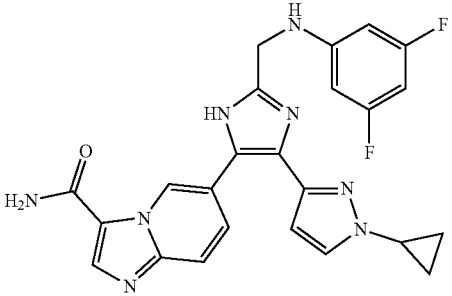 [SMILES: NC(=O)c1cnc2ccc(-c3[nH]c(CNc4cc(F)cc(F)c4)nc3-c3ccn(C4CC4)n3)cn12]<br>6-(4-(1-cyclopropyl-1H-pyrazol-3-yl)-2-(((3,5-difluorophenyl)amino)methyl)-1H-imidazol-5-yl)imidazo[1,2-a]pyridine-3-carboxamide |

TABLE 1-continued

EXEMPLARY COMPOUNDS

| Compound No. | Structure and Name |
|---|---|
| 71 | 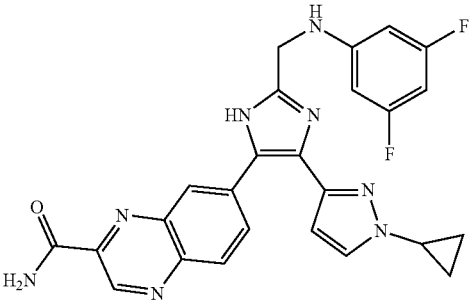 [SMILES: NC(=O)c1cnc2ccc(-c3[nH]c(CNc4cc(F)cc(F)c4)nc3-c3ccn(C4CC4)n3)cc2n1]<br>7-(4-(1-cyclopropyl-1H-pyrazol-3-yl)-2-(((3,5-difluorophenyl)amino)methyl)-1H-imidazol-5-yl)quinoxaline-2-carboxamide |
| 72 | 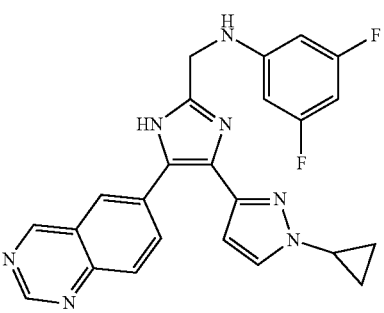 [SMILES: Fc1cc(F)cc(NCc2nc(-c3ccn(C4CC4)n3)c(-c3ccc4ncncc4c3)[nH]2)c1]<br>N-((4-(1-cyclopropyl-1H-pyrazol-3-yl)-5-(quinazolin-6-yl)-1H-imidazol-2-yl)methyl)-3,5-difluoroaniline |
| 73 | 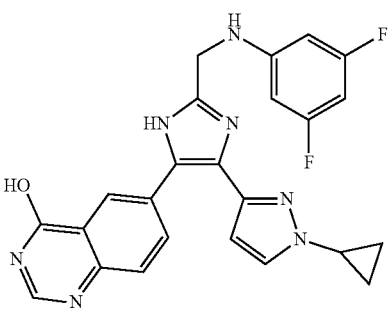 [SMILES: Oc1ncnc2ccc(-c3[nH]c(CNc4cc(F)cc(F)c4)nc3-c3ccn(C4CC4)n3)cc12]<br>6-(4-(1-cyclopropyl-1H-pyrazol-3-yl)-2-(((3,5-difluorophenyl)amino)methyl)-1H-imidazol-5-yl)quinazolin-4-ol |
| 74 | 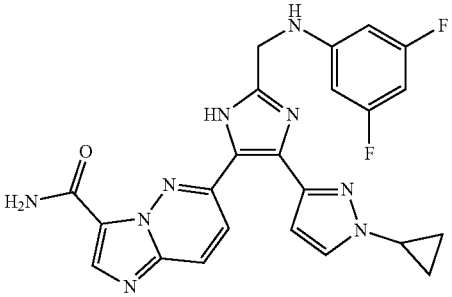<br>6-(4-(1-cyclopropyl-1H-pyrazol-3-yl)-2-(((3,5-difluorophenyl)amino)methyl)-1H-imidazol-5-yl)imidazo[1,2-b]pyridazine-3-carboxamide |
| 75 | 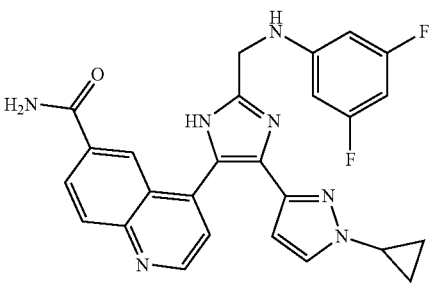 [SMILES: NC(=O)c1ccc2nccc(-c3[nH]c(CNc4cc(F)cc(F)c4)nc3-c3ccn(C4CC4)n3)c2c1]<br>4-(4-(1-cyclopropyl-1H-pyrazol-3-yl)-2-(((3,5-difluorophenyl)amino)methyl)-1H-imidazol-5-yl)quinoline-6-carboxamide |
| 76 | 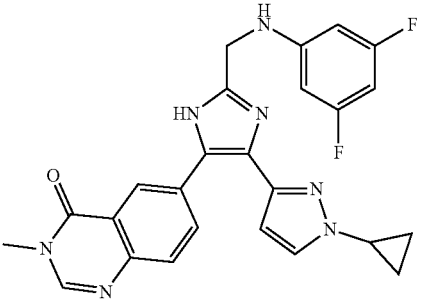 [SMILES: Cn1cnc2ccc(-c3[nH]c(CNc4cc(F)cc(F)c4)nc3-c3ccn(C4CC4)n3)cc2c1=O]<br>6-(4-(1-cyclopropyl-1H-pyrazol-3-yl)-2-(((3,5-difluorophenyl)amino)methyl)-1H-imidazol-5-yl)-3-methylquinazolin-4(3H)-one |

It will be recognized by one skilled in the art that basic nitrogen atoms present in the compounds disclosed herein may be combined with organic or inorganic acids resulting in the formation of salts. Some embodiments encompass an ALK5 inhibitor, as described above, wherein a derivative or a pharmaceutically acceptable salt thereof as the active biological agent. In addition, solvates comprised of either organic or inorganic solvents may also be prepared and found to be pharmaceutically acceptable or even preferable. Many of the compounds disclosed herein, whether as salts or free bases, may exist in one or more crystalline forms. Such polymorphic forms may have differing properties regarding, but not limited to, absorption, solubility, and stability, one or more of which may be pharmaceutically acceptable or even preferable.

In the case of ALK5 inhibitors that are to be administered orally, blending of the active ingredient with pharmaceutically acceptable carriers (e.g. excipients, disintegrants, binders, colorants, flavorings, emulsifiers, coatings, etc.), diluents, or solubilizing agents may provide a finished pharmaceutical product in the form of tablets, granules, powders, capsules, suspensions, syrups, or solutions, some of which may be designed for either quick release or timed release of the active drug agent. Similar or different formulations may be used for compounds specified for delivery via an intravenous, pulmonary, intramuscular route, or via suppository. One skilled in the art—with the aid of this disclosure—will also appreciate that drug compounds disclosed herein may be derivatized as prodrugs designed to release the active ingredient in the GI system or in plasma. Thus, such prodrug derivatives are within the scope of this disclosure.

It will also be understood by skilled practitioners of the art that the scope of the compounds or synthetic intermediates embodied in the formula above may include molecules containing chiral centers. The present disclosure includes embodiments where such compounds are present in the form of enantiomers, diastereomers, meso structures, or racemic mixtures.

Generally, it is preferred in some embodiments that compounds disclosed herein, if they are comprised of enantiomers or diastereomers with one or more chiral centers, the preferred compound will be used as a single enantiomer or diastereomer. Single enantiomers or diastereomers may be prepared by using enantiomerically or diasteromerically pure starting reagents, or by the use of synthetic transformations known to provide control of chirality. Alternatively, racemic or diastereomeric mixtures may be resolved into enantiomerically or diasteromerically pure components through the use of standard chiral separation and/or crystallization techniques.

Also included in the scope of this disclosure are radiolabeled isomers or derivatives of the compounds of the formula described above that may be suitable for various in vivo biological studies.

One skilled in the art may prepare compounds of the invention by any of a number of known synthetic methods beginning with starting materials available from a commercial source or synthesized from simpler available molecules.

The following six reaction schemes are provided as various examples for synthesizing various embodiments of the compounds of the invention. Some compounds of the disclosure may be synthesized, as described below, where $R^2$ and $R^4$ are as defined above.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labeled compounds are useful in metabolic studies (for example with $^{14}C$), reaction kinetic studies (with, for example $^2H$ or $^3H$), detection or imagine techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly suitable for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically related reagent. Deuteration is particularly appropriate for compounds containing methyl or methylene groups Table 2, below, describes the results of assays carried out on some compounds of the invention. Exemplified compounds were confirmed to inhibit ALK5 activity in enzyme and cellular assays in the following assay systems conducted by ThermoFisher in Madison, WI according to their commercially available protocols.

ThermoFisher SelectScreen™ Biochemical Kinase Profiling Service, LanthaScreen™ Eu Kinase Binding Assay TGFBR1 (ALK5)

Exemplified compounds were screened in 1% DMSO (final concentration) by 3-fold serial dilutions from 10,000 nM to 0.316 nM to produce an $IC_{50}$ or at single concentrations of 10,000, 1000 and 100 nM according to the following protocol. To low volume, white 384-well plates (Greiner Cat #784207) add 160 nL 100× compound in 100% DMSO, 3.84 uL kinase buffer (50 mM HEPES, pH 7.5, 0.01% BRIJ-35, 10 mM $MgCl_2$, 1 mM EGTA), 8 uL 2× kinase/antibody mixture in kinase buffer (final ALK5 concentration of 5 nM; final Eu-anti-GST antibody concentration of 2 nM), 4 uL 4× Tracer #178 in kinase buffer (final concentration of 5 nM). Gently shake the plates for 30 seconds and incubate at room temperature for 1 hour before reading fluorescence on a plate reader. Percent inhibition was determined compared to DMSO only control (maximal ALK5 tracer binding) and sigmoidal dose response curve fit yielded $IC_{50}$ values as indicated in Table 2. For those compounds marked with an asterisk, activity was evaluated at three concentrations (10000, 1000, 10 nM) and the $IC_{50}$ is depicted as less than the lowest concentration producing >50% inhibition.

ThermoFisher SelectScreen™ Cell-Based Pathway Profiling Service GeneBLAzer Beta-Lactamase (Bla) Reporter Technology—TGF-Beta 1 Stimulated SBE-Bla HEK 293T Cell-Based Assay SBE-bla HEK 293T cells were thawed and re-suspended in Assay Media (OPTI-MEM, 0.5% dialyzed FBS 0.1 mM NEAA, 1 mM Sodium Pyruvate, 100 U/mL/100 μg/mL Pen/Strep) to a concentration of 625,000 cells/mL. 32 μL of cell suspension (20,000 cells) was added to each well of a 384-well Poly-D-Lysine assay plate. Cells in Assay Media were incubated for 16-24 hours in the plate at 37° C./5% $CO_2$ in a humidified incubator. 4 μL of a 10× serial dilution of ALK5 inhibitors (10×=100,000-3.16 nM) was added to appropriate wells of the plate and pre-incubated at 37° C./5% $CO_2$ in a humidified incubator with cells for 30 minutes. Final concentration of inhibitor ranged from 10,000 nM to 0.316 nM. 4 μL of 10× TGF-beta 1 (final concentration of 0.03 nM) was added to wells containing the inhibitors. The plate was incubated for 5 hours at 37° C./5% $CO_2$ in a humidified incubator. 8 μL of 1 μM Substrate Loading Solution was added to each well and the plate was incubated for 2 hours at room temperature before being read on a fluorescence plate reader. Percent inhibition was determined compared to DMSO only control (maximal TGF-beta 1 stimulation) and sigmoidal dose response curve fit yielded $IC_{50}$ values as indicated in Table 2. For those compounds marked with an asterisk, activity was evaluated at three concentrations (10000, 1000, and 100) nM) and the IC$_{50}$ is depicted as less than the lowest concentration producing greater than 50% inhibition.

TABLE 2

Biological activity assay results

| Compound No. | Cells (SBE_HEK293T) IC50 (nM) | TβRI (ALK5) Binding IC50 (nM) |
|---|---|---|
| 2 | >10000 | 1370 |
| 4 | >10000 | 1370 |
| 6 | 3870 | 354 |
| 8 | >10000 | 811 |
| 10 | 2665 | 264 |
| 12 | >10000 | — |
| 14 | >10000 | — |
| 16* | 3570 | <1000 |
| 17* | — | <1000 |
| 20* | 1270 | <100 |
| 22* | 1090 | <100 |
| 24* | 1930 | <200 |
| 26* | — | <100 |
| 27* | — | <100 |
| 28* | 757 | <100 |
| 29* | 4620 | <100 |
| 31* | 8930 | <1000 |
| 33* | 9120 | <200 |
| 34 | 379 | 49 |
| 36 | 507 | 103 |
| 37 | 53.2 | 5.6 |
| 38* | 3180 | <100 |
| 39 | 53.6 | 46.4 |
| 40* | 1050 | <100 |
| 41 | 77.5 | 33 |
| 42* | — | <100 |
| 43* | 485 | <100 |
| 44 | 37.4 | 6.66 |
| 45* | 323 | <100 |
| 46 | 11.6 | 5.6 |
| 47 | 19.5 | 6.6 |
| 48* | — | <100 |
| 49* | — | <1000 |
| 50 | 1070 | 138 |
| 51 | — | 260 |
| 53* | — | <1000 |
| 54 | 211 | 31.2 |
| 55 | 132 | 4.71 |
| 56 | 1050 | 43.6 |
| 57 | 2190 | 128 |
| 58 | 3920 | 78 |
| 59 | — | 889 |
| 60 | — | 71.7 |
| 61 | 65.3 | 7.55 |
| 62 | 1130 | 45.8 |
| 63 | 3030 | 399 |
| 64 | 632 | 44.6 |
| 65 | 654 | 46.2 |
| 66 | 1360 | 285 |
| 67 | — | 50 |
| 68 | 10.9 | 1.2 |
| 69 | — | 3 |

Scheme 1

In Scheme 1 illustrated below, compound (I), which is a subset of the compounds of the invention, where substituent R$^{11}$ may be a halogen, alkyl group, etc. as defined by R$^1$ above, may be prepared beginning with an ester of structure (II), where R$^{10}$=alkyl (most typically methyl or ethyl). Ester (II) may be reacted with acetal (III) in a suitable solvent to provide amidine (IV), which may then be reacted with hydroxylamine, followed by trifluoroacetic acid anhydride and then sodium bicarbonate, to provide ester (V). Ester (V) may be converted to its corresponding Weinreb amide (VI) by hydrolysis to the corresponding carboxylic acid, treatment with thionyl chloride, and reaction of the resultant acid chloride with methoxymethylamine. Reaction of amide (VI) with Grignard reagent (VIII), derived in turn from the reaction of magnesium metal with halopyrazole (VII), provides ketone (IX). In various embodiments, the halogen of (VII) may be either chloro, bromo, or iodo. Oxidation of (IX) with hydrobromic acid in dimethyl sulfoxide (DMSO) produces diketone (X). Other oxidizing reagents to affect this conversion include selenium dioxide or nitric acid.

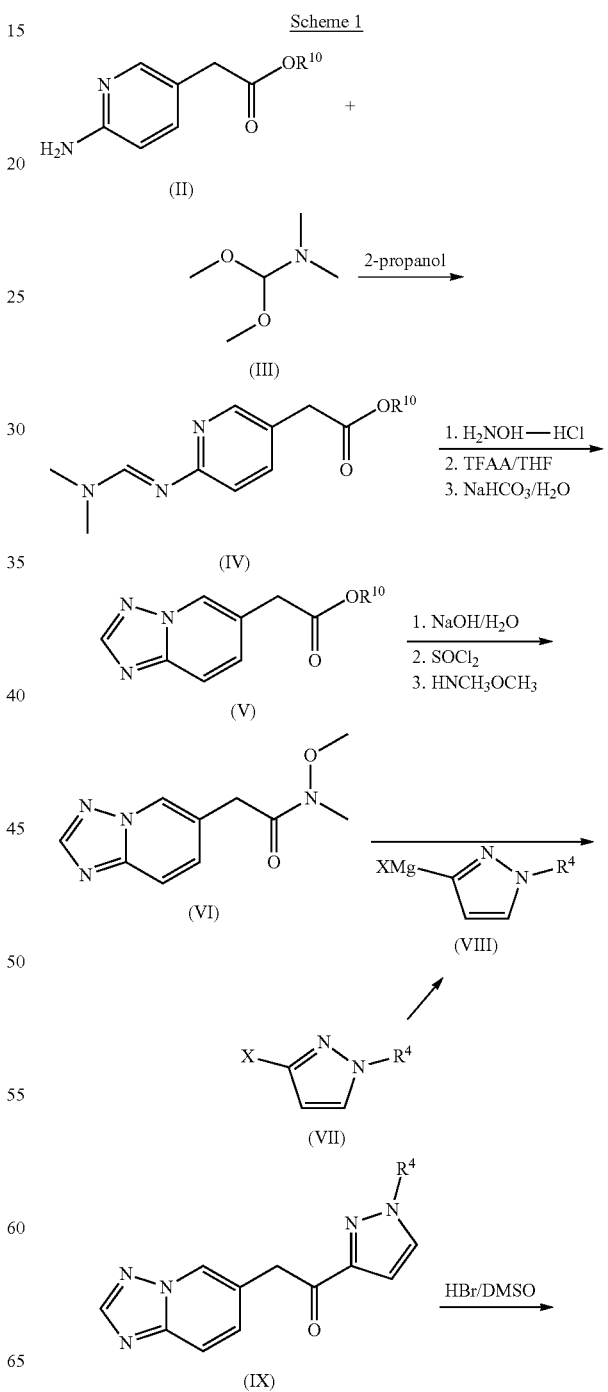

Scheme 1

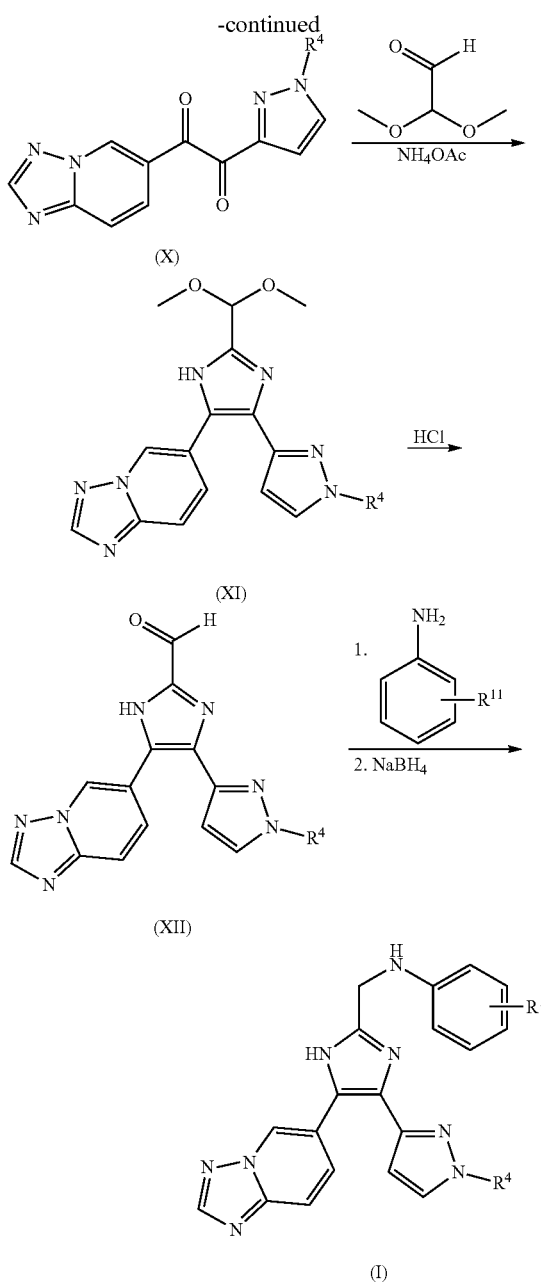

Scheme 2

Another method of making intermediate (X) is shown in Scheme 2 and begins with the Sonogashira palladium-catalyzed coupling of 5-iodo-1,3,3a-triazaindene (XIII) with trimethylsilylacetylene, followed by de-silylation with potassium carbonate to provide alkyne (XIV). A second Sonogashira coupling with iodopyrazole (XV) then gives alkyne (XVI), which upon treatment with potassium permanganate followed by sodium nitrite in sulfuric acid, provides intermediate diketone (X). In Scheme 1, the condensation of (X) with glyoxal dimethyl acetal provides acetal (XI), which upon treatment with a suitable aqueous acid such as hydrochloric acid provides the aldehyde (XII). Reductive amination with an appropriate substituted aniline followed by treatment with a reducing agent such as sodium borohydride gives compound (I). One skilled in the art will appreciate that the intermediate aldehyde (XII) represents a convenient advanced intermediate for the preparation of further compounds disclosed herein where $R^3$ is specified as a 1,3,3a-triazainden-5-yl group.

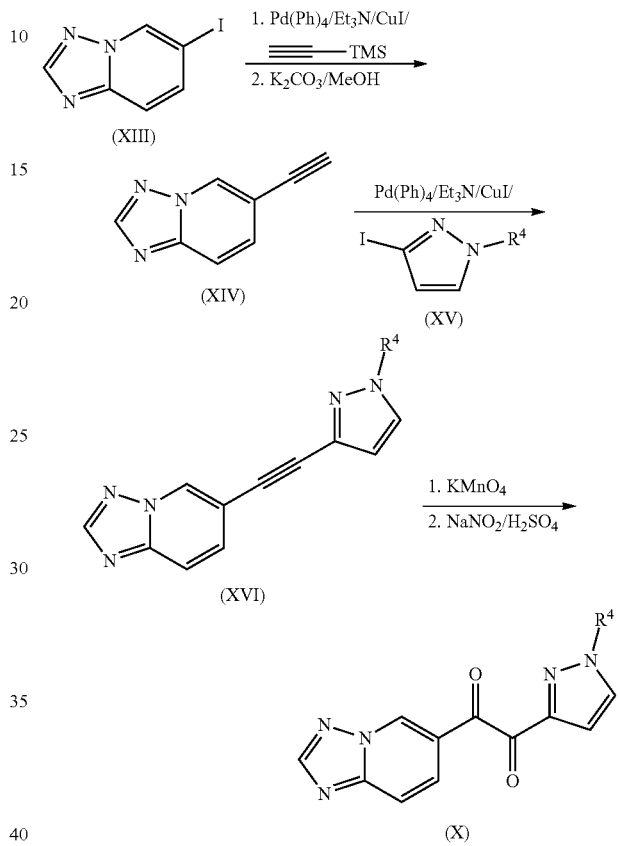

Scheme 3

Scheme 3 shows the synthesis of compound (XXII) beginning with iodide (XVII). As described above, for the synthesis of compound (X) in Scheme 2, two successive Sonogashira reactions may be used to make compound (XIX), which is then oxidized to the diketone (XX). Cyclization of (XX) with ammonium acetate and an appropriate benzaldehyde (XXI) in acetic acid gives final compound (XXII). As described above, $R^{11}$ may represent halogen, alkyl group, etc. as defined by R1 above. Those skilled in the art will appreciate that the intermediate diketone (XX) may represent a convenient advanced intermediate for the preparation of further compounds disclosed where $R^3$ is specified as a 1,3-benzothiazol-6-yl group.

Scheme 3

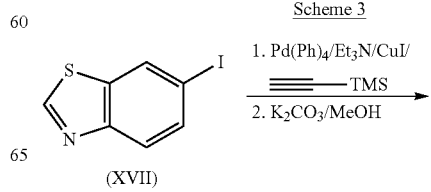

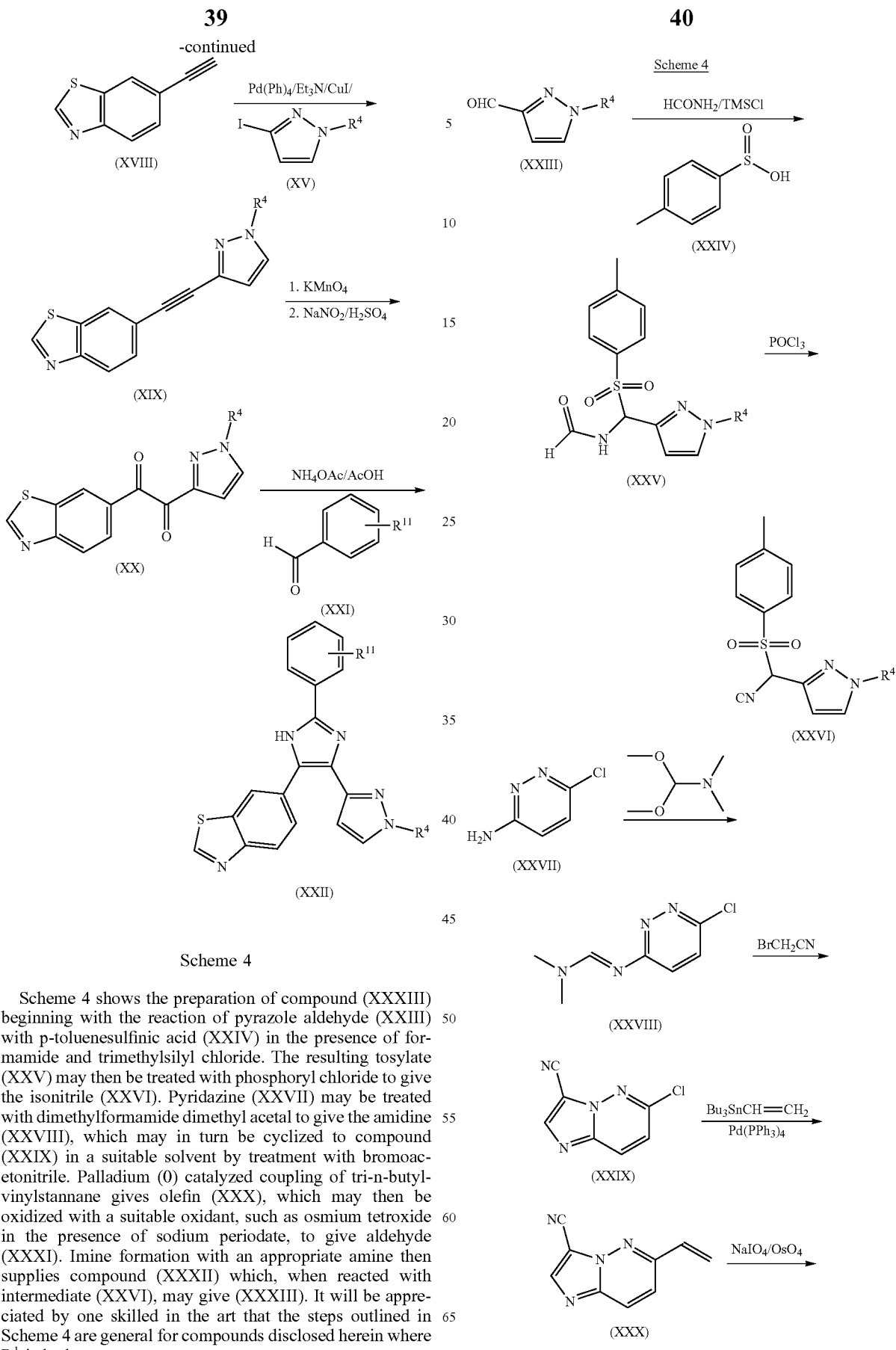

Scheme 4

Scheme 4 shows the preparation of compound (XXXIII) beginning with the reaction of pyrazole aldehyde (XXIII) with p-toluenesulfinic acid (XXIV) in the presence of formamide and trimethylsilyl chloride. The resulting tosylate (XXV) may then be treated with phosphoryl chloride to give the isonitrile (XXVI). Pyridazine (XXVII) may be treated with dimethylformamide dimethyl acetal to give the amidine (XXVIII), which may in turn be cyclized to compound (XXIX) in a suitable solvent by treatment with bromoacetonitrile. Palladium (0) catalyzed coupling of tri-n-butylvinylstannane gives olefin (XXX), which may then be oxidized with a suitable oxidant, such as osmium tetroxide in the presence of sodium periodate, to give aldehyde (XXXI). Imine formation with an appropriate amine then supplies compound (XXXII) which, when reacted with intermediate (XXVI), may give (XXXIII). It will be appreciated by one skilled in the art that the steps outlined in Scheme 4 are general for compounds disclosed herein where $R^1$ is hydrogen.

41
-continued

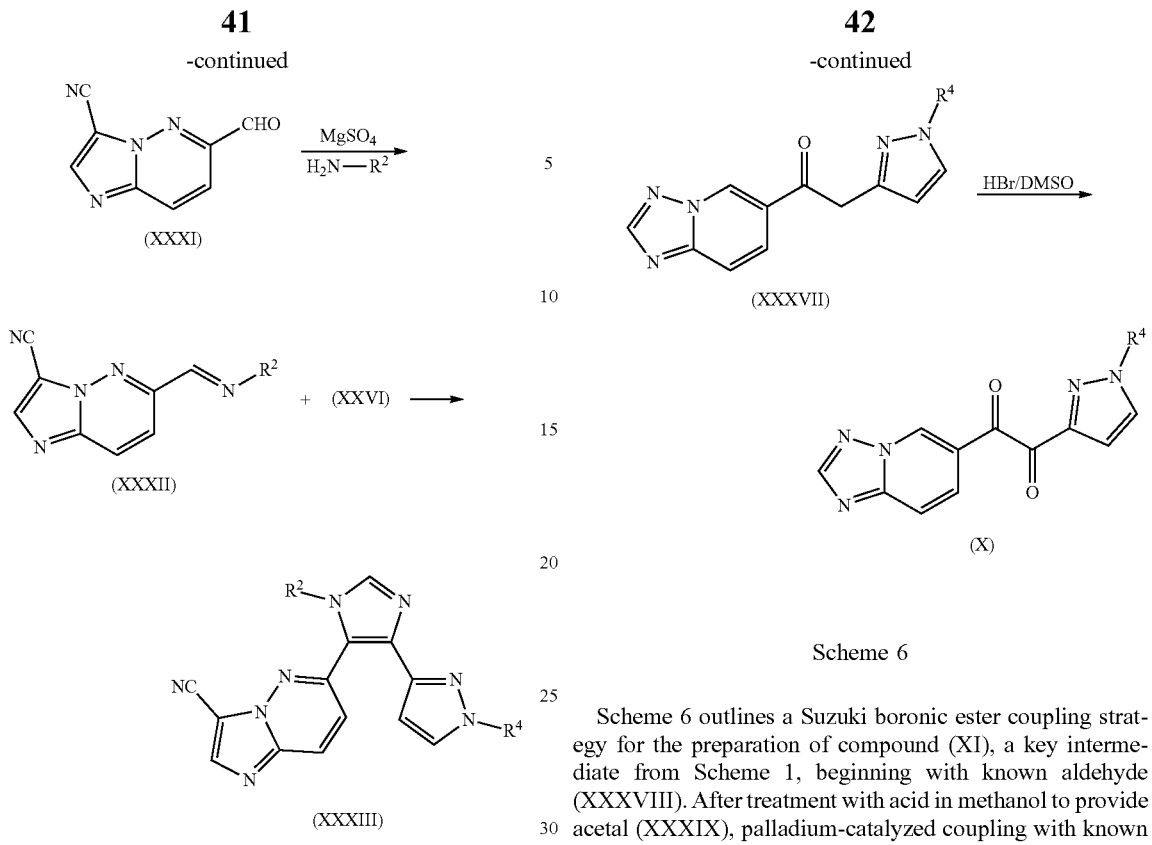

Scheme 5

Scheme 5 shows an alternate preparation of compound (X), a key intermediate from Scheme 1, beginning with known aldehyde (XXXIV), which may be condensed with aniline and diphenylphosphite to provide the known adduct (XXXV). Further reaction with pyrazole aldehyde (XXXVI) then provides ketone (XXXVII), oxidation of which with hydrobromic acid in DMSO gives dione (X).

42
-continued

Scheme 6

Scheme 6 outlines a Suzuki boronic ester coupling strategy for the preparation of compound (XI), a key intermediate from Scheme 1, beginning with known aldehyde (XXXVIII). After treatment with acid in methanol to provide acetal (XXXIX), palladium-catalyzed coupling with known pinacolboronic ester (XL) gives bromide (XLI). A second palladium-catalyzed coupling with pinacolborinic ester (XLII) provides acetal (XI). One skilled in the art will appreciate that intermediate (XXXIX) has an acidic proton in the imidazole ring. This position may be protected if necessary prior to Suzuki coupling using an appropriate group such as a [2-(trimethylsilyl)ethoxy]methyl (SEM) moiety. De-protection using tetra-n-butylammonium fluoride or a similar reagent would then provide the free imidazole at some downstream point in the synthesis.

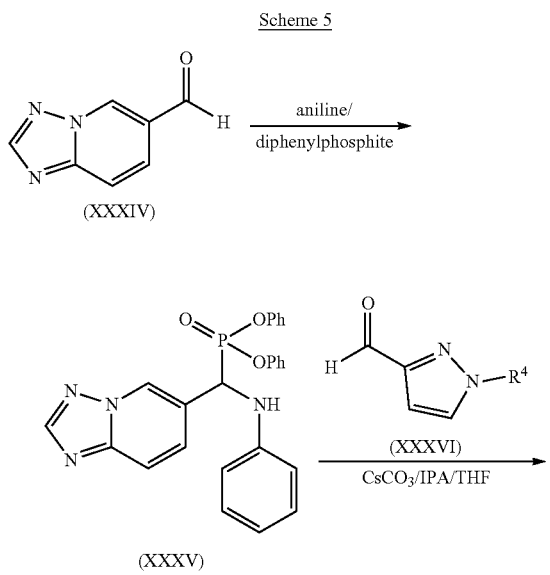

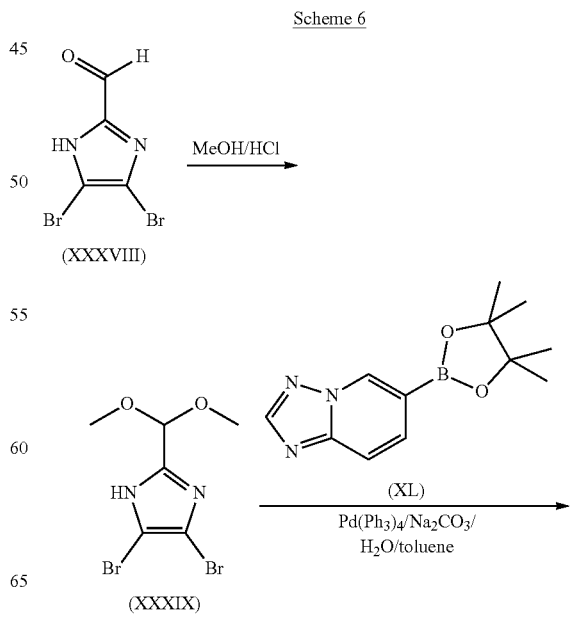

EXAMPLES

Example 1. Synthesis of Compound 1 (N-((5-([1,2,4]triazolo[1,5-a]pyridin-6-yl)-4-(1-methyl-1H-pyrazol-3-yl)-1H-imidazol-2-yl)methyl)-2-fluoroaniline)

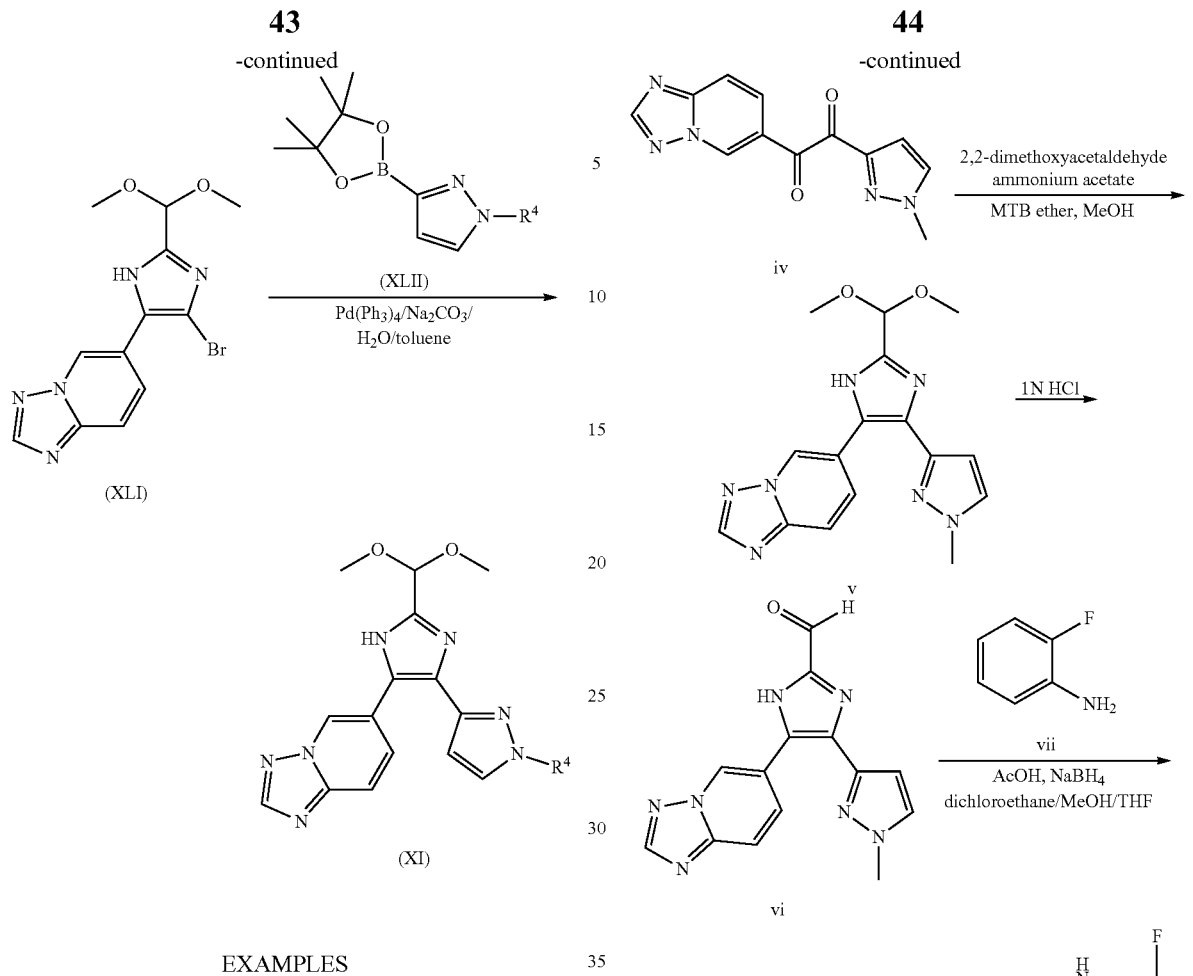

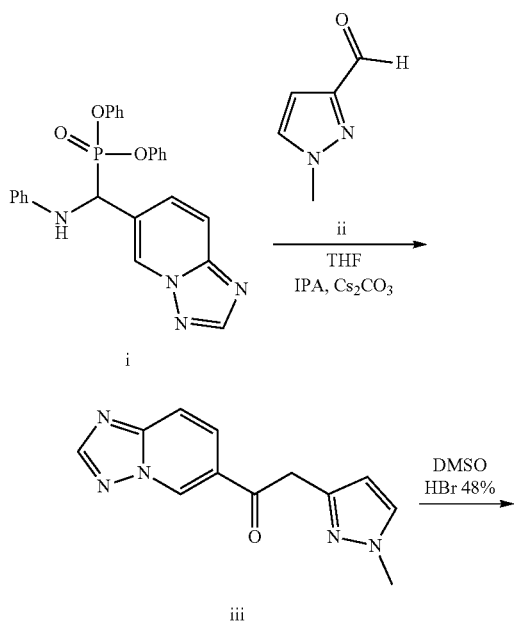

Phosphonate i can be synthesized from known aldehyde [1,2,4]triazolo[1,5-a]pyridine-6-carbaldehyde (CAS #614750-81-1) following Preparation 7 (see below). Known phosphonate i (CAS 1415663-77-2, 6.0 g, 13.2 mmol) and known aldehyde ii (CAS #27258-32-8, 1.75 g, 15.9 mmol) are dissolved in a mixture of dry tetrahydrofuran (112 mL) and dry isopropyl amine (35 mL). Cesium carbonate (6.9 g, 21.2 mmol) is added at room temperature, and the resultant mixture stirred for 20 hours at room temperature until the reaction is complete. The reaction mixture is cooled to 10° C., and 60 mL of 3N HCl is added. The reaction is stirred for 2 hours at room temperature, and the mixture is extracted into methyl 1-butyl ether. The organic layer is separated and washed three times with 1N HCl (25 mL). Residual solvent is evaporated to give iii in 78% yield.

The resulting product (iii, 2.5 g, 10.3 mmol) was dissolved in DMSO (20 mL) and cooled to 0° C. Hydrobromic acid (48%, 5 mL, 41.5 mmol) is added. The reaction is heated to 65° C. and stirred for 2 hours. After cooling to 0° C., 10 g of ice is added to the reaction mixture, and the pH adjusted to pH 10 by addition of 10% potassium carbonate. The mixture is stirred at 10° C. for 10 minutes, and the resultant yellow solid (iv) is filtered and rinsed with ice-cold water (76% yield).

Dione iv (2.0 g, 7.8 mmol) is dissolved in methyl t-butyl ether (40 mL) and dry methanol (20 mL). 2,2-dimethoxy acetaldehyde (1.7 g, 9.6 mmol) and ammonium acetate (60%, 1.5 g, 12 mmol) are added. The reaction is stirred at room temperature for 18 hours, then cooled to 10° C. The pH is adjusted to pH 8-9 via addition of aqueous sodium carbonate. The resultant mixture is extracted into chloroform (3×50 mL). The organic layer is washed with water and dried over sodium sulfate before removal of the residual solvent. The resultant brown oil is dissolved in methyl t-butyl ether (15 mL) and the solvent is removed. Hexanes (2×20 mL) are added, and the solvent is decanted to give v in 95% yield.

The resulting solid (v, 2.5 g, 7.4 mmol) is dissolved in 1N HCl (55 mL) and stirred for 3 hours at 70° C. The mixture is cooled to 0° C. and the pH adjusted to 7-8 with aqueous sodium bicarbonate. The solid is separated and maintained for 30 minutes at 5° C., after which it is filtered and washed with ice-cold water. Methanol is added, the mixture is heated to 50° C. then cooled and filtered to give a light brown solid (aldehyde vi, 83% yield).

Aldehyde vi (1 g, 3.4 mmol) is dissolved in dichloroethane (20 mL). Acetic acid (200 mg, 3.4 mmol) is added, along with 2-fluoro-aniline (vii, 560 mg, 5.1 mmol). The mixture is refluxed for 2 hours, then cooled to 0° C. Methanol (10 mL) and tetrahydrofuran (5 mL) are added, then 538 mg (10.2 mmol) of sodium borohydride are added slowly. The mixture is warmed to room temperature and stirred for 3 hours. The reaction is cooled to 10° C. and the pH adjusted to pH 7 with 1N HCL. The mixture is extracted into dichloromethane, and the organic layer is dried over sodium sulfate. Residual solvent is removed prior to flash chromatography in 5% methanol in dichloromethane to yield 1 (MS m/z M+1=389.2).

Further compounds that can be prepared essentially according to the method described above are shown in Table 3:

TABLE 3

| # | Structure and Name | Physical Data (MS, m/z M + 1) | % Yield (overall) |
|---|---|---|---|
| 3 | N-((5-([1,2,4]triazolo[1,5-a]pyridin-6-yl)-4-(1-methyl-1H-pyrazol-3-yl)-1H-imidazol-2-yl)methyl)aniline z | 371.3 | 21.4% |

TABLE 3-continued

| # | Structure and Name | Physical Data (MS, m/z M + 1) | % Yield (overall) |
|---|---|---|---|
| 5 | N-((5-([1,2,4]triazolo[1,5-a]pyridin-6-yl)-4-(1-methyl-1H-pyrazol-3-yl)-1H-imidazol-2-yl)methyl)-3-fluoroaniline | 389.2 | 16.8% |
| 7 | N-((5-([1,2,4]triazolo[1,5-a]pyridin-6-yl)-4-(1-methyl-1H-pyrazol-3-yl)-1H-imidazol-2-yl)methyl)-4-fluoroaniline | 389.2 | 17.8% |
| 11 | N-((5-([1,2,4]triazolo[1,5-a]pyridin-6-yl)-4-(1-methyl-1H-pyrazol-3-yl)-1H-imidazol-2-yl)methyl)-4-chloroaniline | 405.2 | 9.7% |

TABLE 3-continued

| # | Structure and Name | Physical Data (MS, m/z M + 1) | % Yield (overall) |
|---|---|---|---|
| 13 | 2-(((5-([1,2,4]triazolo[1,5-a]pyridin-6-yl)-4-(1-methyl-1H-pyrazol-3-yl)-1H-imidazol-2-yl)methyl)amino)benzonitrile | 396.3 | 14.1% |
| 15 | 3-(((5-([1,2,4]triazolo[1,5-a]pyridin-6-yl)-4-(1-methyl-1H-pyrazol-3-yl)-1H-imidazol-2-yl)methyl)amino)benzonitrile | 396.2 | 9.7% |

Replacing 1-methyl-1H-pyrazole-3-carbaldehyde (ii) with 1-isopropyl-1H-pyrazole-3-carbaldehyde (CAS #1226694-29-6) in the above sequence provides for the synthesis of the compounds listed in Table 4.

TABLE 4

| # | Structure and Name | Physical Data (MS, m/z M + 1) | % Yield (overall) |
|---|---|---|---|
| 9 | N-((5-([1,2,4]triazolo[1,5-a]pyridin-6-yl)-4-(1-isopropyl-1H-pyrazol-3-yl)-1H-imidazol-2-yl)methyl)aniline | 399.5 | 9.6% |
| 19 | N-((5-([1,2,4]triazolo[1,5-a]pyridin-6-yl)-4-(1-isopropyl-1H-pyrazol-3-yl)-1H-imidazol-2-yl)methyl)-3-fluoroaniline | 417.3 | 20% |
| 28 | 3-(((5-([1,2,4]triazolo[1,5-a]pyridin-6-yl)-4-(1-isopropyl-1H-pyrazol-3-yl)-1H-imidazol-2-yl)methyl)amino)benzonitrile | 424.2 | 14% |
| 35 | N-((5-([1,2,4]triazolo[1,5-a]pyridin-6-yl)-4-(1-isopropyl-1H-pyrazol-3-yl)-1H-imidazol-2-yl)methyl)-3,5-difluoroaniline | 435.4 | 29% |

Example 2. Synthesis of Compound 17 (4-(5-([1,2,4]triazolo[1,5-a]pyridin-6-yl)-4-(1-isopropyl-1H-pyrazol-3-yl)-1H-imidazol-2-yl)benzamide)

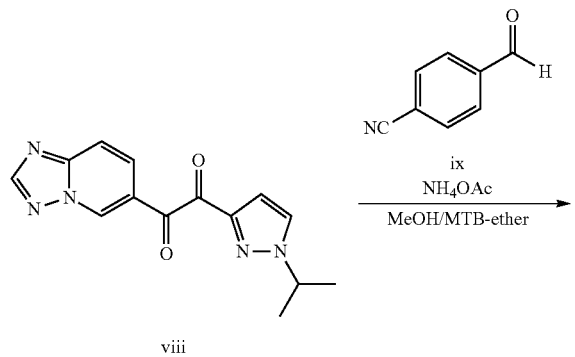

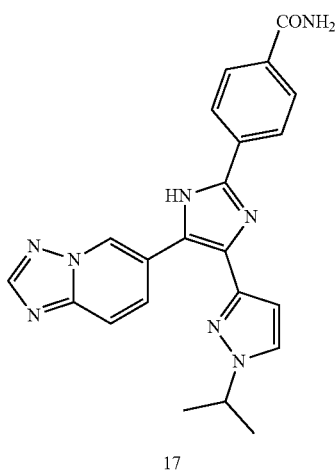

Starting dione viii (150 mg, 0.53 mmol) is dissolved in methanol (1.5 mL) and methyl t-butyl ether (3.0 mL). The reaction is cooled to 15° C. and 4-cyanobenzaldehyde ix (174 mg, 1.325 mmol) and ammonium acetate (102 mg, 1.325 mmol) are added. The reaction is stirred at room temperature for 16 hours, and quenched with aqueous sodium bicarbonate (to pH 8). The mixture is extracted into ethyl acetate, and the organic layer is washed with brine, dried over sodium sulfate, and concentrated to yield desired nitrile x in 23% yield.

Nitrile x (40 mg, 0.10 mmol) is dissolved in concentrated sulfuric acid (1.0 mL) at 10° C., then warmed to room temperature and stirred for 5 hours. The reaction is cooled to 0° C., then diluted with ice. Aqueous ammonia is added (to pH=8.5), and the mixture is extracted into dichloromethane. The organic layer is washed with brine, dried over sodium sulfate, and concentrated. The product is purified on aluminum oxide, using 5% methanol in dichloromethane as the mobile phase to give 17 in 50% yield (MS m/z M+2=414.2)

Example 3. Synthesis of Compound 29 (3-(((5-([1,2,4]triazolo[1,5-a]pyridin-6-yl)-4-(1-isopropyl-1H-pyrazol-3-yl)-1H-imidazol-2-yl)methyl)amino)benzamide)

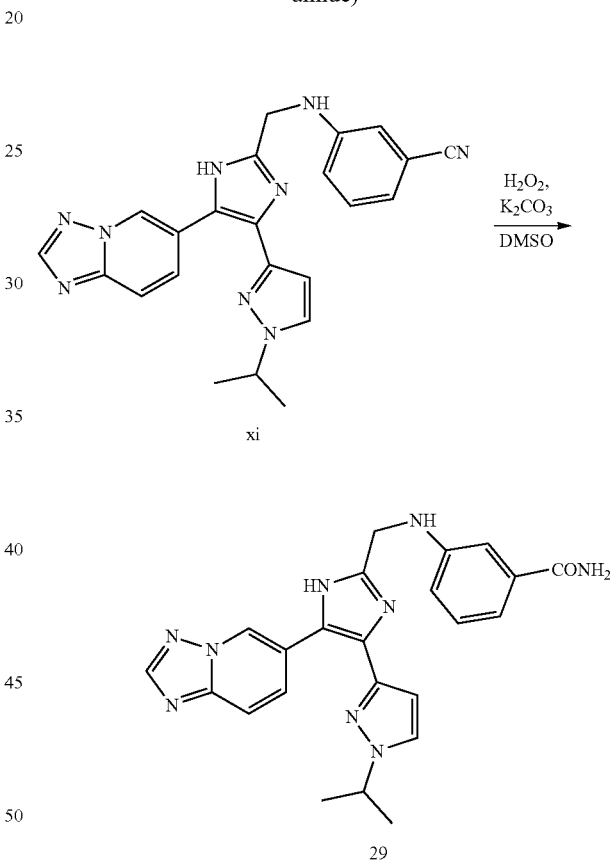

In an alternative method to install the desired amide, nitrile xi (50 mg, 0.118 mmol) is dissolved in DMSO (2 mL), and potassium carbonate (18 mg, 0.13 mmol) is added, followed by hydrogen peroxide (0.6 mL). The reaction is heated to 100° C. and stirred for 1 hour. The mixture is diluted with 10 mL of water and extracted into dichloromethane. The organic layer is washed with brine, dried over sodium sulfate, and concentrated. The crude material is purified on basic aluminum oxide with 5% methanol in dichloromethane as the mobile phase to give compound 29 in trace yield.

Either method of amide installation can be used to complete the synthesis of compound 18 (below) from compound 15.

TABLE 5

| # | Structure and Name | Physical Data | % Yield (from nitrile) |
|---|---|---|---|
| 18 | ![structure] 3-(((5-([1,2,4]triazolo[1,5-a]pyridin-6-yl)-4-(1-methyl-1H-pyrazol-3-yl)-1H-imidazol-2-yl)methyl)amino)benzamide | 414.3 | 12% |

Example 4. Synthesis of Diphenyl ((3-cyanoimidazo[1,2-b]pyridazin-6-yl)(phenylamino)methyl)phosphonate (xiii)

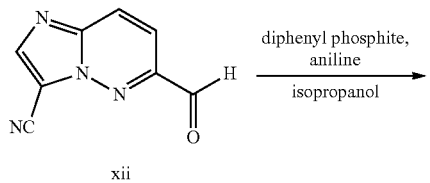

Known aldehyde xii (see WO 2016/140884, CAS #2001563-08-0) (1.0 g, 5.8 mmol) and aniline (550 mg, 5.9 mmol) are added to a dry round bottom flask and stirred for 30 minutes. Isopropanol (2 mL) is added and the reaction stirred for 2 hours at room temperature. Diphenyl phosphite (1.5 mL, 7.5 mmol) is added, and the reaction heated to 45° C. for one hour, then stirred overnight at room temperature. The solvent is removed and the product purified by flash chromatography (10%-30% ethyl acetate in hexanes) to give xiii in 47% yield.

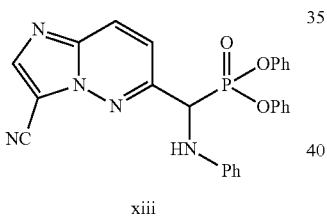

Once synthesized, phosphonate xiii can be treated to the conditions described in to give compound 27 shown below in Table 6.

TABLE 6

| # | Structure and Name | Physical Data (MS, m/z M + 1) | % Yield (overall) |
|---|---|---|---|
| 27 | ![structure] 6-(2-(((3-fluorophenyl)amino)methyl)-4-(1-isopropyl-1H-pyrazol-3-yl)-1H-imidazol-5-yl)imidazo[1,2-b]pyridazine-3-carbonitrile | 442.3 | 1.1% |

Compound 27 can further be treated using the conditions in Example 3 to give compound 34 shown below in Table 7.

TABLE 7

| # | Structure and Name | Physical Data (MS, m/z M + 1) | % Yield (from nitrile) |
|---|---|---|---|
| 34 | 6-(2-(((3-fluorophenyl)amino)methyl)-4-(1-isopropyl-1H-pyrazol-3-yl)-1H-imidazol-5-yl)imidazo[1,2-b]pyridazine-3-carboxamide | 460.3 | <1% |

Example 5. Synthesis of 6-(2-formyl-4-(1-isopropyl-1H-pyrazol-3-yl)-1H-imidazol-5-yl)imidazo[1,2-b]pyridazine-3-carboxamide (xv)

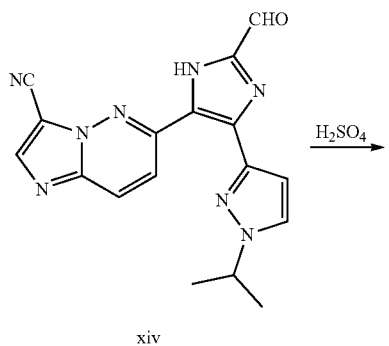

xiv

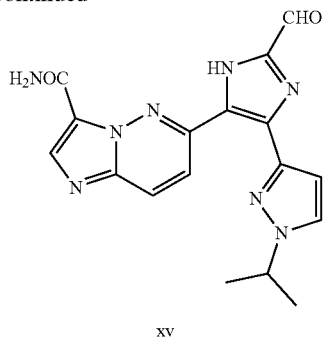

xv

The amide is installed earlier in the synthesis using the procedure described in Example 2. For the synthesis of compound 37 (below), the procedure is then completed as described in Example 1.

TABLE 8

| # | Structure and Name | Physical Data (MS, m/z M + 1) | % Yield (overall) |
|---|---|---|---|
| 38 | 6-(2-(((3-cyanophenyl)amino)methyl)-4-(1-isopropyl-1H-pyrazol-3-yl)-1H-imidazol-5-yl)imidazo[1,2-b]pyridazine-3-carboxamide | 467.4 | <1% |

Example 6. Synthesis of 1-(1-isopropyl-1H-pyrazol-3-yl)-2-(quinoxalin-6-yl)ethane-1,2-dione (xix)

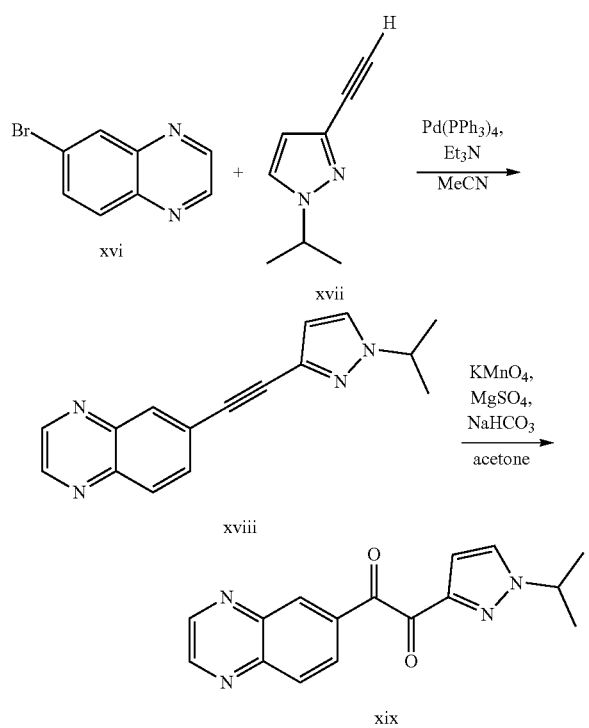

Known quinoxaline xvi (CAS #50998-17-9, 1.0 g, 4.78 mmol) is dissolved in acetonitrile (20 mL) under inert atmosphere. Triethylamine (6.6 mL, 47.8 mmol) is added, followed by known pyrazole xvii (CAS #1354706-26-5, 850 mg, 5.26 mmol) and palladium tetrakis (665 mg, 0.478 mmol). The reaction is heated to 70° C. and stirred for 18 hours. The solvent is removed by distillation under vacuum at 55° C., and the resultant product is purified by flash chromatography (30% ethyl acetate in petroleum ether) to give xviii in 80% yield.

To a solution of magnesium sulfate (940 mg, 3.82 mmol) and sodium bicarbonate (80 mg, 0.95 mmol) in water (10 mL) is added a solution of the starting material xviii (500 mg, 1.91 mmol) in acetone (20 mL). HighFlow (800 mg) is added (note that Celite could be used as an alternative), followed by potassium permanganate (600 mg, 3.82 mmol), and the reaction is stirred for 2 hours. Aqueous sodium carbonate is added and the reaction mixture is extracted into ethyl acetate. The residual solvent is distilled off, and the crude material is washed with methyl t-butyl ether (2×5 mL) to provide xix in 59% yield.

Once synthesized, xix can be treated to the same conditions shown for iv in Example 1 to continue the sequence and form the compounds shown below in Table 9.

TABLE 9

| # | Structure and Name | Physical Data (MS, m/z M + 1) | % Yield (overall) |
|---|---|---|---|
| 21 | 3-fluoro-N-((4-(1-isopropyl-1H-pyrazol-3-yl)-5-(quinoxalin-6-yl)-1H-imidazol-2-yl)methyl)aniline | 428.3 | 6.1% |
| 39 | 3,5-difluoro-N-((4-(1-isopropyl-1H-pyrazol-3-yl)-5-(quinoxalin-6-yl)-1H-imidazol-2-yl)methyl)aniline | 445.2 | 12% |

TABLE 9-continued

| # | Structure and Name | Physical Data (MS, m/z M + 1) | % Yield (overall) |
|---|---|---|---|
| 40 | N-(4-(1-isopropyl-1H-pyrazol-3-yl)-5-(quinoxalin-6-yl)-1H-imidazol-2-yl)methyl)-3-(1H-pyrazol-1-yl)aniline | 476.3 | 9.2% |
| 41 | 3-(((4-(1-isopropyl-1H-pyrazol-3-yl)-5-(quinoxalin-6-yl)-1H-imidazol-2-yl)methyl)amino)benzonitrile | 435.3 | 7.1% |
| 45 | 2,5-difluoro-N-((4-(1-isopropyl-1H-pyrazol-3-yl)-5-(quinoxalin-6-yl)-1H-imidazol-2-yl)methyl)aniline | 446.2 | 3.4% |
| 48 | 3,4-difluoro-N-((4-(1-isopropyl-1H-pyrazol-3-yl)-5-(quinoxalin-6-yl)-1H-imidazol-2-yl)methyl)aniline | 446.3 | 9.6% |

TABLE 9-continued

| # | Structure and Name | Physical Data (MS, m/z M + 1) | % Yield (overall) |
|---|---|---|---|
| 49 | 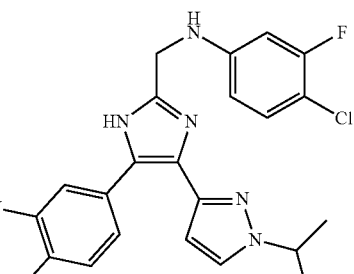<br>4-chloro-3-fluoro-N-((4-(1-isopropyl-1H-pyrazol-3-yl)-5-(quinoxalin-6-yl)-1H-imidazol-2-yl)methyl)aniline | 462.3 | 6.5% |
| 50 | 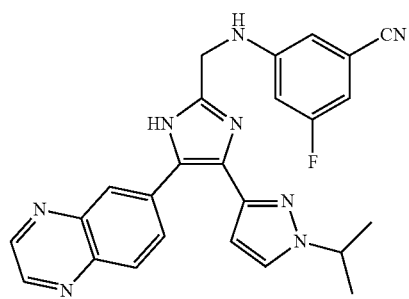<br>3-fluoro-5-(((4-(1-isopropyl-1H-pyrazol-3-yl)-5-(quinoxalin-6-yl)-1H-imidazol-2-yl)methyl)amino)benzonitrile | 452.2 | 3.1% |
| 51 | 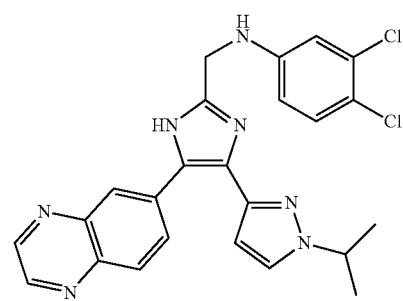 [SMILES: CC(C)n1ccc(-c2nc(CNc3ccc(Cl)c(F)c3)[nH]c2-c2ccc3nccnc3c2)n1]<br>3,4-dichloro-N-((4-(1-isopropyl-1H-pyrazol-3-yl)-5-(quinoxalin-6-yl)-1H-imidazol-2-yl)methyl)aniline | 480.2 | 7.7% |
| 54 | 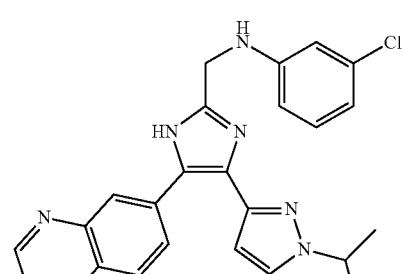<br>3-chloro-N-((4-(1-isopropyl-1H-pyrazol-3-yl)-5-(quinoxalin-6-yl)-1H-imidazol-2-yl)methyl)aniline z | 444.3 | 8.3% |

TABLE 9-continued

| # | Structure and Name | Physical Data (MS, m/z M + 1) | % Yield (overall) |
|---|---|---|---|
| 57 | 2-fluoro-N-((4-(1-isopropyl-1H-pyrazol-3-yl)-5-(quinoxalin-6-yl)-1H-imidazol-2-yl)methyl)aniline | 428.3 | 3.5% |
| 58 | 3-fluoro-5-(((4-(1-isopropyl-1H-pyrazol-3-yl)-5-(quinoxalin-6-yl)-1H-imidazol-2-yl)methyl)amino)benzamide | 471.3 | 3.7% |

Alternatively, subjecting xix to the conditions shown in Example 2 gives the exemplary compounds shown in Table 10. Note that, for compounds 42 and 43, 3-ethynyl-1-methyl-1H-pyrazole (CAS #61514-59-8) should be substituted for pyrazole xvii in Example 6.

TABLE 10

| # | Structure and Name | Physical Data (MS, m/z M + 1) | % Yield (overall) |
|---|---|---|---|
| 42 | 4-(4-(1-methyl-1H-pyrazol-3-yl)-5-(quinoxalin-6-yl)-1H-imidazol-2-yl)benzonitrile | 378.2 | 1.2% |

TABLE 10-continued

| # | Structure and Name | Physical Data (MS, m/z M + 1) | % Yield (overall) |
|---|---|---|---|
| 43 | 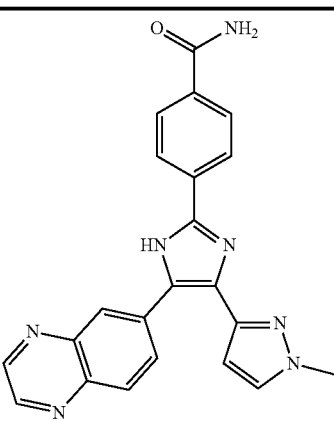<br>4-(4-(1-methyl-1H-pyrazol-3-yl)-5-(quinoxalin-6-yl)-1H-imidazol-2-yl)benzamide | 396.2 | <1% |
| 59 | 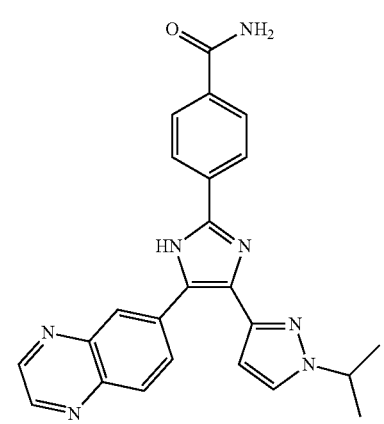 [SMILES: CC(C)n1ccc(-c2nc(-c3ccc(C(N)=O)cc3)[nH]c2-c2ccc3nccnc3c2)n1]<br>4-(4-(1-isopropyl-1H-pyrazol-3-yl)-5-(quinoxalin-6-yl)-1H-imidazol-2-yl)benzamide | 424.3 | 7.1% |

Example 7. Synthesis of Diphenyl ((phenylamino)quinolin-6-yl)methyl)phosphonate (xxi)

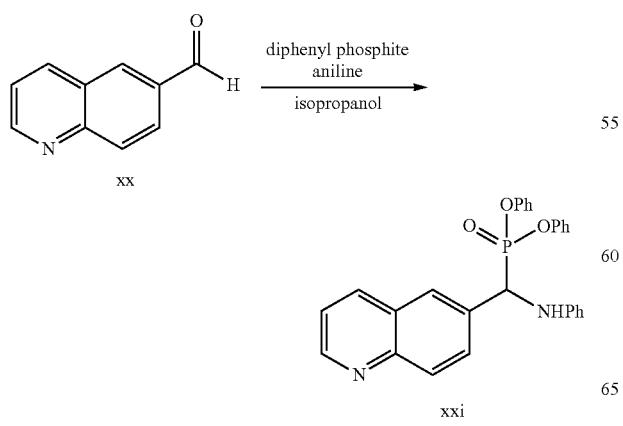

To a round bottom flask under inert atmosphere is added aldehyde xx (CAS #14113-04-6, 50 mg, 0.32 mmol) and aniline (30 mg. 0.32 mmol). The mixture is stirred for 30 minutes and isopropanol (0.25 mL) is added. The reaction is stirred for 2 hours, then diphenyl phosphite (90 mg, 0.38 mmol) is added. The reaction is stirred overnight, then filtered and the resultant solid washed with methyl t-butyl ether to give xxi in 74% yield.

Once synthesized, xxi can be subjected to the conditions described in Example 1 to give the compounds shown in Table 11. Note that, for compounds 25 and 32, aldehyde ii should be replaced with 1-isopropyl-1H-pyrazole-3-carbaldehyde (CAS #1226694-29-6).

TABLE 11

| # | Structure and Name | Physical Data | % Yield (overall) |
|---|---|---|---|
| 23 | 3-fluoro-N-((4-(1-methyl-1H-pyrazol-3-yl)-5-(quinolin-6-yl)-1H-imidazol-2-yl)methyl)aniline | 398.2 | <1% |
| 25 | 3-fluoro-N-((4-(1-isopropyl-1H-pyrazol-3-yl)-5-(quinolin-6-yl)-1H-imidazol-2-yl)methyl)aniline | 427.5 | <1% |
| 30 | 2-fluoro-N-((4-(1-methyl-1H-pyrazol-3-yl)-5-(quinolin-6-yl)-1H-imidazol-2-yl)methyl)aniline | 398.2 | <1% |
| 32 | 2-fluoro-N-((4-(1-isopropyl-1H-pyrazol-3-yl)-5-(quinolin-6-yl)-1H-imidazol-2-yl)methyl)aniline | 427.2 | <1% |

Example 8. Synthesis of 1-(benzo[d]thiazol-6-yl)-2-(1-methyl-1H-pyrazol-3-yl)ethane-1,2-dione (xxv)

The synthesis of xxv can be accomplished by subjecting known iodide (CAS #654070-00-5) and known alkyne xxiii (CAS #61514-59-8) to the conditions described in Example 6. Once in hand, xxv can be used to synthesize the compounds shown below in Table 12 by using the procedure described in Example 2 to form the nitrile and Example 3 to install the amide.

TABLE 12

| # | Structure and Name | Physical Data (MS, m/z M + 1) | % Yield (overall) |
|---|---|---|---|
| 37 | 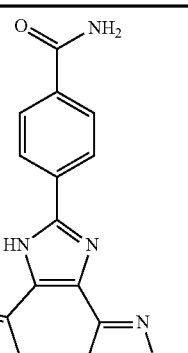<br>4-(5-(benzo[d]thiazol-6-yl)-4-(1-methyl-1H-pyrazol-3-yl)-1H-imidazol-2-yl)benzamide | 401.2 | 2.7% |

Example 9. Synthesis of Compound 44 (6-(2-methyl-4-(1-methyl-1H-pyrazol-3-yl)-1H-imidazol-5-yl)benzo[d]thiazole)

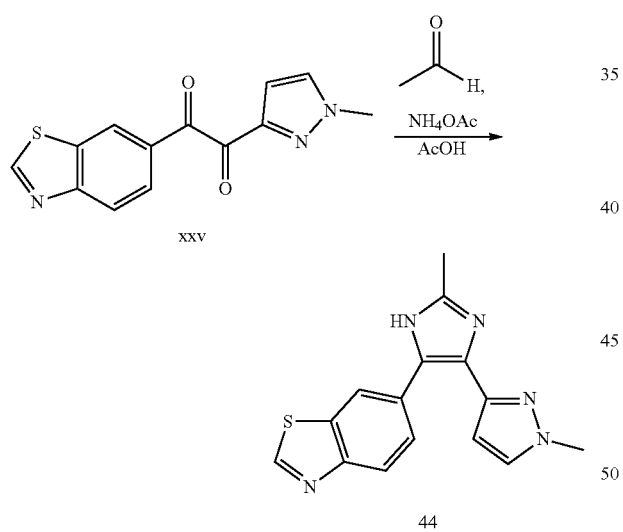

Dione xxv (250 mg. 0.73 mmol) is dissolved in acetic acid (10 mL). Acetaldehyde (20%, 500 mg. 1.84 mmol) and ammonium acetate (340 mg, 4.42 mmol) are added. The mixture is heated to 100° C. for 2 hours. Water and ammonium hydroxide are added, after which the mixture is extracted into dichloromethane, and the solvent is removed. The crude product is purified by flash column chromatography (4-6% methanol in dichloromethane) to give 44 in 27% yield (MS m/z M+1=296.2).

Compound 55 can be synthesized by the same method with the substitution of formaldehyde for acetaldehyde.

Compounds 52 and 56 are synthesized following the same method, using xix (or the corresponding methyl-substituted derivative) in place of xxv as the starting material.

Compound 63 can also be synthesized following Example 9, using 4-formyl-2,6-dimethylbenzonitrile in place of acetaldehyde, and following Example 2 to install the amide using sulfuric acid.

TABLE 13

| # | Structure and Name | Physical Data (MS, m/z M + 1) | % Yield (overall) |
|---|---|---|---|
| 52 | 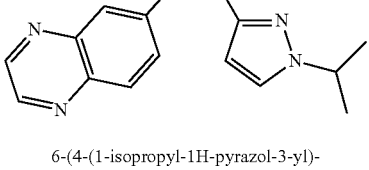<br>6-(4-(1-isopropyl-1H-pyrazol-3-yl)-1H-imidazol-5-yl)quinoxaline | 305.2 | 9.1% |
| 55 | 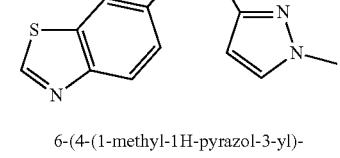<br>6-(4-(1-methyl-1H-pyrazol-3-yl)-1H-imidazol-5-yl)benzo[d]thiazole | 282.1 | 3.7% |
| 56 | 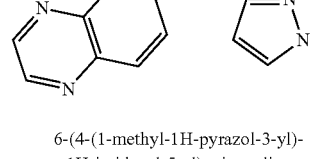<br>6-(4-(1-methyl-1H-pyrazol-3-yl)-1H-imidazol-5-yl)quinoxaline | 277.2 | 7.5% |
| 63 | 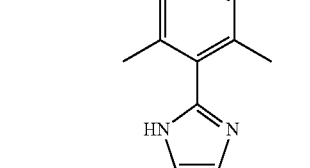<br>4-(5-(benzo[d]thiazol-6-yl)-4-(1-methyl-1H-pyrazol-3-yl)-1H-imidazol-2-yl)-3,5-dimethylbenzamide | 429.2 | 4.9% |

Example 10. Synthesis of Compound 62 (5-(benzo[d]thiazol-6-yl)-4-(1-methyl-1H-pyrazol-3-yl)-1H-imidazole-2-carboxamide)

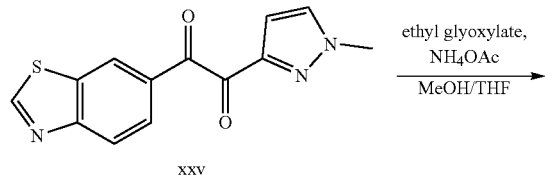

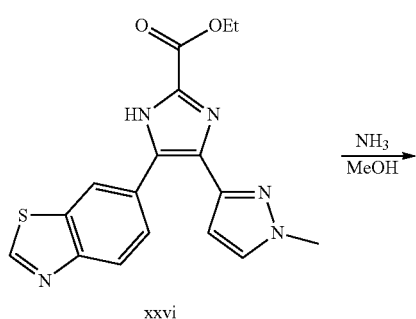

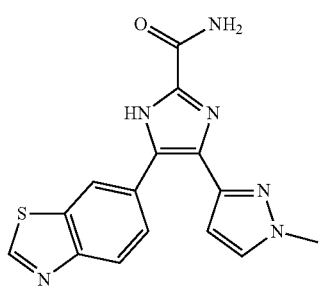

Starting dione xxv (200 mg, 0.738 mmol) is dissolved in methanol (2 mL) and tetrahydrofuran (2 mL). Ammonium acetate (570 mg, 7.38 mmol) and ethyl glyoxalate (0.23 mL, 1.10 mmol) are added. The reaction is stirred for 18 hours, then quenched with aqueous sodium sulfite. The mixture is extracted into ethyl acetate, and the organic layer is dried over sodium sulfate and concentrated, followed by purification by flash column chromatography (5% methanol in dichloromethane) to give xxvi in 35% yield.

Ester xxvi (100 mg. 0.283 mmol) is dissolved in methanolic ammonia solution (4 mL) in a sealed tube. The reaction is heated at 100° C. for 18 hours, followed by concentration under vacuum at 50° C. The crude mixture is purified on neutral aluminum oxide with 3-5% methanol in dichloromethane as the mobile phase to give 62 (26% yield, MS m/z M+1=325.2).

Example 11. Synthesis of Compound 64 (4-(5-(benzo[d]thiazol-6-yl)-4-(1-methyl-1H-pyrazol-3-yl)-1H-imidazol-2-yl)-N-methylbenzamide)

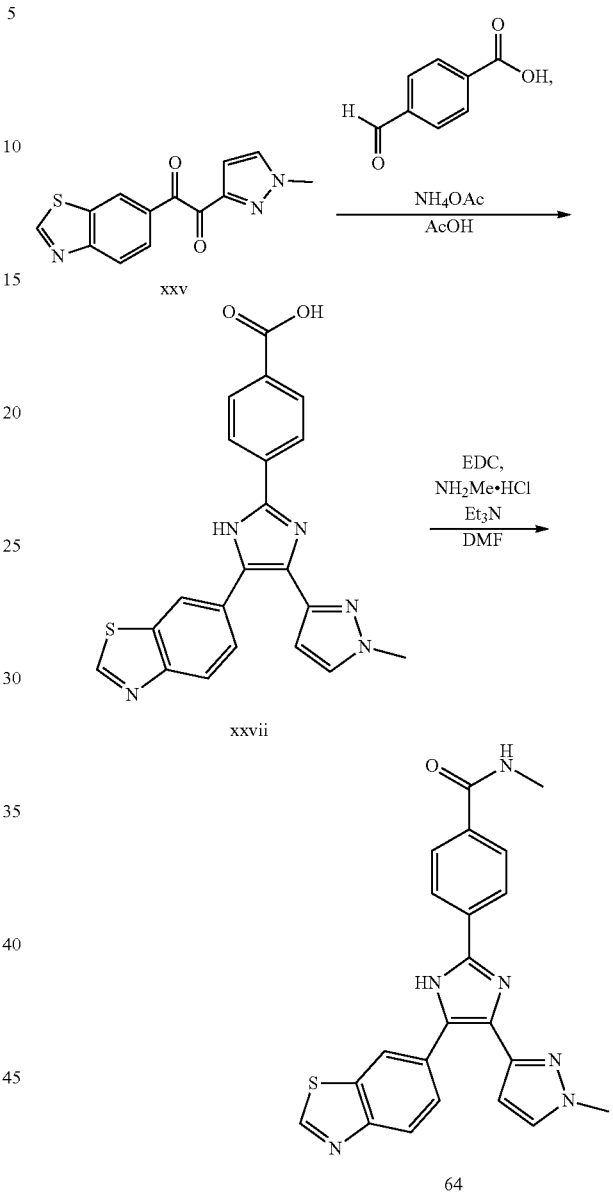

Starting dione xxv (400 mg, 1.476 mmol) can be treated under the conditions described in Example 9 using 4-formyl benzoic acid instead of acetaldehyde to give xxvii in 9.5% yield.

Acid xxvii (200 mg, 0.5 mmol) is dissolved in dimethylformamide (3 mL). Carbonyl diimidazole (161 mg, 1.0 mmol) is added. The reaction is stirred for 40 minutes, then triethylamine (0.18 mL) is added, along with methylamine hydrochloride (40 mg, 0.60 mmol). The reaction is stirred for a further 2 hours, after which the mixture is extracted into ethyl acetate and the organic layer is concentrated prior to purification by flash column chromatography (3-5% methanol in dichloromethane) to provide 64 in 14% yield (MS m/z M+1=415.2).

The same conditions can be used to synthesize the compounds shown below, using ethylamine hydrochloride and dimethylamine hydrochloride, respectively, in place of methylamine hydrochloride.

TABLE 14

| # | Structure and Name | Physical Data (MS, m/z M + 1) | % Yield (overall) |
|---|---|---|---|
| 65 | 4-(5-(benzo[d]thiazol-6-yl)-4-(1-methyl-1H-pyrazol-3-yl)-1H-imidazol-2-yl)-N-ethylbenzamide | 429.3 | 3.0% |
| 66 | 4-(5-(benzo[d]thiazol-6-yl)-4-(1-methyl-1H-pyrazol-3-yl)-1H-imidazol-2-yl)-N,N-dimethylbenzamide | 429.3 | 4.2% |

Example 12. Synthesis of 6-((1-(difluoromethyl)-1H-pyrazol-3-yl)ethynyl)quinoxaline (xxx)

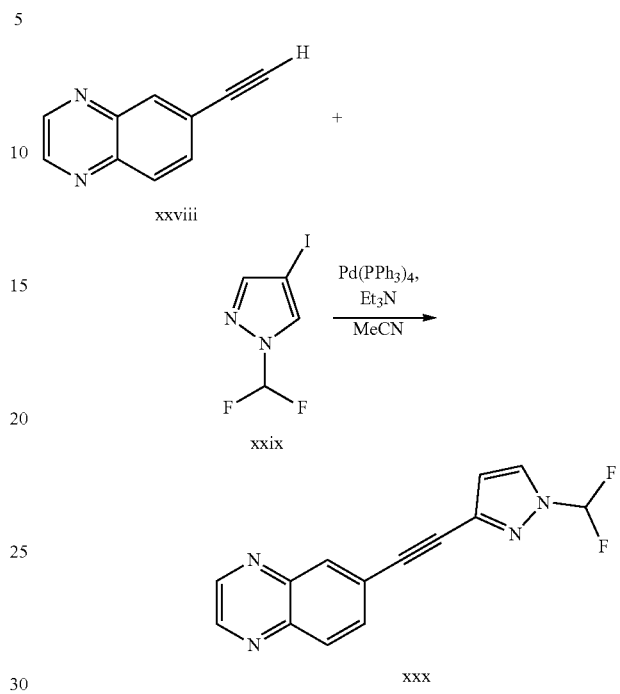

Known alkyne xxviii (CAS #442517-33-1) and known iodide (CAS #1394130-21-2) are treated as described in Example 6 to yield alkyne xxx. Once in hand, xxx can be oxidized as in Example 6, and used to synthesize the compounds shown below in Table 15 by following the steps outlined in Example 1.

Using known benzothiazole (CAS #864376-04-5) in place of alkyne xxviii permits the synthesis of compounds 60 and 61.

Replacing the iodide in Example 12 with 1-cyclopropyl-3-iodo-1H-pyrazole (CAS #1616069-72-7) leads to compound 68.

TABLE 15

| # | Structure and Name | Physical Data (MS, m/z M + 1) | % Yield (overall) |
|---|---|---|---|
| 46 | N-((4-(1-(difluoromethyl)-1H-pyrazol-3-yl)-5-(quinoxalin-6-yl)-1H-imidazol-2-yl)methyl)-3-fluoroaniline | 436.2 | 1.1% |

TABLE 15-continued
| # | Structure and Name | Physical Data (MS, m/z M + 1) | % Yield (overall) |
|---|---|---|---|
| 47 | 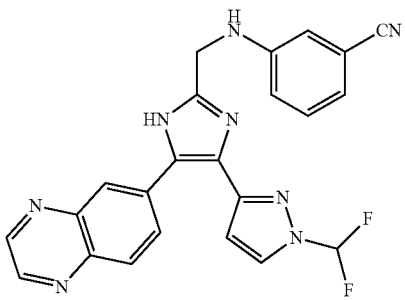 [SMILES: N#Cc1cccc(NCc2nc(-c3ccn(C(F)F)n3)c(-c3ccc4nccnc4c3)[nH]2)c1]<br>3-(((4-(1-(difluoromethyl)-1H-pyrazol-3-yl)-5-(quinoxalin-6-yl)-1H-imidazol-2-yl)methyl)amino)benzonitrile | 443.2 | 1.1% |
| 60 | 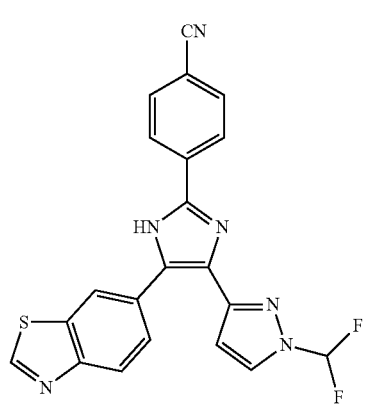 [SMILES: N#Cc1ccc(-c2nc(-c3ccn(C(F)F)n3)c(-c3ccc4ncsc4c3)[nH]2)cc1]<br>4-(5-(benzo[d]thiazol-6-yl)-4-(1-(difluoromethyl)-1H-pyrazol-3-yl)-1H-imidazol-2-yl)benzonitrile | 419.2 | 15% |
| 61 | 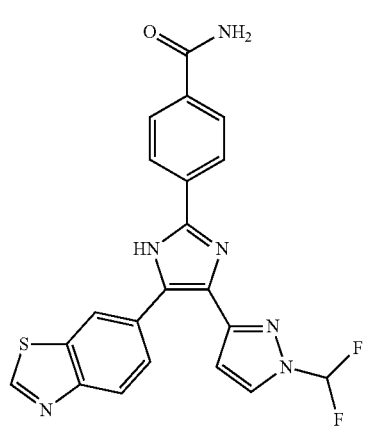 [SMILES: NC(=O)c1ccc(-c2nc(-c3ccn(C(F)F)n3)c(-c3ccc4ncsc4c3)[nH]2)cc1]<br>4-(5-(benzo[d]thiazol-6-yl)-4-(1-(difluoromethyl)-1H-pyrazol-3-yl)-1H-imidazol-2-yl)benzamide | 437.2 | <1% |

TABLE 15-continued

| # | Structure and Name | Physical Data (MS, m/z M + 1) | % Yield (overall) |
|---|---|---|---|
| 68 | N-((4-(1-cyclopropyl-1H-pyrazol-3-yl)-5-(quinoxalin-6-yl)-1H-imidazol-2-yl)methyl)-3,5-difluoroaniline | 444.3 | 9.3% |

Example 13. Synthesis of 3-(benzo[d][1,3]dioxol-5-ylethynyl)-1-methyl-1H-pyrazole

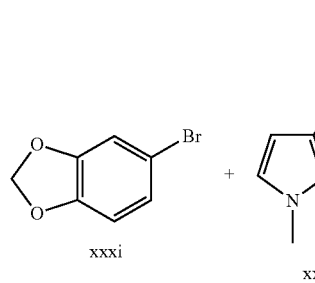

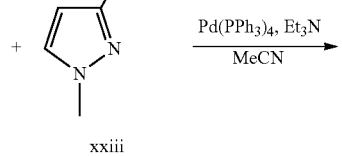

Known bromide xxxi (CAS #2635-13-4) and known alkyne xxiii (CAS #61514-59-8) are subjected to the conditions described in Example 6 to synthesize alkyne xxxii. Further treatment to oxidize the alkyne as in Example 6, followed by the conditions described in Examples 2 and 3 results in the formation of compound 67 (below).

TABLE 16

| # | Structure and Name | Physical Data (MS, m/z M + 1) | % Yield (overall) |
|---|---|---|---|
| 67 | 4-(5-(benzo[d][1,3]dioxol-5-yl)-4-(1-methyl-1H-pyrazol-3-yl)-1H-imidazol-2-yl)benzamide | 388.2 | 6.0% |

Example 14. Synthesis of 3-ethynyl-1-isopropyl-1H-pyrazole (xvii, CAS 1354706-26-5)

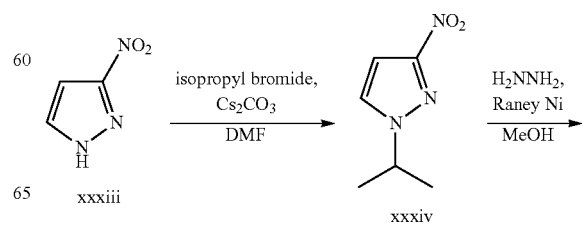

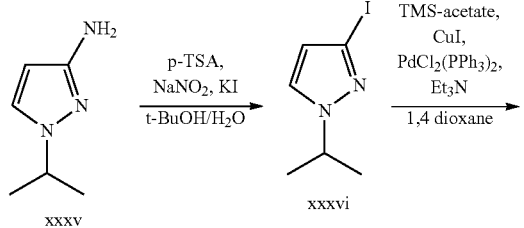

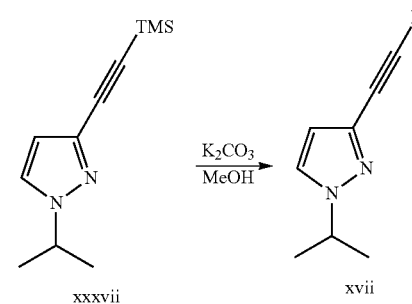

3-Nitro-1H-pyrazole xxxiii (5 g, 44.2 mmol) is dissolved in dimethylformamide (50 mL) and cesium carbonate (14 g, 43 mmol) is added. The reaction is stirred for thirty minutes at room temperature, and isopropyl bromide (5 mL, 53.3 mmol) is added. The reaction is stirred at room temperature for 12 hours, after which water (100 mL) is added and the reaction mixture is stirred for 10 minutes. The mixture is extracted into ethyl acetate (3×100 mL), and the organic layer is washed with brine and concentrated prior to purification by flash column chromatography (20% ethyl acetate in hexanes) to give xxxiv in 73% yield.

Pyrazole xxxiv (2 g. 13.98 mmol) is dissolved in methanol (20 mL) and hydrazine (90%, 0.5 mL, 13.98 mmol) is added. Raney nickel (0.5 g) is added slowly. The temperature is raised to 50° C. for one hour, then the reaction is cooled and the mixture filtered through HighFlow. The filtrate is concentrated and purified by flash column chromatography (20% ethyl acetate in hexanes) to give xxxv in 29% yield.

Amine xxxv (10 g, 0.088 mol) is dissolved in t-butanol (80 mL) and p-toluene sulfonic acid (43 g, 0.25 mol) is added and the reaction is cooled to 15° C. A solution of sodium nitrite (12.15 g, 0.17 mol) and potassium iodide (17.5 g, 0.10 mol) in water (40 mL) is added drop wise. The reaction is then stirred at room temperature for one hour, after which 60 mL of water is added and the mixture is extracted into ethyl acetate. The organic layer is washed with aqueous sodium bicarbonate, then dried over sodium sulfate and concentrated. The crude mixture is purified by flash column chromatography (30% ethyl acetate in hexanes) to give xxxvi in 29% yield.

Iodide xxxvi (2 g, 8.5 mmol) is dissolved in 1,4 dioxane (20 mL) under inert atmosphere and triethylamine (8.8 mL, 63.4 mmol) is added and the mixture stirred for 30 minutes. Trimethylsilyl acetate (3.5 mL, 31.5 mmol) is added and the reaction is stirred for a further 15 minutes. PdCl$_2$(PPh$_3$)$_2$ (58 mg, 0.08 mmol) and copper (I) iodide (32 mg, (0.17 mmol) are added and the reaction is heated to 80° C. for two hours. After cooling to room temperature, the reaction mixture is filtered through HighFlow, and the filtrate is dried over sodium sulfate and concentrated. The crude mixture is purified by flash column chromatography (0-10% ethyl acetate in hexanes) to give xxxvii in 80% yield.

TMS-alkyne xxxvii (1.5 g, 7.3 mmol) is dissolved in methanol (20 mL) under inert atmosphere and potassium carbonate (1.0 g, 7.3 mmol) is added. The reaction is stirred at room temperature for 2 hours, then filtered. The filtrate is concentrated, and water added before extracting the mixture into ethyl acetate. The organic layer is dried over sodium sulfate to give xvii in 71% yield (MS m/z M+1=135.1).

Example 15. Synthesis of 7-bromoquinoxaline-2-carbonitrile (xlv. CAS #1609932-73-1)

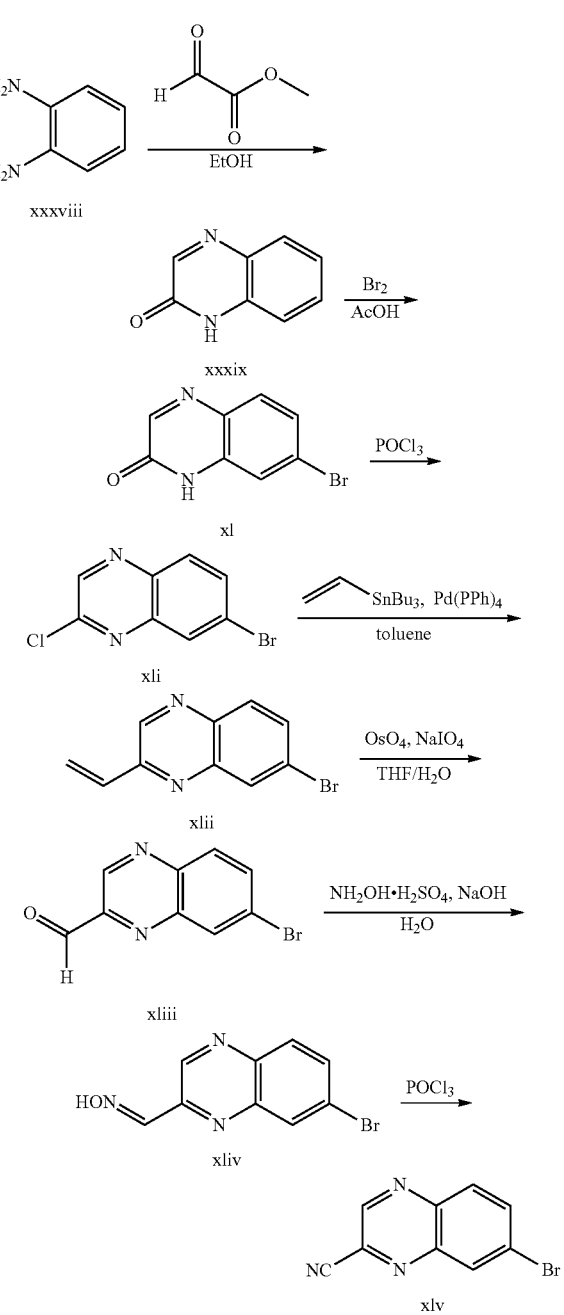

Diamine xxxviii (200 g, 1.85 mol) is dissolved in ethanol (1.2 L). Ethyl glyoxalate (50% in toluene, 450 mL) is added dropwise. The reaction is heated to 50° C. for 12 hours, then cooled to 5° C. for 1 hour. The mixture is filtered and the solid washed with water to give xxxix in 92% yield.

Quinoxalone xxxix (250 g, 1.7 mol) is dissolved in acetic acid (4500 mL). A mixture of acetic acid (988 mL) and bromine (108 mL, 2.1 mol) is added dropwise, and the mixture stirred at room temperature for 12 hours, then heated to 60° C. for 12 hours. After cooling to room temperature, the reaction is filtered and the solid washed with water. The wet cake (500 g) is then dissolved in 1500 mL of methanol and heated to 60° C., then filtered and dried at 60° C. to give xl in 85% yield.

Phosphorous oxychloride (500 mL, 5.34 mol) is placed in a round bottom flask, followed by bromide xl (112 g, 0.50 mol) and dimethylformamide (7 mL). The reaction is heated to 120° C. for 2 hours, then the phosphorous oxychloride is removed under vacuum. The reaction is poured onto ice water and the resultant solid is filtered and washed with water. The wet cake is dissolved in ethyl acetate, and the organic layer is filtered through HighFlow and dried over sodium sulfate before being concentrated. Hexanes are added and the solid filtered, then dried at 50° C. under vacuum to give xli in 57% yield.

Chloride xli (50 g, 0.21 mol) is dissolved in toluene (1000 mL) under inert atmosphere and stirred for 15 minutes. Tributyl(vinyl) tin (65 g, 0.21 mol) and palladium tetrakis (2.5 g, 0.02 mol) is added. The reaction is heated to 90° C. for 18 hours. The mixture is cooled to room temperature, then filtered through HighFlow and washed with ethyl acetate. The organic layer is washed with water, then dried over sodium sulfate and concentrated. The crude mixture is purified by flash column chromatography (20% ethyl acetate in hexanes) to give xlii in 61% yield.

Allyl xlii (60 g, 0.26 mol) is dissolved in tetrahydrofuran (1250 mL) and water (396 mL). Osmium tetroxide (2 g, 0.0078 mol) is added, and the reaction is cooled to 0° C. Sodium periodate (121 g, 0.64 mol) in water (850 mL) is added dropwise. The reaction is stirred for 4 hours, then ethyl acetate is added and the reaction is stirred for 30 minutes. The organic layer is separated, and the aqueous layer is extracted into ethyl acetate. The combined organic layers are washed with water and dried over sodium sulfate and concentrated to give xliii in 32% yield.

Aldehyde xliii (2.0 g, 8.4 mmol) is placed in a round bottom flask, and hydroxylamine sulfate (1.4 g, 8.5 mmol) in water (6.0 mL) are added. The reaction is cooled to −15° C., and sodium hydroxide (0.35 g, 8.7 mmol) in water (3.2 mL) are added. The reaction is stirred for 2 hours, then extracted into ethyl acetate. The organic layer is dried over sodium sulfate and concentrated to give hydroxylamine xliv in 94% yield.

Hydroxylamine xliv (2.0 g, 7.93 mmol) and phosphorous oxychloride (20 mL, (21.4 mmol) are heated to 120° C. for 2 hours, after which the solvent is completely removed under vacuum. The remaining mixture is poured onto ice water, and the pH is adjusted to 7 using aqueous sodium bicarbonate. The mixture is extracted into ethyl acetate, and the organic layer is dried over sodium sulfate and concentrated to give nitrile xlv in 48% yield.

Example 16. Synthesis of 7-((1-isopropyl-1H-pyrazol-3-yl)ethynyl)quinoxaline-2-carbonitrile (xlvi)

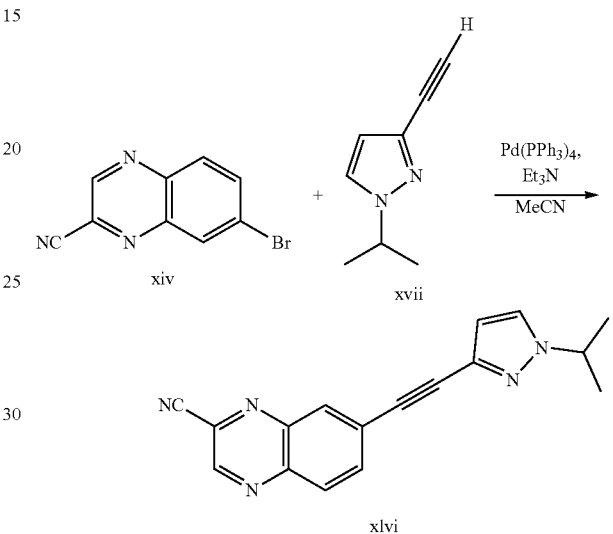

Nitrile xlv and alkyne xvii are coupled as described in Example 6. Following oxidation of alkyne xlvi (Example 6), the synthesis of compound 75 (below) is completed by following the sequence in Example 1 and installation of the amide using sulfuric acid as in Example 2.

In a prophetic example, use of 6-iodoquinazoline (CAS #848841-54-3) and 1-cyclopropyl-3-iodo-1H-pyrazole (CAS #1616069-72-7) in place of xlv and xvii permits the synthesis of compound 72.

TABLE 17

| # | Structure and Name | Physical Data (MS, m/z M + 1) | % Yield (overall) |
|---|---|---|---|
| 75 | 7-(2-(((3,5-difluorophenyl)amino)methyl)-4-(1-isopropyl-1H-pyrazol-3-yl)-1H-imidazol-5-yl)quinoxaline-2-carboxamide | 471.2 | 1.6% |

TABLE 17-continued

| # | Structure and Name | Physical Data (MS, m/z M + 1) | % Yield (overall) |
|---|---|---|---|
| 72 | 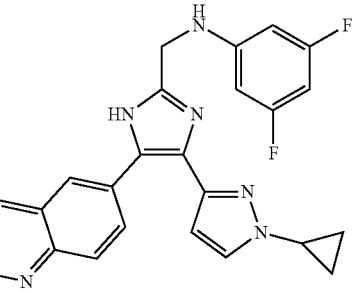<br>N-((4-(1-cyclopropyl-1H-pyrazol-3-yl)-5-(quinazolin-6-yl)-1H-imidazol-2-yl)methyl)-3,5-difluoroaniline | | |

Example 17. Synthesis of Compound 70 (6-(4-(1-cyclopropyl-1H-pyrazol-3-yl)-2-(((3,5-difluorophenyl)amino)methyl)-1H-imidazol-5-yl)imidazo[1,2-a]pyridine-3-carboxamide)

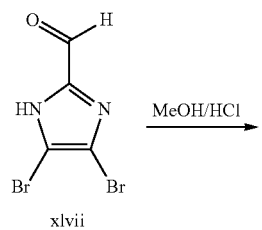
xlvii

MeOH/HCl →

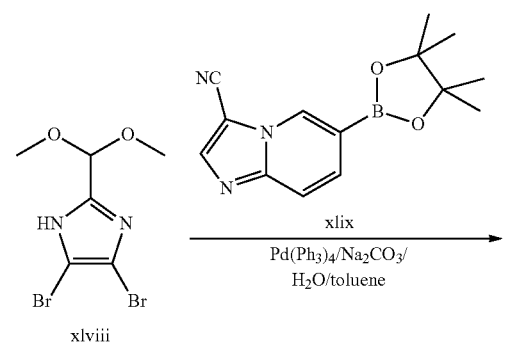
xlviii xlix
Pd(Ph₃)₄/Na₂CO₃/
H₂O/toluene
→

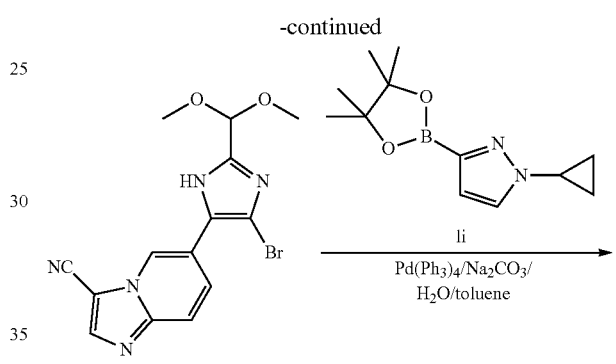
l li
Pd(Ph₃)₄/Na₂CO₃/
H₂O/toluene
→

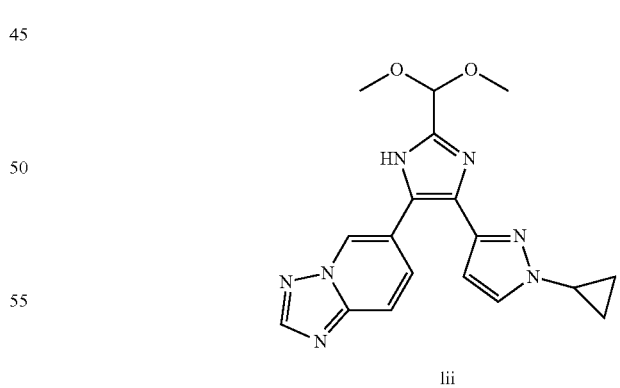
lii

In a prophetic example, aldehyde xlvii can be treated to the conditions above using known boronic ester (CAS #1989745-33-6) to give acetal 1. A second coupling gives lii, which can be subjected to the conditions described in Example 1 followed by amide hydrolysis as in Example 2 to give compound 70, shown below.

83

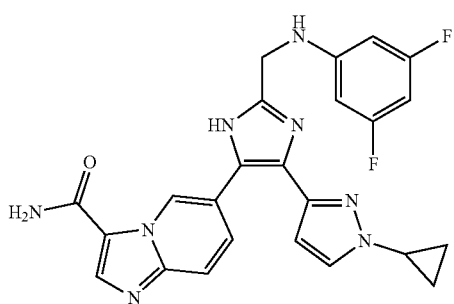 [SMILES: NC(=O)c1cnc2ccc(-c3[nH]c(CNc4cc(F)cc(F)c4)nc3-c3ccn(C4CC4)n3)cn12]

6-(4-(1-cyclopropyl-1H-pyrazol-3-yl)-2-(((3,5-difluorophenyl)amino)methyl)-1H-imidazol-5-yl)imidazo[1,2-a]pyridine-3-carboxamide Example 18. Synthesis of Compound 73 (6-(4-(1-cyclopropyl-1H-pyrazol-3-yl)-2-(((3,5-difluorophenyl)amino)methyl)-1H-imidazol-5-yl)quinazolin-4-ol)

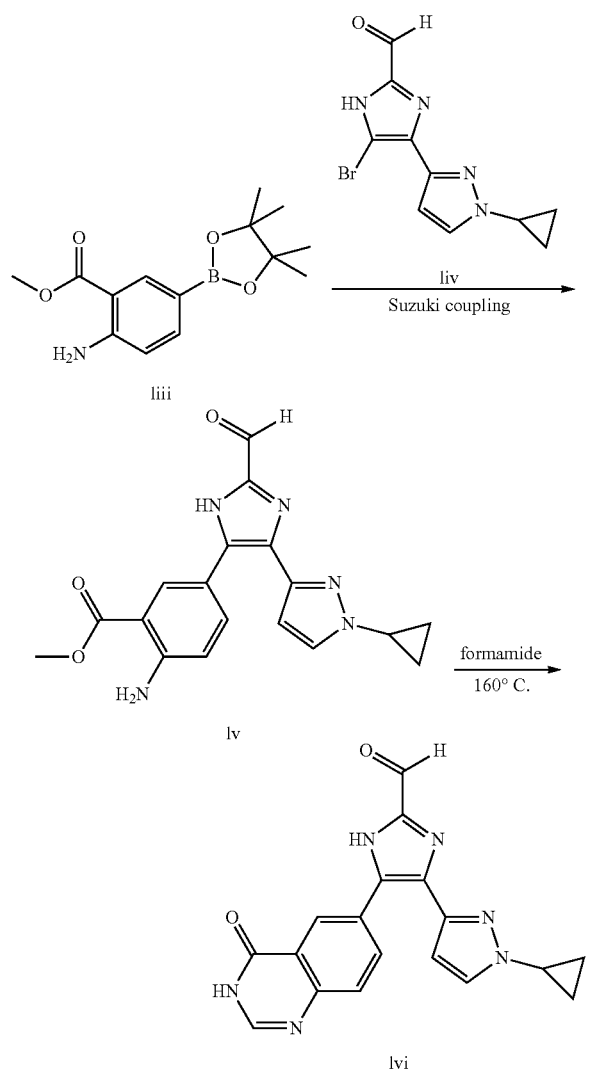

84

In a prophetic example, known boronic ester liii (CAS #363185-87-9) can undergo Suzuki coupling with bromide liv to give lv. Following treatment with formamide to yield lvi, the conditions described above in Scheme 6 can be applied to yield compound 73, shown below.

6-(4-(1-cyclopropyl-1H-pyrazol-3-yl)-2-(((3,5-difluorophenyl)amino)methyl)-1H-imidazol-5-yl)quinazolin-4-ol In a further prophetic example shown below using known boronic ester lvii (CAS #1209485-71-1) is coupled to bromide lviii via the same method.

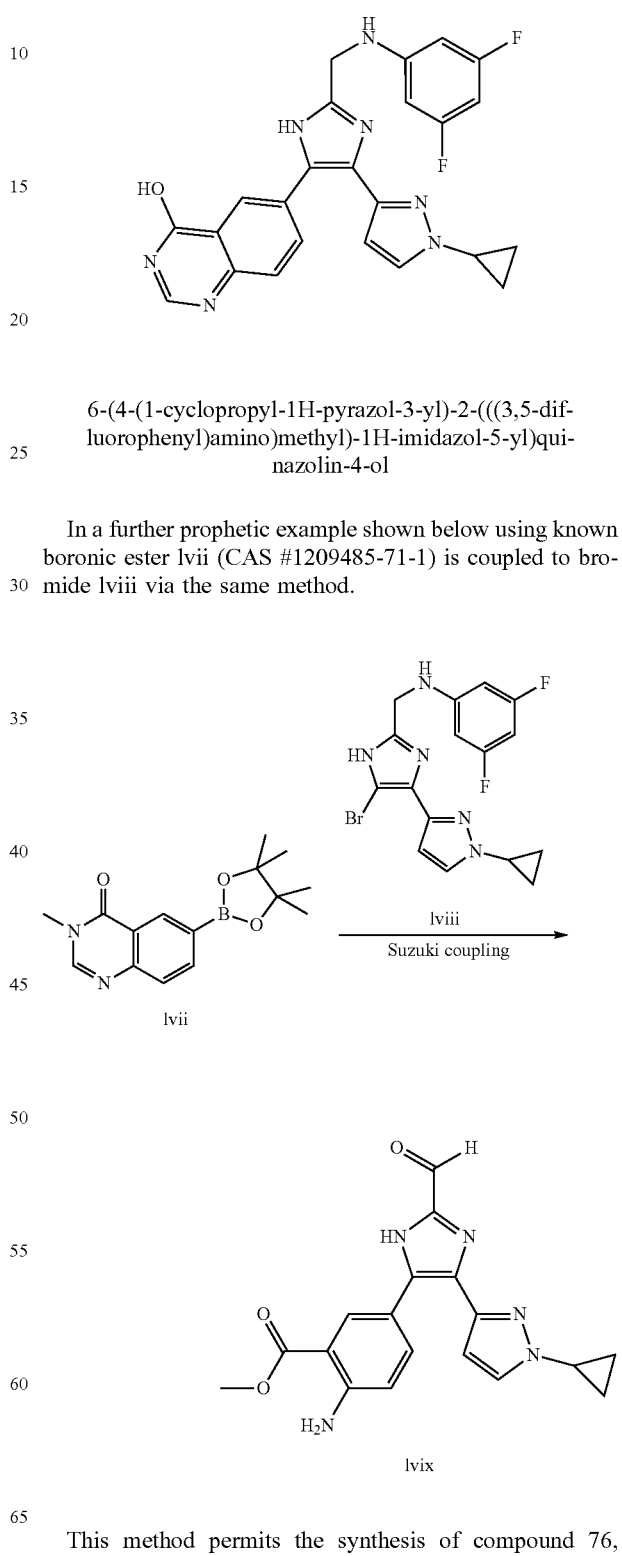

This method permits the synthesis of compound 76, shown below.

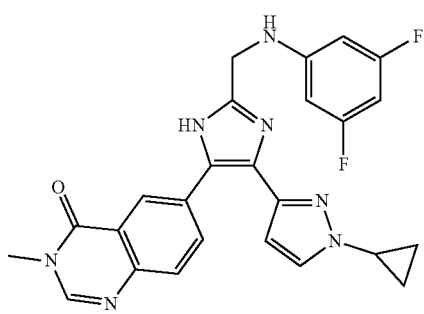 [SMILES: Cn1cnc2ccc(-c3[nH]c(CNc4cc(F)cc(F)c4)nc3-c3ccn(C4CC4)n3)cc2c1=O]

6-(4-(1-cyclopropyl-1H-pyrazol-3-yl)-2-(((3,5-difluorophenyl)amino)methyl)-1H-imidazol-5-yl)-3-methylquinazolin-4(3H)-one Example 18. Synthesis of Compound 75 (4-(4-(1-cyclopropyl-1H-pyrazol-3-yl)-2-(((3,5-difluorophenyl)amino)methyl)-1H-imidazol-5-yl)quinoline-6-carboxamide)

In a prophetic example, 4-bromoquinoline-6-carbonitrile (CAS #642477-82-5) can be converted to the corresponding alkyne and, along with 1-cyclopropyl-3-iodo-1H-pyrazole (CAS #1616069-72-7) subjected to the conditions described in Example 12 to ultimately yield compound 75 (below).

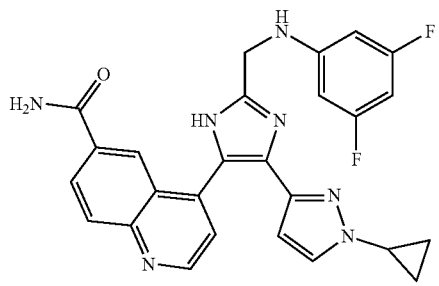 [SMILES: NC(=O)c1ccc2nccc(-c3[nH]c(CNc4cc(F)cc(F)c4)nc3-c3ccn(C4CC4)n3)c2c1]

4-(4-(1-cyclopropyl-1H-pyrazol-3-yl)-2-(((3,5-difluorophenyl)amino)methyl)-1H-imidazol-5-yl)quinoline-6-carboxamide Example 19. Formation of Hydrochloride (HCP) Salt Compound 1 is dissolved in methanolic hydrochloric acid, heated to 45° C., and stirred for 1 hour. The solution is concentrated, and the resultant solid is washed with petroleum ether (3 mL) followed by methyl t-butyl ether (2×3 mL), and dried to give 2.

This procedure can be used in the synthesis of the HCl salts shown below in Table 18.

TABLE 18

| No. | Structure and Name | % Yield |
|---|---|---|
| 2 | N-((5-([1,2,4]triazolo[1,5-a]pyridin-6-yl)-4-(1-methyl-1H-pyrazol-3-yl)-1H-imidazol-2-yl)methyl)-2-fluoroaniline hydrochloride | 80% |
| 4 | N-((5-([1,2,4]triazolo[1,5-a]pyridin-6-yl)-4-(1-methyl-1H-pyrazol-3-yl)-1H-imidazol-2-yl)methyl)aniline hydrochloride | 76% |
| 6 | N-((5-([1,2,4]triazolo[1,5-a]pyridin-6-yl)-4-(1-methyl-1H-pyrazol-3-yl)-1H-imidazol-2-yl)methyl)-3-fluoroaniline hydrochloride | 62% |
| 8 | N-((5-([1,2,4]triazolo[1,5-a]pyridin-6-yl)-4-(1-methyl-1H-pyrazol-3-yl)-1H-imidazol-2-yl)methyl)-4-fluoroaniline hydrochloride | 54% |

TABLE 18-continued

| No. | Structure and Name | % Yield |
|---|---|---|
| 10 | N-((5-([1,2,4]triazolo[1,5-a]pyridin-6-yl)-4-(1-isopropyl-1H-pyrazol-3-yl)-1H-imidazol-2-yl)methyl)aniline hydrochloride | 62% |
| 12 | N-((5-([1,2,4]triazolo[1,5-a]pyridin-6-yl)-4-(1-methyl-1H-pyrazol-3-yl)-1H-imidazol-2-yl)methyl)-4-chloroaniline hydrochloride | 41% |
| 14 | N-((5-([1,2,4]triazolo[1,5-a]pyridin-6-yl)-4-(1-methyl-1H-pyrazol-3-yl)-1H-imidazol-2-yl)methyl)-4-chloroaniline hydrochloride | <1% |
| 16 | 3-(((5-([1,2,4]triazolo[1,5-a]pyridin-6-yl)-4-(1-methyl-1H-pyrazol-3-yl)-1H-imidazol-2-yl)methyl)amino)benzonitrile hydrochloride | 24% |
| 20 | N-((5-([1,2,4]triazolo[1,5-a]pyridin-6-yl)-4-(1-isopropyl-1H-pyrazol-3-yl)-1H-imidazol-2-yl)methyl)-3-fluoroaniline hydrochloride | 81% |
| 22 | 3-fluoro-N-((4-(1-isopropyl-1H-pyrazol-3-yl)-5-(quinoxalin-6-yl)-1H-imidazol-2-yl)methyl)aniline hydrochloride | 16% |
| 26 | 3-fluoro-N-((4-(1-isopropyl-1H-pyrazol-3-yl)-5-(quinolin-6-yl)-1H-imidazol-2-yl)methyl)aniline hydrochloride | 27% |
| 31 | 2-fluoro-N-((4-(1-methyl-1H-pyrazol-3-yl)-5-(quinolin-6-yl)-1H-imidazol-2-yl)methyl)aniline hydrochloride | 16% |

TABLE 18-continued

| No. | Structure and Name | % Yield |
|---|---|---|
| 33 | 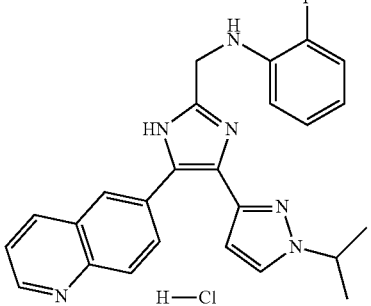<br>2-fluoro-N-((4-(1-isopropyl-1H-pyrazol-3-yl)-5-(quinolin-6-yl)-1H-imidazol-2-yl)methyl)aniline hydrochloride | 27% |
| 36 | 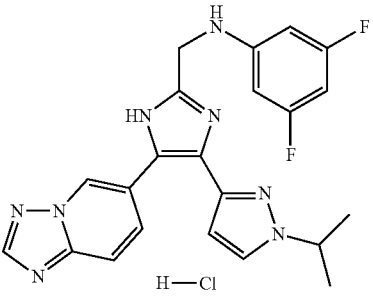<br>N-((5-([1,2,4]triazolo[1,5-a]pyridin-6-yl)-4-(1-isopropyl-1H-pyrazol-3-yl)-1H-imidazol-2-yl)methyl)-3,5-difluoroaniline hydrochloride | 13% |
| 53 | 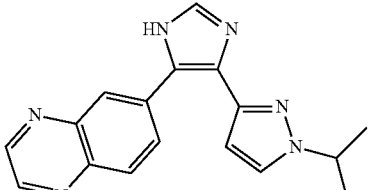<br>6-(4-(1-isopropyl-1H-pyrazol-3-yl)-1H-imidazol-5-yl)quinoxaline hydrochloride | 7% |

The invention claimed is:

1. A method of treating a disease, comprising:
administering a therapeutically effective amount of a compound of the formula

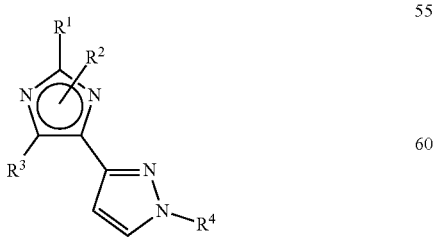

or a pharmaceutically acceptable salt, hydrate or solvate thereof to a mammal in need of treatment, wherein:

the disease is selected from the group consisting of glioma, pancreatic cancer, myelodysplastic syndrome, myelofibrosis, liver cancer, and colon cancer;

$R^1$ is selected from the group consisting of a group of the formula —X—Y—Z, the formula —X—Z, the formula —Y—Z, and the formula —Z;

X is O; $NR^5$; S; $CR^6R^7$; C=O; C=S; or an alkyl chain containing 1 to 6 carbon atoms;

Y is O, $NR^5$, S, $CR^6R^7$, C=O, C=S, or an alkyl chain containing 1 to 6 carbon atoms, $R^5$ is hydrogen; aryl; a heteromonocyclic group comprising a heteroatom selected from nitrogen, oxygen, and sulfur; a heterobicyclic group comprising a heteroatom selected from nitrogen, oxygen, and sulfur; an alkyl chain containing 1 to 6 carbon atoms; an alkenyl chain containing 1 to 6 carbon atoms; or an alkynyl chain containing 1 to 6 carbon atoms;

$R^6$ is hydrogen; or an alkyl chain containing 1 to 6 carbon atoms;

$R^7$ is hydrogen; an alkyl chain containing 1 to 6 carbon atoms; an alkenyl group containing 1 to 6 carbon atoms; an alkynyl chain containing 1 to 6 carbon atoms; or an alkoxy group containing 1 to 6 carbon atoms;

Z is a phenyl group; a substituted phenyl group, or substituted heteromonocyclic group comprising a heteroatom selected from nitrogen, oxygen, and sulfur, where 1 to 5 substituents are selected from a group consisting of halogens, alkyl groups containing 1 to 6 carbon atoms, alkenyl groups containing 1 to 6 carbon atoms, alkynyl groups containing 1 to 6 carbon atoms, a phenyl group, a pyridyl group, alkoxy groups containing 1 to 6 carbon atoms, a hydroxyl group, a carboxamido group, a carbamoyl group, and a cyano group; a hydrogen atom; an alkyl group containing 1 to 12 carbon atoms; an alkenyl group containing 2 to 12 carbon atoms; an alkynyl group containing 1 to 6 carbon atoms; a cycloalkyl group containing 3 to 7 carbon atoms; an alkyl group containing 1 to 12 carbon atoms substituted by an alkenyl group containing 1 to 6 carbon atoms, an alkynyl group containing 1 to 6 carbon atoms, an alkoxy group containing 1 to 6 carbon atoms, a hydroxyl group, an alkoxyphenylalkoxy group having 8 to 12 carbon atoms, a morpholino group, a piperidinyl group, or a pyrrolidino group; an alkyl group having 1 to 6 carbon atoms substituted with 1 to 5 halogen atoms; a cycloalkyl group containing 3 to 9 carbon atoms substituted with an oxo group; a heteromonocyclic or heterobicyclic group comprising a heteroatom selected from nitrogen, oxygen, and sulfur; a heteromonocyclic or a heterobicyclic group comprising a heteroatom selected from nitrogen, oxygen, and sulfur and substituted with 1 to 5 members selected from a group consisting of halogens, alkyl groups containing 1 to 6 carbon atoms, alkenyl groups containing 1 to 6 carbon atoms, alkynyl groups containing 1 to 6 carbon atoms, alkoxy groups containing 1 to 6 carbon atoms, a hydroxyl group, a carboxamido group, a carbamoyl group, a cyano group, and a tetrahydropyranyl group; a tetrahydrofuranyl group; a 4-piperidinyl group; a piperidinyl group substituted with an alkyl group containing 1 to 6 carbon atoms; a t-butoxycarbonyl group; a cyclohexanespiro-2'-(1,3-dioxoranyl) group; or a pyr-rolidin-2-one-5-yl group;

R² is a hydrogen atom; an alkyl group containing 1 to 6 carbon atoms; an alkenyl group containing 1 to 6 carbon atoms; an alkynyl group containing 1 to 6 carbon atoms, a cycloalkyl group containing 3 to 7 carbon atoms; an alkyl group containing 1 to 6 carbon atoms, substituted with a cycloalkyl group containing 3 to 7 carbon atoms; an alkyl group containing 1 to 6 carbon atoms, substituted with 2 to 7 halogens; a phenylalkyl group containing 7 to 12 carbon atoms; or a phenylalkyl group containing 7 to 12 carbon atoms, substituted with a hydroxyl group, an alkoxy group containing 1 to 6 carbon atoms, an alkoxy group containing 1 to 6 carbon atoms substituted with an alkoxy group containing 1 to 6 carbon atoms, or an alkoxy group having 1 to 6 carbon atoms substituted with an alkylamino group containing 1 to 6 carbon atoms;

R³ is a phenyl group; a phenyl group substituted with 1 to 5 members selected from a group consisting of halogens, alkyl groups containing 1 to 6 carbon atoms, alkenyl groups containing 1 to 6 carbon atoms, alkynyl groups containing 1 to 6 carbon atoms, alkoxy groups containing 1 to 6 carbon atoms, a phenyl group, a pyridyl group, a hydroxyl group, a carboxamido group, a carbamoyl group, and a cyano group; a heteromonocyclic or heterobicyclic group comprising a heteroatom selected from nitrogen, oxygen, and sulfur; and a heteromonocyclic or a heterobicyclic group comprising a heteroatom selected from nitrogen, oxygen, and sulfur and substituted with 1 to 5 members selected from a group consisting of halogens, alkyl groups containing 1 to 6 carbon atoms, a phenyl group, a pyridyl group, alkoxy groups containing 1 to 6 carbon atoms, a hydroxyl group, a carboxamido group, a carbamoyl group, or a cyano group; or a 3-methylquinazolin-4(3H)-one; and R⁴ is a hydrogen atom; an alkyl group containing 1 to 12 carbon atoms; an alkenyl group containing 1 to 6 carbon atoms; an alkynyl group containing 1 to 6 carbon atoms; a cycloalkyl group containing 3 to 7 carbon atoms; an alkyl group containing 1 to 12 carbon atoms substituted by an alkoxy group containing 1 to 6 carbon atoms, a hydroxyl group, an alkoxyphenylalkoxy group having 8 to 12 carbon atoms, a morpholino group, a piperidinyl group, or a pyrrolidino group; an alkyl group having 1 to 6 carbon atoms substituted with 1 to 7 halogen atoms; a cycloalkyl group containing 3 to 9 carbon atoms substituted with an oxo group; a tetrahydropyranyl group; a tetrahydrofuranyl group; or a 4-piperidinyl group.

2. The method of claim 1, wherein the compound is selected from the group consisting of:

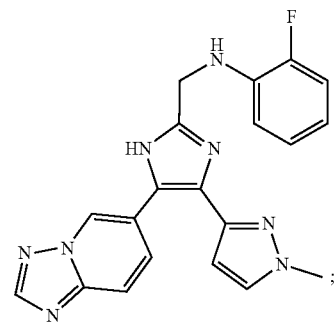

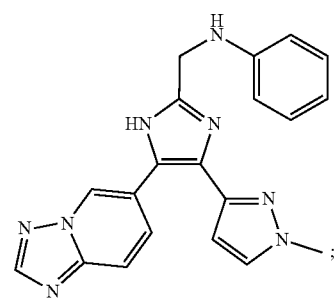

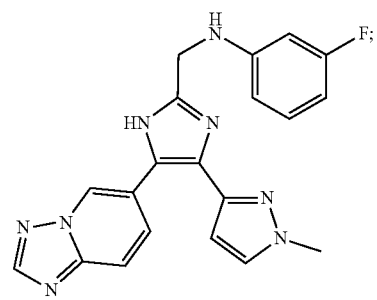

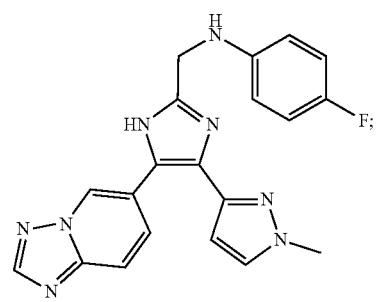

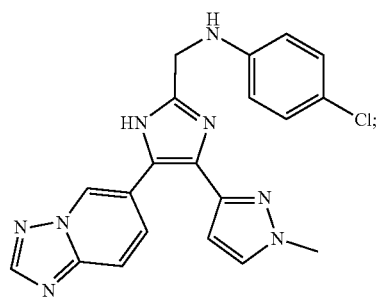

93
-continued
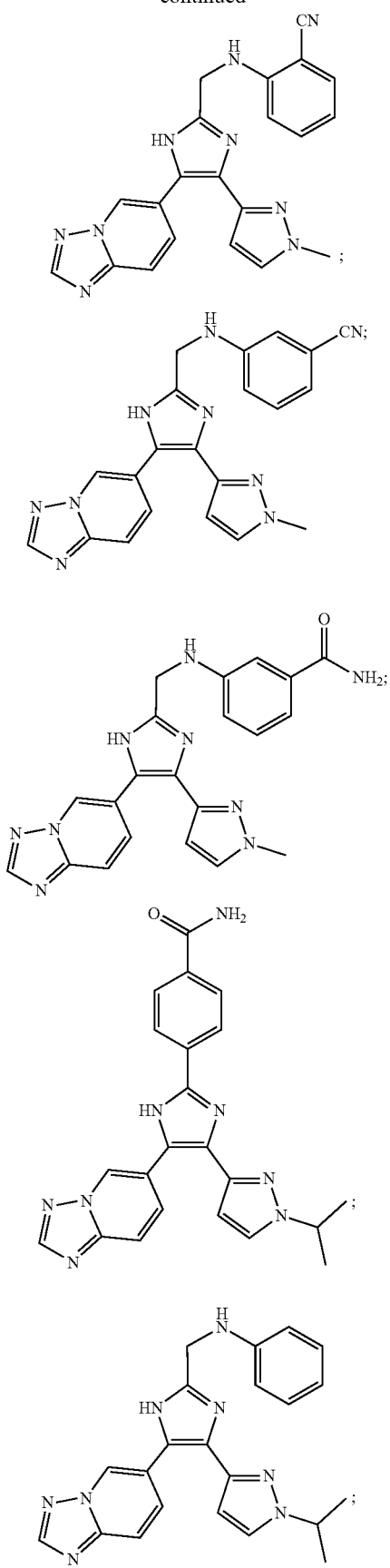
94
-continued
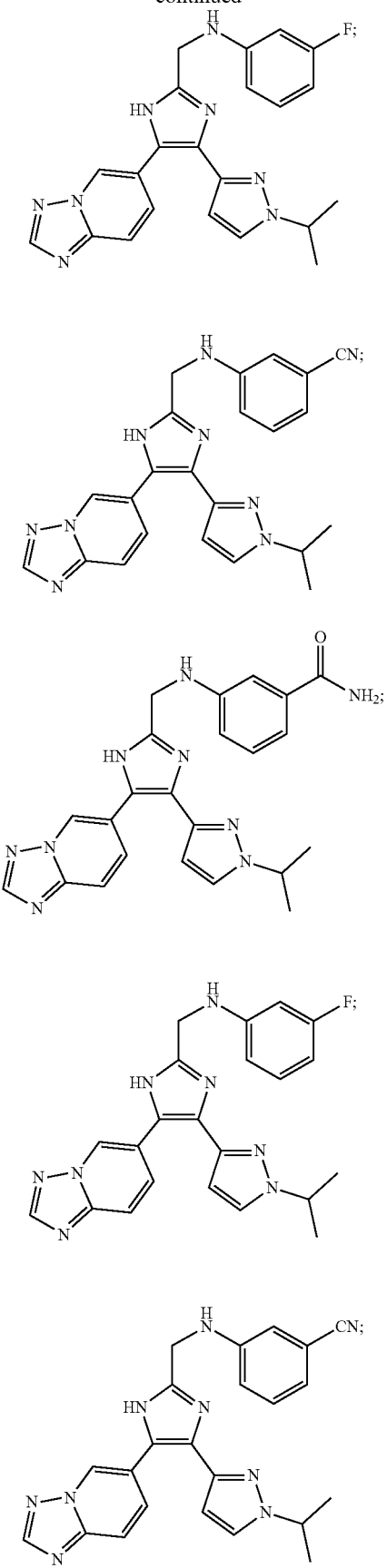

-continued
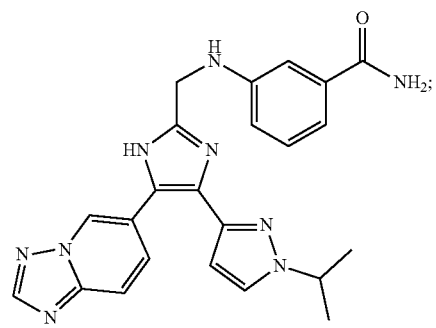
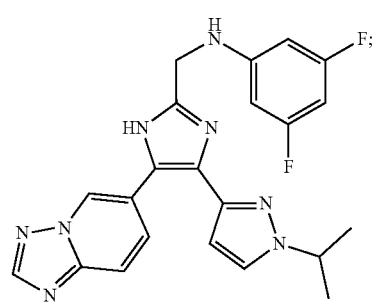
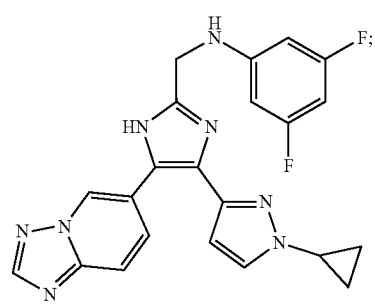
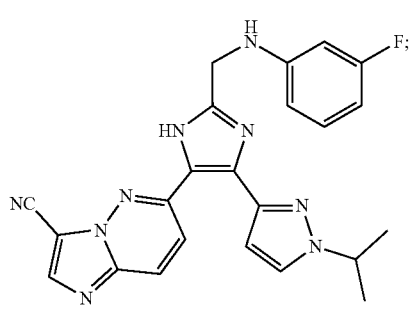
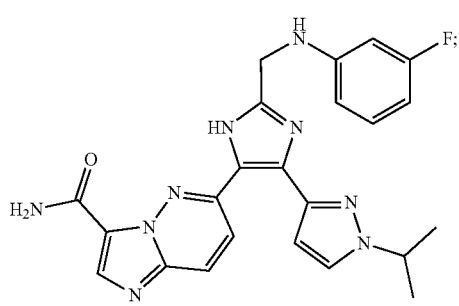
-continued
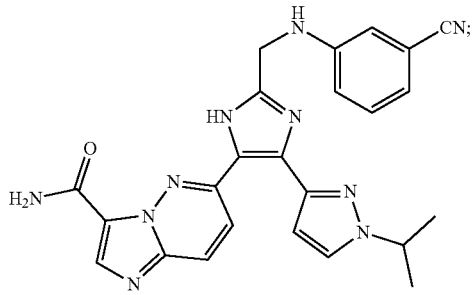
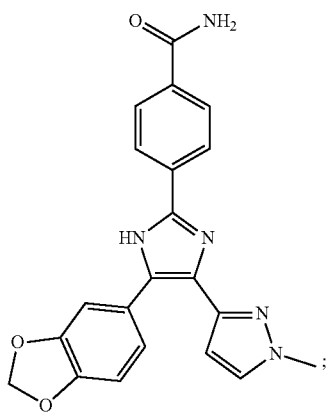
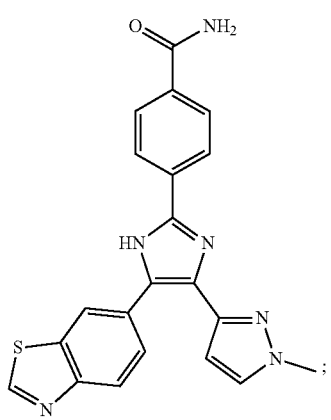
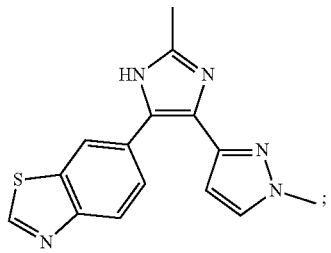
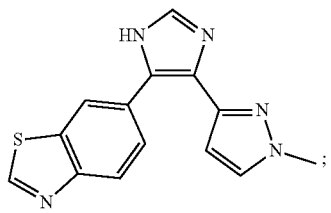

97
-continued
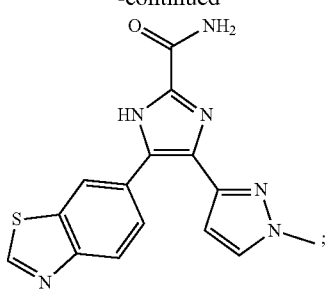
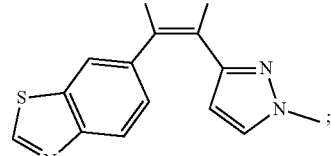
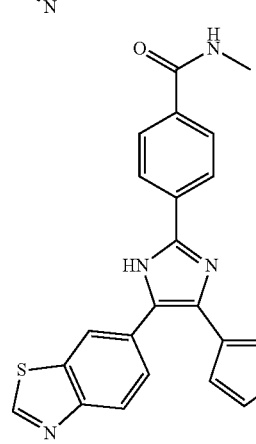
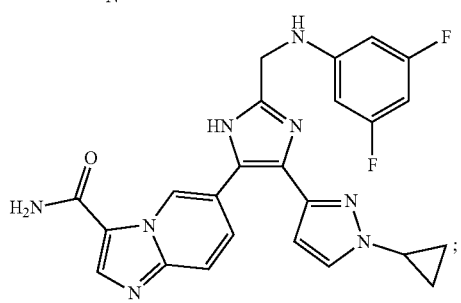
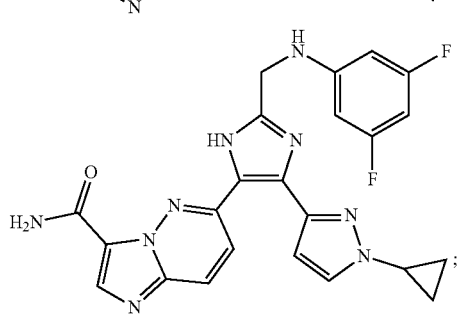
98
-continued
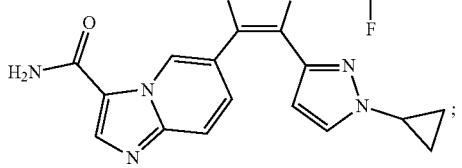
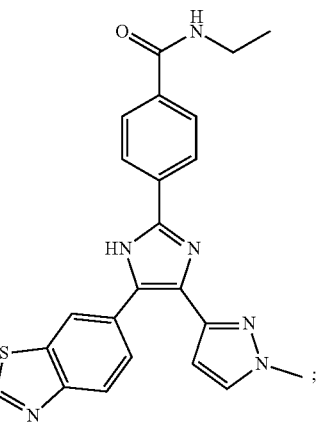
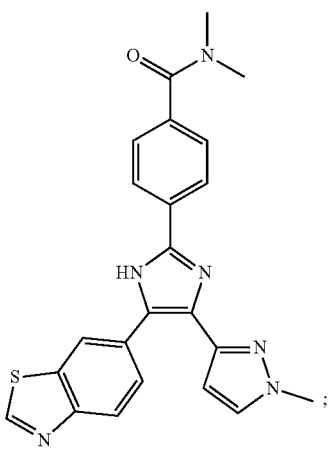
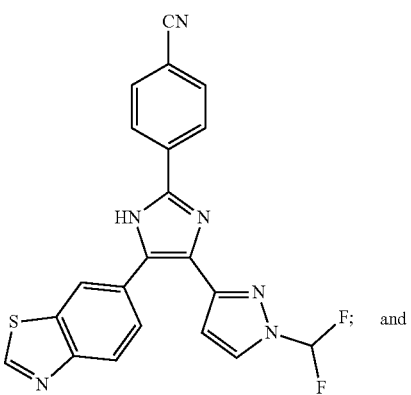

99
-continued
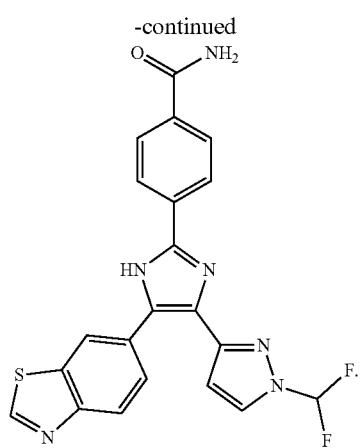
100
-continued
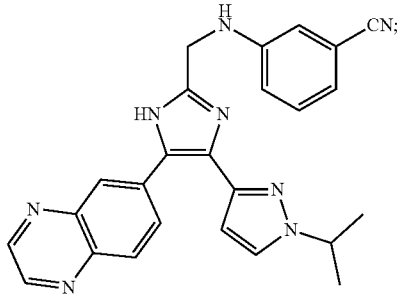
3. The method of claim 1, wherein the compound is selected from the group consisting of:
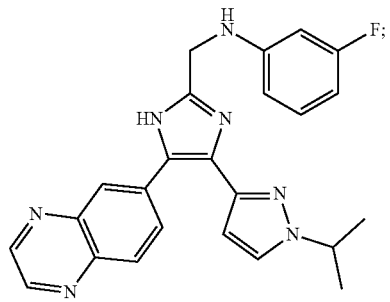
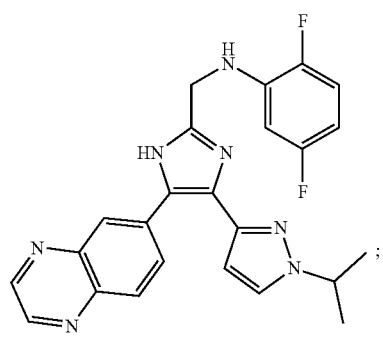
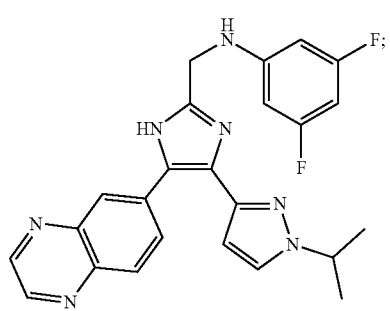
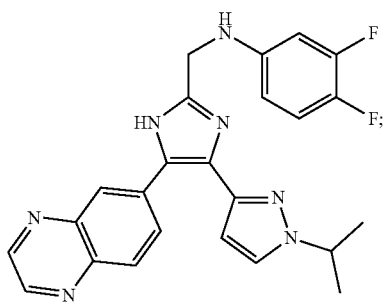
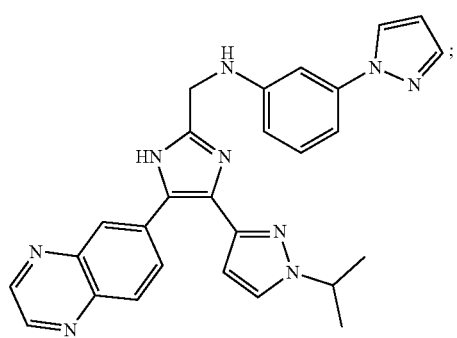
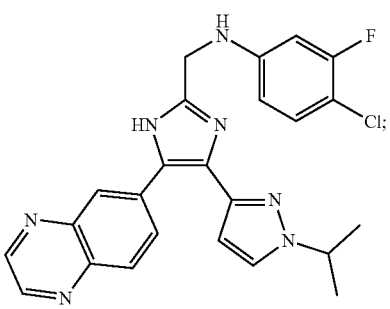

101
-continued
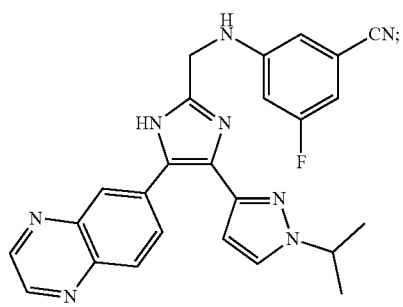
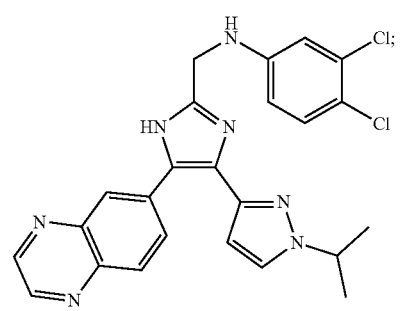
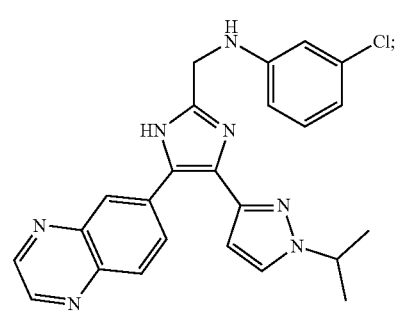
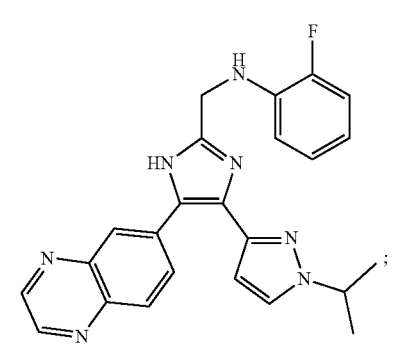
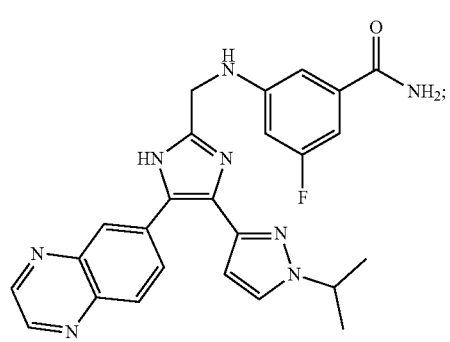
102
-continued
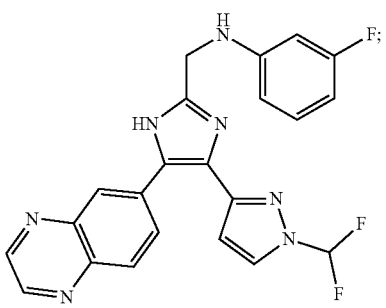
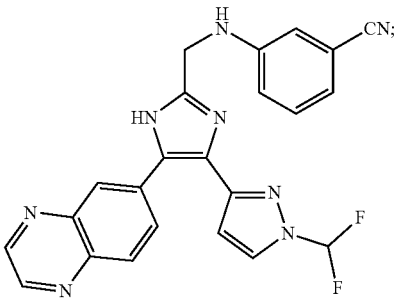
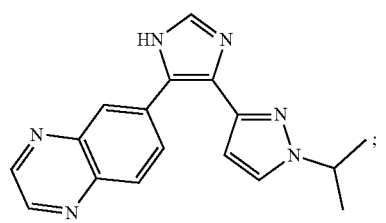
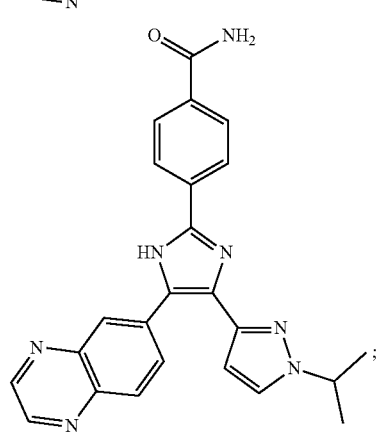
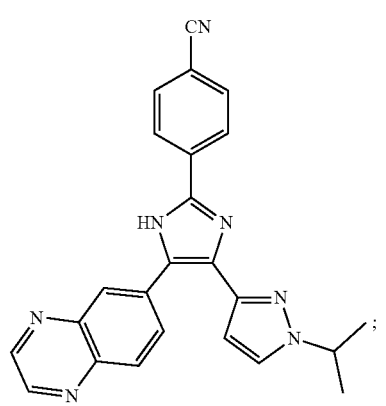

103
-continued
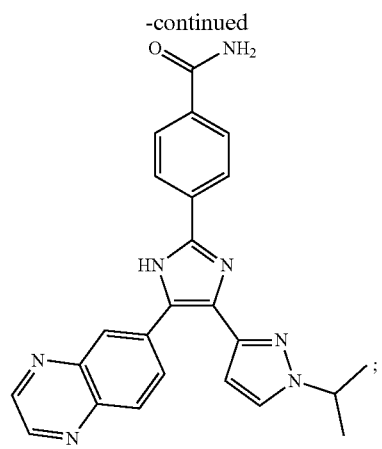
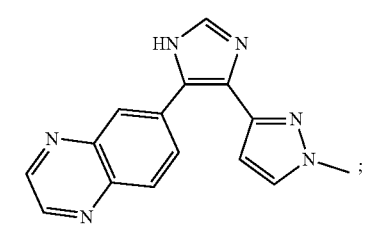
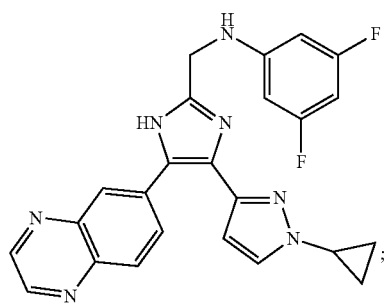
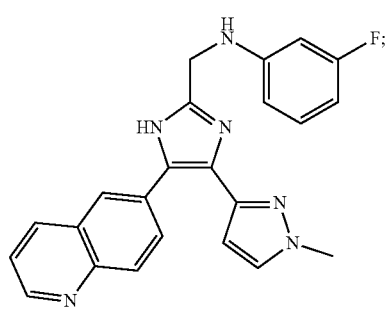
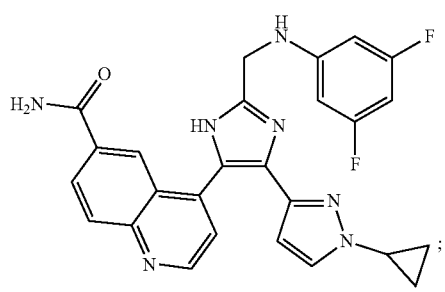
104
-continued
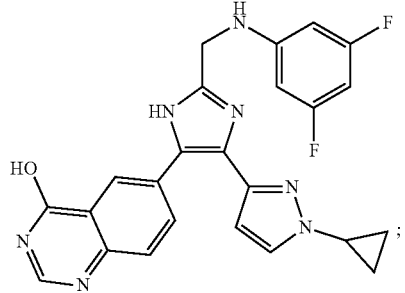
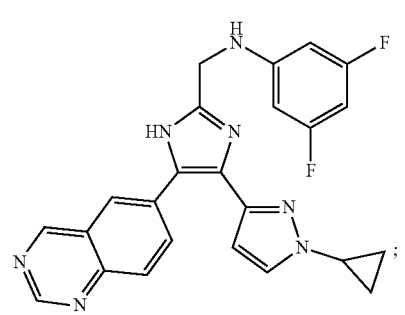
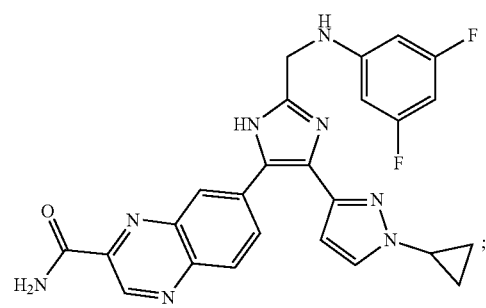
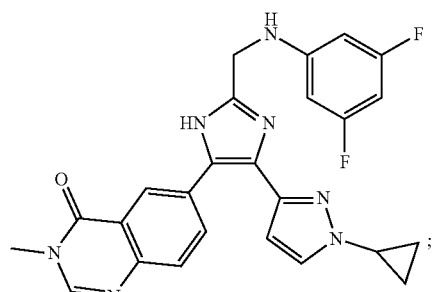
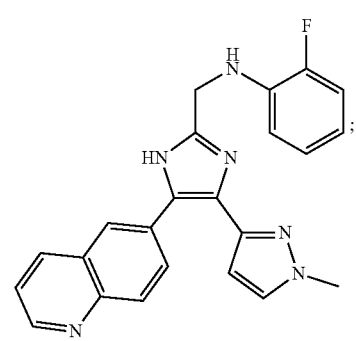

-continued
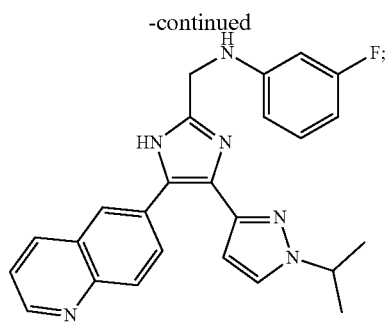
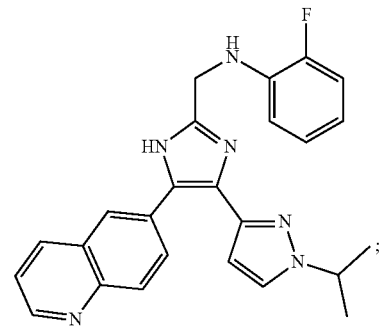
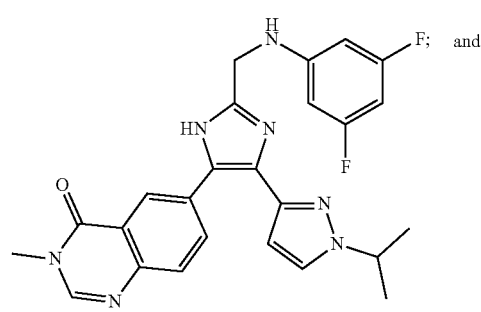 and
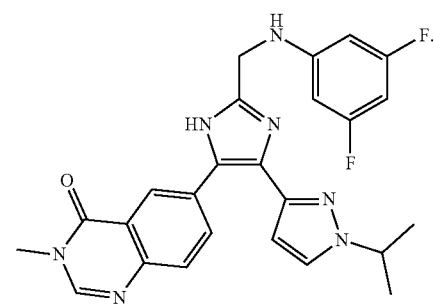
4. The method of claim 1, wherein the compound is:
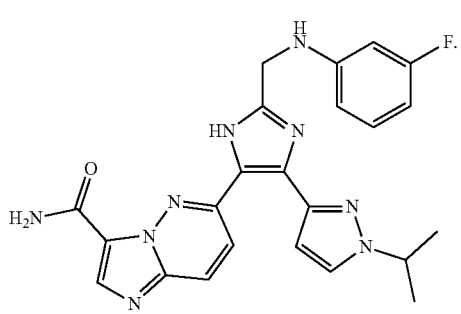 [SMILES: CC(C)n1ccc(-c2nc(CNc3cccc(F)c3)[nH]c2-c2ccc3ncc(C(N)=O)n3n2)n1]
5. The method of claim 1, wherein the compound is:
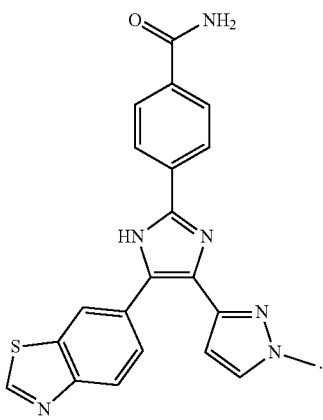 [SMILES: Cn1ccc(-c2nc(-c3ccc(C(N)=O)cc3)[nH]c2-c2ccc3ncsc3c2)n1]
6. The method of claim 1, wherein the compound is:
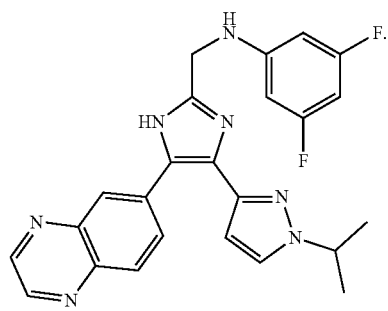 [SMILES: CC(C)n1ccc(-c2nc(CNc3cc(F)cc(F)c3)[nH]c2-c2ccc3nccnc3c2)n1]
7. The method of claim 1, wherein the compound is:
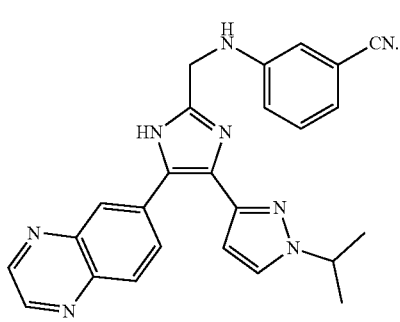 [SMILES: CC(C)n1ccc(-c2nc(CNc3cccc(C#N)c3)[nH]c2-c2ccc3nccnc3c2)n1]

8. The method of claim 1, wherein the compound is:
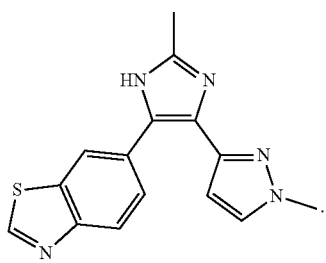 [SMILES: Cc1nc(-c2ccn(C)n2)c(-c2ccc3ncsc3c2)[nH]1]
9. The method of claim 1, wherein the compound is:
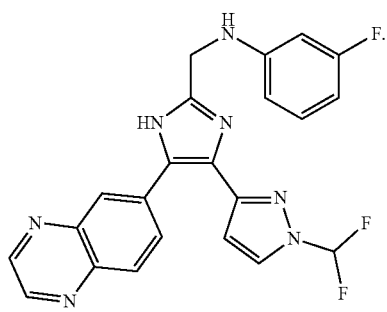 [SMILES: Fc1cccc(NCc2nc(-c3ccn(C(F)F)n3)c(-c3ccc4nccnc4c3)[nH]2)c1]
10. The method of claim 1, wherein the compound is:
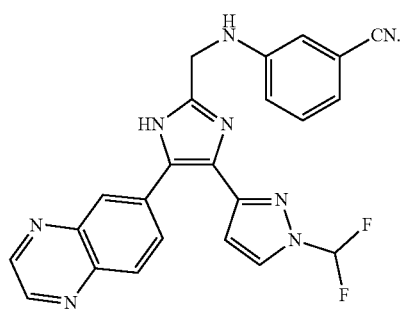 [SMILES: N#Cc1cccc(NCc2nc(-c3ccn(C(F)F)n3)c(-c3ccc4nccnc4c3)[nH]2)c1]
11. The method of claim 1, wherein the compound is:
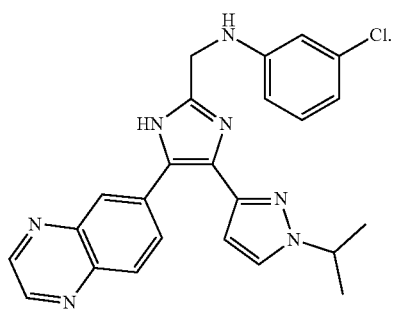 [SMILES: CC(C)n1ccc(-c2nc(CNc3cccc(Cl)c3)[nH]c2-c2ccc3nccnc3c2)n1]
12. The method of claim 1, wherein the compound is:
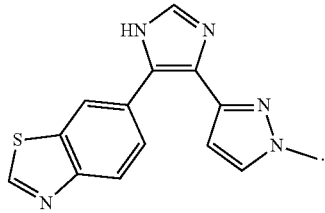 [SMILES: Cn1ccc(-c2nc[nH]c2-c2ccc3ncsc3c2)n1]
13. The method of claim 1, wherein the compound is:
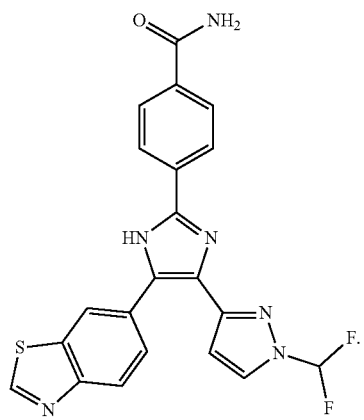 [SMILES: NC(=O)c1ccc(-c2nc(-c3ccn(C(F)F)n3)c(-c3ccc4ncsc4c3)[nH]2)cc1]
14. The method of claim 1, wherein the compound is:
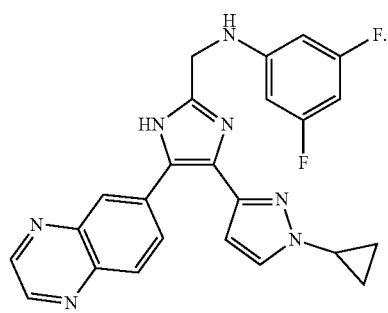 [SMILES: Fc1cc(F)cc(NCc2nc(-c3ccn(C4CC4)n3)c(-c3ccc4nccnc4c3)[nH]2)c1]
15. The method of claim 1, wherein the compound is:
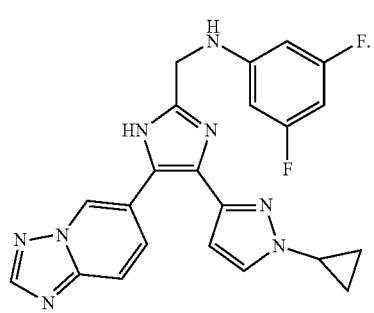 [SMILES: Fc1cc(F)cc(NCc2nc(-c3ccn(C4CC4)n3)c(-c3ccc4ncnn4c3)[nH]2)c1]

16. The method of claim 1, wherein the compound is:
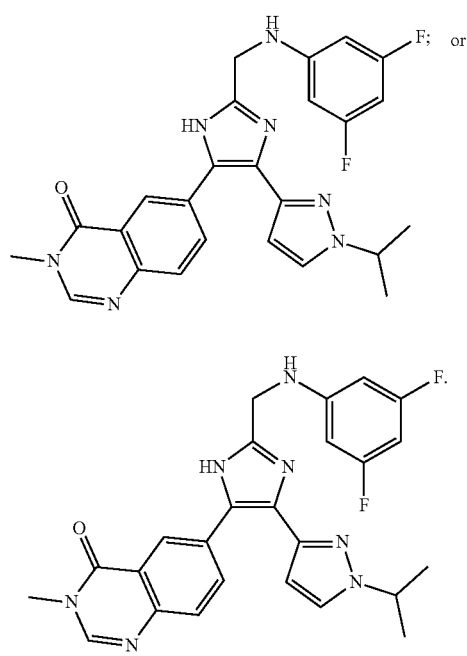 or
17. The method of claim 1, wherein the compound is:
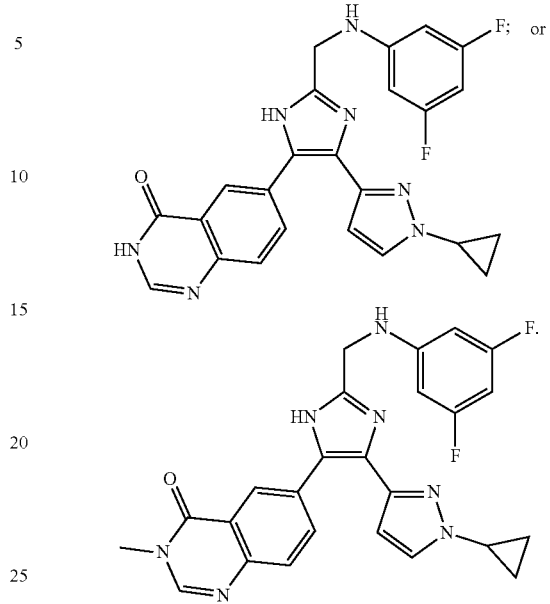
* * * * *